United States Patent
Chin et al.

(10) Patent No.: US 12,037,625 B2
(45) Date of Patent: *Jul. 16, 2024

(54) CELL HYDROLYSATE COMPOSITION FROM CULTIVATED CELLS AND APPLICATIONS THEREOF

(71) Applicant: Avant Meats Company Limited, Hong Kong (CN)

(72) Inventors: Po San Mario Chin, Hong Kong (CN); Kai Yi Carrie Chan, Hong Kong (CN); Chun Hei Poon, Hong Kong (CN)

(73) Assignee: Avant Meats Company Limited, Singapore (SG)

(*) Notice: Subject to any disclaimer, the term of this patent is extended or adjusted under 35 U.S.C. 154(b) by 0 days.

This patent is subject to a terminal disclaimer.

(21) Appl. No.: 17/670,300

(22) Filed: Feb. 11, 2022

(65) Prior Publication Data

US 2022/0333148 A1 Oct. 20, 2022

Related U.S. Application Data

(62) Division of application No. 17/243,493, filed on Apr. 28, 2021, now Pat. No. 11,306,342.

(60) Provisional application No. 63/173,332, filed on Apr. 9, 2021.

(51) Int. Cl.
| | |
|---|---|
| A61K 38/39 | (2006.01) |
| A23J 3/04 | (2006.01) |
| A23J 3/34 | (2006.01) |
| A23L 33/18 | (2016.01) |
| A61K 8/65 | (2006.01) |
| A61K 38/18 | (2006.01) |
| A61Q 19/00 | (2006.01) |
| C07K 1/12 | (2006.01) |
| C12P 21/06 | (2006.01) |

(52) U.S. Cl.
CPC ............... *C12P 21/06* (2013.01); *A23J 3/04* (2013.01); *A23J 3/342* (2013.01); *A23L 33/18* (2016.08); *A61K 8/65* (2013.01); *A61K 38/18* (2013.01); *A61K 38/39* (2013.01); *A61Q 19/00* (2013.01); *C07K 1/12* (2013.01); *A23V 2002/00* (2013.01)

(58) Field of Classification Search
CPC ........... C12P 21/06; A61K 8/65; A61K 38/39; C07K 1/12; A61Q 19/00; A23J 3/04; A23J 3/342; A23L 33/18

See application file for complete search history.

(56) References Cited

U.S. PATENT DOCUMENTS

| | | |
|---|---|---|
| 6,126,935 A | 10/2000 | Van Bossuyt |
| 2022/0162662 A1 | 5/2022 | Chin |

FOREIGN PATENT DOCUMENTS

| | | |
|---|---|---|
| CN | 1720064 A | 1/2006 |
| CN | 104109705 A | 10/2014 |
| CN | 106749634 A | 5/2017 |
| CN | 106805252 A | 6/2017 |
| CN | 107400633 A | 11/2017 |
| CN | 110201000 A | 9/2019 |

OTHER PUBLICATIONS

Petrova et al., "Production of fish protein hydrolysates step by step: technological aspects, equipment used, major energy costs and methods of their minimizing," Int. Aquat. Res., 2018, 10: 223-241. (Year: 2018).*
Kibenge FSB, "Descriptions of major farmed aquatic animal species," Auqculture Pathophysiology, 2022, pp. 1-44. (Year: 2022).
Office Action (Non-Final Rejection) dated Jul. 7, 2023 for U.S. Appl. No. 17/670,288 (pp. 1-10).
Zhao et al., "Anti-Fatigue Effect by Peptide Fraction from Protein Hydrolysate of Croceine Croaker (*Psuedosciaena crocea*) Swim Bladder through Inhibiting the Oxidative Reactions including DNA damage," Marine Drugs, 2016, 14 (221): 1-18. (Year: 2016).
Chen et al., "Preparation and functional evaluation of collagen oligopeptide-rich hydrolysate from fish skin with the serine collagenolytic protease from *Pseudoalteromonas* sp. SM9913," Nature, Scientific Reports, Nov. 16, 2017, pp. 1-13. (Year: 2017).
CN 104109705 Machine translation, Oct. 22, 2014, pp. 1-13. (Year: 2014).
China National Intellectual Property Administration, International Search Report, dated Feb. 25, 2021, 4 pages.
China National Intellectual Property Administration, Written Opinion, dated Feb. 22, 2021, 3 pages.
Gene News, CELLine, A double-compartment cell cell culture device, No. 2, dated Dec. 31, 2007, 2 pages.
Giron-Calle et al., "Chickpea protein hydrolysate as a substitute for serum in cell culture," Cytotechnology, 2008, 57: 263-272. (Year: 2008).
International Search Report and Written Opinion for App. No. PCT/IB2020/060727, dated Feb. 23, 2021, 6 pages.
Jiang et al., "Therapeutic Effect of Polysaccharide of Large Yellow Croaker Swim Bladder on Lupus Nephritis of Mice," Nutrients, 2014, 6: 1223-1235. (Year: 2014).
Liu et al., "Potential Application of Hydrolyzed Fish Collagen for Inducing the Multidirection of Rat Bone Marrow Mesenchymal Stem Cells," BioMacromolecules, Dec. 23, 2013, pp. 436-443. (Year: 2013).
Notice of Allowance and Fees from corresponding U.S. Appl. No. 17/243,493, mailed on Mar. 2, 2022, 13 pages.
Office Action (Final Rejection) dated Feb. 8, 2024 for U.S. Appl. No. 17/670,288 (pp. 1-13).

\* cited by examiner

*Primary Examiner* — Julie Ha
(74) *Attorney, Agent, or Firm* — Loeb & Loeb LLP

(57) ABSTRACT

A cell hydrolysate composition is described, wherein the composition comprises substantially all protein polypeptides and/or polypeptide fragments derived substantially from all the proteins in a cell from an in vitro cell culture.

5 Claims, 5 Drawing Sheets

Specification includes a Sequence Listing.

CELL HYDROLYSATE COMPOSITION FROM CULTIVATED CELLS AND APPLICATIONS THEREOF

CROSS REFERENCE TO RELATED APPLICATIONS

This application is a divisional application of U.S. patent application Ser. No. 17/243,493, filed on Apr. 28, 2021, which further claims priority to a provisional application Ser. No. 63/173,332, filed on Apr. 9, 2021. This application further claims the priority of PCT application No. PCT/IB2020/060727 filed Nov. 14, 2020, which claims priority to a U.S. provisional patent application Ser. No. 62/942,568, filed on Dec. 2, 2019. All applications identified above are hereby incorporated by reference in their entirety.

TECHNICAL FIELD

Embodiments discussed herein generally relate to cell hydrolysate composition from cultivated cells. Embodiments discussed herein also generally relate to the applications of the cell hydrolysate composition from cultivated cells and the process of making thereof. In particular, protein polypeptides and/or polypeptide fragments derived from cultivated cells.

BACKGROUND

Animal meat is high in protein, and supplies all the amino acids needed to build the protein used to support body functions. Meat is often used to produce animal derived raw materials, including but not limited to, proteins, growth factors, cytokines, etc. Such animal derived raw materials have a lot of applications, which are often included in dietary supplements, hair care, skincare, cosmetic and wound care products, etc. The growth factors, cytokines, and extracellular matrix (ECM) proteins may stimulate skin tissue repair and regeneration. The hyaluronic acid derivatives may moisturize the skin and decrease wrinkles. The antioxidants may protect against aging-associated oxidative stress. The collagen may speed up healing. However, these animal derived raw materials are traditionally obtained from animals or fish that are reared on farms or caught in the wild. Similarly, plant derived raw materials (together with animal derived raw materials, "derived raw materials"), which may contain a lot of useful plant specific proteins, growth factors, cytokines, etc, are now obtained from harvesting plants from farm or in the wild. However, creating derived raw materials from living animals and living plants has the following drawbacks.

First, it requires a constant supply of animal and plant sources. An increase in the demand for animal products causes more animals to suffer and be killed in farms and slaughterhouses. The growth in keeping livestock may also provide an additional burden to the environment or ecosystem. Raising livestock and farming could cause deforestation, increase in clean water consumption, increase in contamination to the environment (for example due to run off of animal wastes or pesticides and other chemicals used in farming to promote plant growth), excessive use of natural resources (for example, over farming and overfishing). These could lead to depletion of natural ecosystems and decrease biodiversity of the earth. Further, it may also give rise to animal abuse and welfare issues. In addition, instability in harvesting is the inherent characteristic of raising livestock and farming as it depends on a lot of uncontrollable factors including weather and climate.

Second, only targeted proteins are extracted and the rest of other functional proteins produced in the wild animals or wild plants are lost. Usually, the derived raw materials are created by extracting certain target/interested proteins from wild animals or wild plants. During extraction process, parts of animals and/or plants are harvested and the tissues therefrom (for example, animal skin and plant cell wall) are broken down through a series of processes. The processes may include the use of a combination of chemical, thermal and/or mechanical energy. The processes may lead to loss of certain proteins due to changes in pH, temperature and other conditions. As a result, non-target/non-interested proteins or nutrients are not captured in the extraction processes. However, it is desirable to also include those non-target/non-interested proteins in the derived raw materials because they involve trace amounts of functional proteins, which could be beneficial to certain purposes. For example, the total nutrition in oranges may be more beneficial to a human for a certain purpose compared to just vitamin C extracted from the orange. Moreover, raising animals or growing plants only to obtain some usable parts to generate derived raw materials is highly inefficient.

Third, it involves the use of harmful chemicals. For example, extracting collagen from fish skin involves a series of steps including the steps of mixing the fish skins with alkaline and acidic solutions. This provides an additional burden to the environment or ecosystem. Also, it may contribute to potential occupational hazards. The derived raw materials may also contain harmful residual chemicals.

Fourth, there are safety concerns due to the presence of environmental contaminants (heavy metal, antibiotics, micro plastics, herbicides, fungicides, insecticides), adventitious agents (bacteria, viruses, fungi, transmissible spongiform encephalopathy agents), and allergens in the domesticated and wild animals and plants.

Fifth, there are difficulties in controlling the molecular profile and determining the consistency of animal-derived (e.g. animal serum) and plant-derived (e.g. plant extract, plant hydrolysate) raw materials. Each batch of animal-derived or plant-derived raw materials is created from different batches of animal and plant, which can deviate significantly due to variations of temperature, time of harvest, types of animal feed and fertilizers, presence of pest and parasites, etc. Some molecules in a certain batch may trigger an allergic reaction in some individuals.

Sixth, further, if the animal-derived and plant-derived raw materials are obtained from wild animals and wild plants, it is very difficult to trace back to the origin.

Alternatively, derived raw materials may be created by using recombinant organisms. However, this method involves the use of genetically modified organisms, which could be harmful to the environment when such organisms are released accidentally. Furthermore, only one (1) protein may be produced per production line. This method is inefficient for multiple proteins derived from raw materials. In addition, the protein produced by the recombinant organisms has to be further isolated and purified. The isolation and purification typically involve multiple steps which lead to an increase in production cost. Moreover, there may be variations in the folding of the protein produced by this method. Some functions may be lost in some variations.

Alternatively, the spent or conditioned medium may also be a source of functional protein(s). "spent", "spent medium", "spent media", "conditioned media" or "conditioned medium" are the culture medium that has been incubated with cells. However, similar to the above methods, it has several drawbacks. Firstly, it requires a constant supply of animal and plant sources. The disadvantages thereof have been discussed in the foregoing and therefore not repeated here. Secondly, there are contamination concerns due to the presence of environmental contaminants (heavy metal, antibiotics, micro plastics, herbicides, fungicides, insecticides), adventitious agents (bacteria, viruses, fungi, transmissible spongiform encephalopathy agents), and allergens in the wild animals and wild plants sources. Thirdly, unwanted metabolites and wastes in the spent medium may affect the purity of the final product. Additional purification steps would lead to an increase in production costs.

In vitro meat production is the process by which muscle tissue or organ tissue from animals are grown in laboratories using cell culture techniques to manufacture meat and meat products. As used herein, in vitro meat and meat products includes animal protein products as well as non-meat products including soluble forms and solid forms in whole cell or hydrolyzed format. While still in an early stage of development, in vitro meat and meat products may offer a number of advantages over traditional meat products such as health and environmental advantages, and benefits to animal welfare. It is a next-generation and emerging technology that operates as part of a wider field of cellular agriculture, or the production of agricultural products from cell cultures.

Cells for the production of in vitro meat may be cells (e.g., muscle cells, somatic cells, stem cells, etc.) taken from animal biopsies, which may then be grown separately from the animal in culture media in a bioreactor or other type of sterile environment. The cells may grow into a semi-solid or solid form mimicking an animal organ by attaching to an edible three-dimensional scaffold that is placed in the bioreactor. Yet, the cells may also grow in suspension culture. The starter cells may be primary cells directly obtained from the animal's tissues, or continuous cell lines. If grown under the right conditions in appropriate culture media, primary cells will grow and proliferate, but only a finite number of times that is related to the telomere length at the end of the cell's DNA. Continuous cell lines, on the other hand, can be cultured in vitro over an extended period. Cell biology research has established procedures on how to convert primary cells into immortal continuous cell lines. Primary cells may be transformed into continuous cell lines using viral oncogenes, chemical treatments, or overexpression of telomerase reverse transcriptase to prevent the telomeres from shortening.

SUMMARY

While existing methods as mentioned in the background may fulfil certain requirements, for example, the recombinant method avoids animal scarification and the spent/conditioned medium method may provide a derived raw materials with more comprehensive trace components in relatively low cost compared to wild animals or wild plants harvesting method. However, none of the existing methods fulfill the growing demand of sustainability, low cost, whole cell components, complete cell protein/peptide portfolio and cruelty-free in one simple solution.

Of the many aspect of the invention, therefore, is comprising substantially all protein polypeptides and/or polypeptide fragments derived from substantially all the proteins in a cell from an in vitro cell culture; and (ii) free of wastes and metabolites from the culture media used in the in vitro cell culture.

It is an objective of the present invention to provide an alternative method of obtaining animal-derived raw materials and plant-derived raw materials using in vitro meat production and in vitro plant production respectively. The derived raw materials according to the present invention are free of environmental contaminants, adventitious agents and allergens. It also helps to limit animal suffering and sacrifice associated with the production of animal-derived materials.

Cell hydrolysate composition of the present invention may be applied as an active ingredient in dietary supplements, hair care, skincare, wound care, cosmetic or food products. Cell hydrolysate includes but is not limited to hyaluronic acid. The cell hydrolysate composition of the present invention comprises all protein polypeptides and/or protein polypeptides fragments derived thereof from whole cell. In other words, the composition comprises multiple protein polypeptides and/or protein polypeptides fragments derived thereof instead of a single protein polypeptide. As such, the composition of the present invention is multifunctional. Given the foregoing, it is further an objective of the present invention to provide a cell hydrolysate composition through an efficient and environmentally friendly process. The protein hydrolysate composition of the present invention also provides improved batch-to-batch consistency and traceability for such composition. Some protein polypeptides can only be found in animal but not plants, vice versa. For example, collagen can only be found in animal cell but not plant cell. Generally, animal derived protein polypeptides have high efficacy to human than plant derived protein polypeptides do.

It is also an objective of the present invention to create further values for consumers or manufacturers in various industries/products, including but not limited to the dietary supplements, hair care, skincare, wound care, cosmetic, food products, supplements, drugs and other medicinal applications, as it simultaneously solves all drawbacks encountered by the conventional derived raw material creation method (i.e. extracting from wild animals/plants, recombinant DNA organisms and conditioned/spent medium). The present invention provides the following benefits:
  (1) no reliance on animal and/or plant sources;
  (2) no reliance on genetically modified organisms;
  (3) the capture of all functional proteins naturally produced by the subject cells;
  (4) Purity (no waste in the product);
  (5) No use of harmful chemicals;
  (6) simple downstream process, thereby lowering the cost; and
  (7) multi-functional instead of single-use/function/action.

The benefits of the present invention lead to the creation of new values that meet consumers' needs. It provides active ingredient of various products or the products itself (includes but not limited to dietary supplements, hair care, skincare, wound care, cosmetic, food products, supplements, drugs and other medicinal applications) the following characteristics:
  (1) clean label due to the high purity and non-existence of waste or harmful chemicals in the derived raw materials;
  (2) sustainability due to little or low reliance on animal and/or plant sources;
  (3) non-chemical synthesis due to the use of biomaterials;
  (4) multi-functional due to its complete molecular profile with all functional proteins naturally produced by the subject cells; and
  (5) backed by scientific principles and test results.

According to some embodiments of the present invention, a cell hydrolysate composition, the composition comprising (i) a mixture of protein polypeptides and/or polypeptide fragments derived from collagen 1 α1; (ii) a mixture of protein polypeptides and/or polypeptide fragments derived from collagen 1 β1; (iii) a mixture of protein polypeptides and/or polypeptide fragments derived from connective tissue growth factor (CTFG); and (iv) a mixture of protein polypeptides and/or polypeptide fragments derived from Decorin.

BRIEF DESCRIPTION OF THE DRAWINGS

The disclosure may be better understood by reference to the detailed description when considered in connection with the accompanying drawings. The components in the figures are not necessarily to scale, emphasis instead being placed upon illustrating the principles of the disclosure.

DETAILED DESCRIPTION

Figure 1:
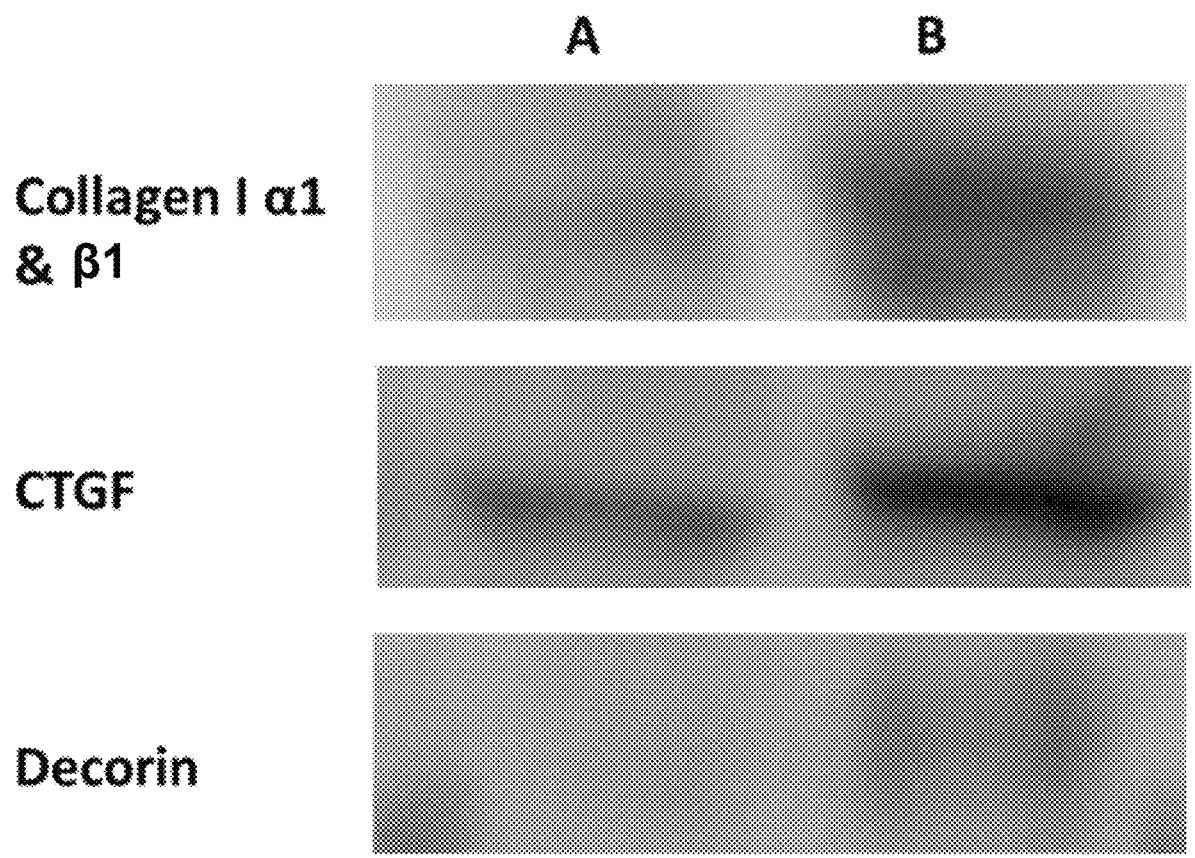
FIG. 1 shows western blot analysis of proteins in a yellow croaker swim bladder tissue (labeled as A) and a yellow croaker swim bladder cell line (labeled as B).

Generating Cell Hydrolysate by In Vitro Cell Culture

The method of producing cell hydrolysate (i.e. animal-derived raw materials or plant-derived raw materials) from in vitro cell culture of the present invention offers a lot of benefits compared to those created from wild animals or plants.

First, since the cells are grown under contaminant-free and disease-free conditions, the culture medium does not contain environmental contaminants (heavy metal, antibiotics, micro plastics, herbicides, fungicides, insecticides) or adventitious agents (bacteria, viruses, fungi, transmissible spongiform encephalopathy agents). As a result, the animal-derived raw materials or plant-derived raw materials generated will be also contaminant-free and disease-free.

Second, an animal-component-free and chemically defined medium may be used to reduce the chance of triggering an allergic reaction of the user. This is achieved by substituting animal serum and animal-derived growth factors (e.g. bovine insulin) in the medium by recombinant growth factors. Plant extract/hydrolysate is not required in a chemically defined medium.

Third, the batch-to-batch consistency of the animal-derived raw materials or plant-derived raw materials may be significantly improved. This is because the nutritional profile (carbohydrates, amino acids, vitamins, minerals) of the basal medium is known and consistent and may be further refined using a chemically defined medium, i.e. a medium with known concentrations of all nutrients and growth factors.

Fourth, enhance traceability. Since the supply chain for every culture medium component is known, everything could be easily traced back to the origin.

Fifth, reduce animal suffering and sacrifice. Running the production process does not require a continuous supply of animal tissues from wild animals. Initially, the starter cells are purified from a small piece of animal tissue and developed into a cell line, which can be cryopreserved and propagated indefinitely in a culture medium. This limits animal suffering and sacrifice.

Sixth, reduce waste and enhance efficiency. Nutrients in the medium are directly supplied to cells for cell growth. Every cultivated cell is lysed to produce the cell hydrolysate. There is no waste of energy and nutrients for the growth of unused animal/plant parts, or life processes such as animal mating and locomotion.

Further, the present invention creates values for consumers or manufacturers of various industries/products, including but not limited to dietary supplements, hair care, skincare, wound care, cosmetic, food products, supplements, drugs and other medicinal applications, since it addresses all the drawbacks encountered in the conventional methods as mentioned in the background section. The present invention provides the following benefits: animal-derived raw materials and/or plant-derived raw materials from the products generated by in vitro meat production of the present invention offer a lot of benefits compared to those created from wild animals or plants.

First, it does not rely on a continuous feed of animal sources. For example, to produce more collagen-based cream via the conventional method, more animal body parts are needed which can result in more animal suffering or sacrifice. In the present invention, starter cells (not limited to stem cells, muscle cells, fibroblast cells. adipocytes) are purified from a small piece of animal tissue and established into a cell line. The cell line can be cryopreserved and stored in liquid nitrogen. When needed, the cell line can be thawed and propagated indefinitely under cell culture conditions to produce active ingredients (e.g. growth factors, ECM molecules). Therefore, the entire process is self-sustainable and causes little animal suffering/sacrifice.

Second, it does not rely on the animal source. In the present invention, starter cells (not limited to stem cells, muscle cells, fibroblast cells. adipocytes) are purified from a small piece of animal tissue and established into a cell line. The cell line is not genetically modified.

Third, the derived raw materials of the present invention are multi-functional because it includes a lot of trace amount of functional proteins in addition to the key target protein. Such a trace amount of functional proteins may be essential for many cellular functions. A product created from derived raw materials with a functional protein profile closer to an extracted wild animal/plant part generally provides better performance than a product created from derived raw materials with a less complete functional protein profile. Even though functional proteins can be added into the derived raw materials through external replenishments, it is difficult to replenish a number of functional proteins. Also, the cost increases with the number of replenishments.

Fourth, the functional proteins created by the present invention do not contain waste since the ingredient in the growth medium is well controlled.

Fifth, the derived raw material created by the present invention does not contain harmful chemicals as the functional proteins are not extracted using harmful chemicals. The ingredient in the growth medium is well controlled.

Sixth, the functional proteins created by the present invention do not contain wastes and harmful chemicals, therefore, there is no need to further isolated and purified. Therefore, the production cost can be lower.

The benefits of the present invention allow the creation of new values that meet consumers' needs. It provides active ingredient of various product or the products itself (including but not limited to dietary supplements, hair care, skincare, wound care, cosmetic, food products, supplements, drugs and other medicinal applications) the following characteristics:

(1) clean label due to the high purity and non-existence of waste or harmful chemicals in the derived raw materials;
(2) sustainability due to little or low reliance on animal and/or plant sources;
(3) non-chemical synthesis due to the use of biomaterials;
(4) multi-functional due to its complete molecular profile with all functional proteins naturally produced by the subject cells; and
(5) backed by scientific principles and test results.

As an example, FIG. 1 shows western blot analysis of proteins in a yellow croaker swim bladder tissue (labeled as A) and a yellow croaker swim bladder cell line (labeled as B). It illustrates that in vitro cultured cells contain similar proteins as the original tissue obtained from an animal. Therefore, it shows that the foregoing benefits can be fully realized by the present invention.

The method of producing cell hydrolysate composition from in vitro cell culture involves the steps of harvesting the cells from in vitro cell culture ("Harvesting Step"), lysing the harvested cells to release all the protein polypeptides from the harvested cells ("Lysing Step") and an optional digestion step the protein polypeptides from the lysing step are cut/cleaved ("Digestion Step"). In particular, the harvesting step may comprise the steps of separating the cells in the in vitro cell culture from the cell culture medium, which may further comprise the step of removing the cells from the in vitro cell culture container and/or the step of isolating the cells. The isolation may involve centrifugation to separate the cells from the cell culture medium and/or filtration to separate the cells from the cell culture medium. In some embodiments, membrane having pore size ranged from 5 µm to 60 µm may be used. The lysing step may further comprise lysing the cells by using mechanical means including but not limited to sonication, high pressure homogenizer, manual grinding and/or freeze/thaw cycles. Non-mechanical means may also be used to lyse the cells, including but not limited heating, osmotic shock, cavitation, alkali and/or detergent(s), acid hydrolysis and/or enzyme(s). For the optional digestion step, different enzyme(s) or chemical reagent(s) may be used, including but not limited to, subtilisin, chymotrypsin, Trypsin, carboxypeptidase, elastase, pepsin, proteinase K and/or cyanogen bromide.

The composition obtained from the foregoing method may be applied as a topical agent to dietary supplements, hair care, skincare, cosmetic, and wound care products. The hydrolysate may also be used as an active ingredient in various products, including but not limited to, dietary supplements, hair care, skincare, wound care, cosmetic, food products, supplements, drugs and other medicinal applications.

Figure 2:
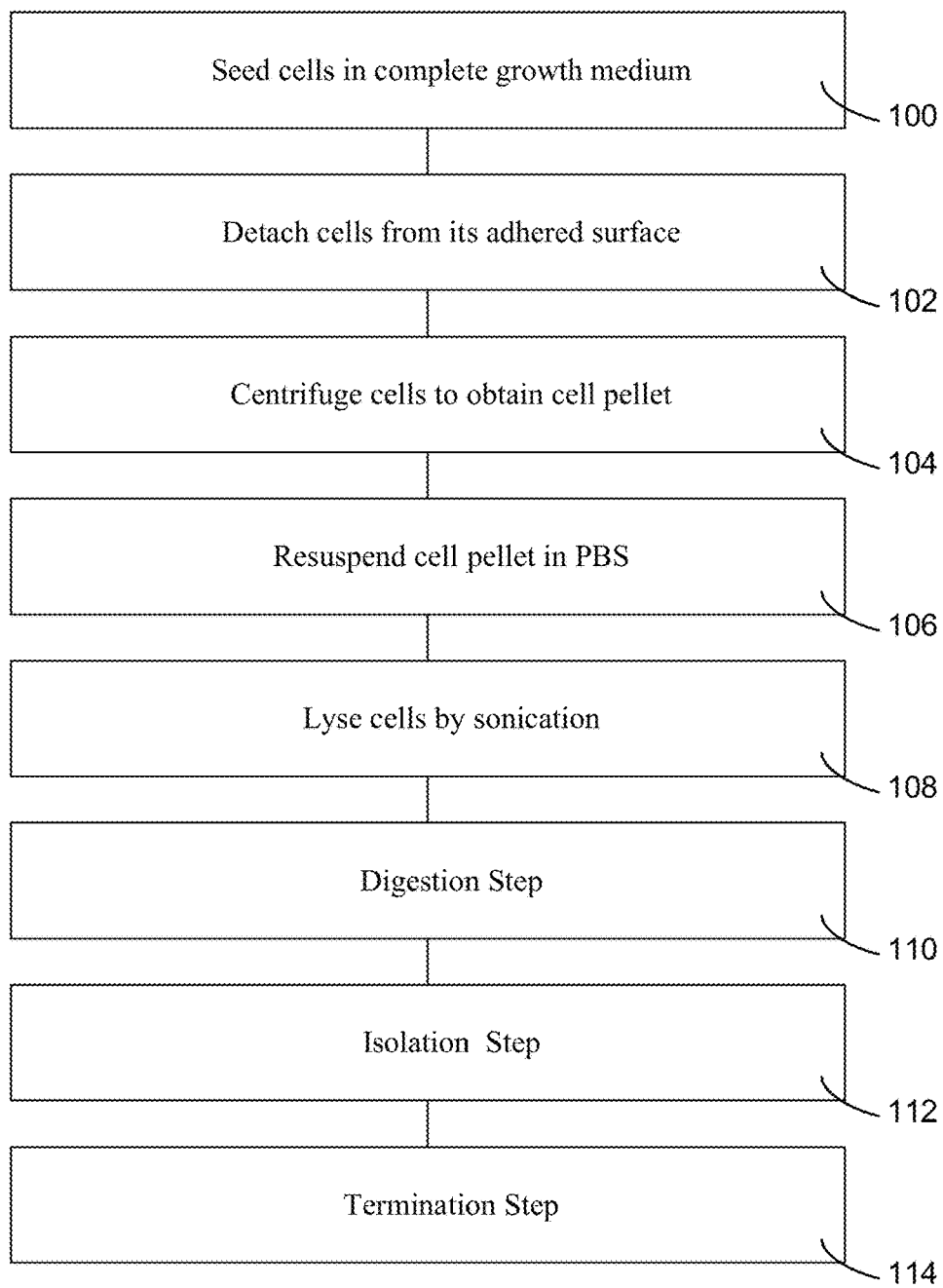
FIG. 2 is a flowchart of a method for generating cell hydrolysate from in vitro cell culture, according to some embodiments of the present disclosure.

Referring now to the drawings, and with specific reference to FIG. 2, a method of producing cell hydrolysate from in vitro cell culture in one embodiment. In cell growing step 100, cells are first grown under controlled conditions using a culture medium which is either partially defined (i.e. defined basal medium supplemented with FBS/plant hydrolysates/human platelet lysate) or a chemically defined medium (i.e. medium having defined concentrations of all nutrients and growth factors) that is devoid of animal or plant components. In yet some embodiments, at least one cell line may be used in the cell growing step 100. In some embodiments, the cell lines include stem cells, muscle cells, fibroblast cells, and adipocytes. In yet one specific embodiment, cultivated fish swim bladder cells are used in the cell growing step 100.

In detaching step 102, the cells are detached from its adhered surface and collect cell suspension into a tube.

In some embodiments, detaching step 102 may be skipped if the cells are collected from in vitro suspension cell culture.

The mix obtained from the detaching step 102 is then centrifuged ranged between 100×g to 500×g for 1-10 minutes in the centrifuging step 104, preferably 300×g for 5 minutes. The supernatant is removed and cell pellet is obtained. In some embodiment, the cell pellet may be re-suspended in medium and perform the centrifuging step 104 more than once. In some embodiments, other speed and time may be used for the centrifugation.

In the resuspension step 106, the cell pellet is suspended in PBS at a predetermined volume. In some embodiments, the cell pellet is suspended in 1 ml PBS. In some embodiments, the cell pellet can be suspended in buffer or saline other than PBS, for example, Hank's balanced salt solution.

In lysis step 108, the cells from step 106 are lysed by sonication.

Following cell lysis by sonication, the soluble fraction is isolated from the cell debris. Proteins in the soluble fraction are enzymatically digested into short functional peptides in digestion step 110. The desired protease of choice is added to the soluble fraction at a temperature ranged from 25° C. to 40° C. for 1-5 hours, preferably 30° C. for 2 hours. In some embodiments, the protease is pepsin, proteinase K or trypsin, preferably Proteinase K or Trypsin. Peptides having varies molecular size are obtained. In some embodiments, peptides having a molecular size ranged from 100 Daltons (Da)) to 800 Da are favored. Preferably peptides having a molecular size smaller than 500 Da is preferred because molecules having a molecular size greater than 500 Daltons (Da) do not effectively penetrate through the outermost epidermis and be absorbed by the underlying skin layers. In yet some other embodiments, peptides having a molecular size ranged from 100 Daltons (Da) to 500 Da is preferred. In some embodiments, an appropriate amount of protease is added to the cell suspension to break down cellular proteins into smaller peptides. Perform the digestion for 1-3 hours, preferably 2 hours, and keep the tube inside a temperature ranged from 25° C. to 40° C. water bath, preferably 30° C.

After the digestion step 110, the mix from digestion step 110 is then centrifuged ranged at 15000×g to 25000×g for 15-35 minutes in the isolation step 112 to clarify the liquid and removing any large debris, preferably 15000×g for 20 minutes. In some embodiments, the isolation step 112 may be performed by filtering the mix from digestion step 110. In some embodiments, membrane having pore size ranged from 0.05 µm to 0.5 µm may be used. The supernatants from the micro centrifuge tubes are combined into a tube, preferably a 50 ml tube. Avoid disturbing the pellets in the micro centrifuge tubes.

In the termination step 114, the enzyme digestion activity is stopped by heating and/or dilution. In some embodiments, the termination step 114 may perform before the isolation step 112.

If the hydrolysate is not used immediately, in some embodiments, store it at a temperature ranged from +4 to −30 degrees Celsius, preferably −10 degree Celsius.

Cell Hydrolysate Compositions

A cell hydrolysate composition, the composition comprising substantially all protein polypeptides and/or polypeptide fragments derived from substantially all the proteins in a cell from an in vitro cell culture; and (ii) substantially free of wastes and metabolites from the culture media used in the in vitro cell culture comprising at least one of, including but not limited to, ammonia, lactate, pyruvate and putrescine. In some embodiments, the composition is substantially free of wastes and metabolites from the culture media used in the in vitro cell culture comprising all of the ammonia, lactate, pyruvate and putrescine. The polypeptides and/or polypeptide fragments may range in size from about 100 Daltons (Da) to about 800 Da. In some embodiments, the average molecular size of the polypeptides and/or polypeptide fragments may be less than about 500 Da. In other embodiments, the average molecular size of the polypeptides and/or polypeptide fragments ranged from about 100 Da to about 500 Da. The cell hydrolysate compositions may be stored at a refrigerated temperature (i.e., +4° C. to −30° C.). In one embodiment, the cell hydrolysate composition may be stable for about one week to about four weeks. In another embodiment, the cell hydrolysate composition may be stable for about one month to about six months. In a further embodiment, the cell hydrolysate composition may be stable for more than about six months.

The cell hydrolysate composition may be dried. For example the cell hydrolysate composition may be freeze dried, vacuum dried or air dried. The temperature for drying is preferably less than 150° C.

In some embodiments, the protein polypeptides and/or polypeptide fragments are derived from at least one animal cell culture. In other embodiments, the protein polypeptides and/or polypeptide fragments are derived from at least one plant cell culture. In some embodiments, the protein polypeptides and/or polypeptide fragments are derived from a combination of animal cell culture and plant cell culture. In yet some embodiments, the protein polypeptides and/or polypeptide fragments are derived from yellow croaker swim bladder cell line. In some embodiments, the protein polypeptides and/or polypeptide fragments are derived from mutated cell cultures (both animals or plants). In some embodiments, the protein polypeptides and/or polypeptide fragments are derived from mutated or non-mutated human cell culture.

In some embodiments, the cell hydrolysate composition further comprises Lumican, Fibulin, Chondroitin, Chitosan, Glycosaminoglycan (chondroitin and heparan), Chondroadherin and Tropomyosin, etc.

In some embodiments, a cell hydrolysate composition comprises (i) a mixture of protein polypeptides and/or polypeptide fragments derived from collagen 1 α1; (ii) a mixture of protein polypeptides and/or polypeptide fragments derived from collagen 1 β1; (iii) a mixture of protein polypeptides and/or polypeptide fragments derived from connective tissue growth factor (CTFG); and (iv) a mixture of protein polypeptides and/or polypeptide fragments derived from Decorin.

In yet some embodiments, the protein polypeptides and/or polypeptide fragments are derived from yellow croaker swim bladder cell line from an in vitro cell culture. In yet some embodiments, the protein polypeptides and/or polypeptide fragment are derived from yellow croaker swim bladder cell line from an in vitro cell culture and at least one animal cell line and/or plant cell line from an in vitro cell culture. In some embodiments, the protein polypeptides and/or polypeptide fragments are derived from mutated cell cultures (both animals or plants). In some embodiments, the protein polypeptides and/or polypeptide fragments are derived from mutated or non-mutated human cell culture.

In some embodiments, the composition is substantially free of wastes and metabolites comprising at least one of, but not limited to ammonia, lactate, pyruvate and putrescine. In some embodiments, the composition is substantially free of wastes and metabolites comprising all of ammonia, lactate, pyruvate and putrescine.

In some embodiments, the protein polypeptides and/or polypeptide fragments are derived from yellow croaker swim bladder cell line from an in vitro cell culture and enzymatically digested by Trypsin. In some embodiments, (i) the mixture of polypeptides and/or polypeptide fragments derived from collagen 1 α1 comprises at least 1 polypeptide fragment selected from the group consisting of SEQ ID: 1-112; (ii) a mixture of polypeptides and/or polypeptide fragments derived from collagen 1 β1 comprises at least 1 polypeptide fragment selected from the group consisting of SEQ ID: 113-214; (iii) a mixture of polypeptides and/or polypeptide fragments derived from CTFG comprises at least 1 polypeptide fragment selected from the group consisting of SEQ ID: 215-249; and (iv) a mixture of polypeptides and/or polypeptide fragments derived from Decorin comprises at least 1 polypeptide fragment selected from the group consisting of SEQ ID: 250-285.

In some embodiments, the protein polypeptides and/or polypeptide fragments are derived from yellow croaker swim bladder cell line from an in vitro cell culture and enzymatically digested by Trypsin. In some embodiments, (i) the mixture of polypeptides and/or polypeptide fragments derived from collagen 1 α1 comprises at least 56 polypeptide fragments selected from the group consisting of SEQ ID: 1-112; (ii) a mixture of polypeptides and/or polypeptide fragments derived from collagen 1 β1 comprises at least 51 polypeptide fragments selected from the group consisting of SEQ ID: 113-214; (iii) a mixture of polypeptides and/or polypeptide fragments derived from CTFG comprises at least 17 polypeptide fragments selected from the group consisting of SEQ ID: 215-249; and (iv) a mixture of polypeptides and/or polypeptide fragments derived from Decorin comprises at least 18 polypeptide fragments selected from the group consisting of SEQ ID: 250-285.

In some embodiments, (i) the mixture of polypeptides and/or polypeptide fragments derived from collagen 1 α1 comprises substantially all of the polypeptide fragments selected from the group consisting of SEQ ID: 1-112; (ii) a mixture of polypeptides and/or polypeptide fragments derived from collagen 1 β1 comprises substantially all of the polypeptide fragments selected from the group consisting of SEQ ID: 113-214; (iii) a mixture of polypeptides and/or polypeptide fragments derived from CTFG comprises substantially all of the polypeptide fragments selected from the group consisting of SEQ ID: 215-249; and (iv) a mixture of polypeptides and/or polypeptide fragments derived from Decorin substantially all of the polypeptide fragments selected from the group consisting of SEQ ID: 250-285.

In some embodiments, the protein polypeptides and/or polypeptide fragments are derived from yellow croaker swim bladder cell line from an in vitro cell culture and enzymatically digested by Proteinase K. In some embodiments, (i) the mixture of polypeptides and/or polypeptide fragments derived from collagen 1 α1 comprises at least 1 polypeptide fragment selected from the group consisting of SEQ ID: 286-488; (ii) a mixture of polypeptides and/or polypeptide fragments derived from collagen 1 β1 comprises at least 1 polypeptide fragment selected from the group consisting of SEQ ID: 489-657; (iii) a mixture of polypeptides and/or polypeptide fragments derived from CTFG comprises at least 1 polypeptide fragment selected from the group consisting of SEQ ID: 658-722; and (iv) a mixture of polypeptides and/or polypeptide fragments derived from Decorin comprises at least 1 polypeptide fragment selected from the group consisting of SEQ ID: 723-809.

In some embodiments, the protein polypeptides and/or polypeptide fragments are derived from yellow croaker swim bladder cell line from an in vitro cell culture and enzymatically digested by Proteinase K. In some embodiments, (i) the mixture of polypeptides and/or polypeptide fragments derived from collagen 1 α1 comprises at least 101 polypeptide fragments selected from the group consisting of SEQ ID: 286-488; (ii) a mixture of polypeptides and/or polypeptide fragments derived from collagen 1 β1 comprises at least 84 polypeptide fragments selected from the group consisting of SEQ ID: 489-657; (iii) a mixture of polypeptides and/or polypeptide fragments derived from CTFG comprises at least 32 polypeptide fragments selected from the group consisting of SEQ ID: 658-722; and (iv) a mixture of polypeptides and/or polypeptide fragments derived from Decorin comprises at least 43 polypeptide fragments selected from the group consisting of SEQ ID: 723-809.

In some embodiments, (i) the mixture of polypeptides and/or polypeptide fragments derived from collagen 1 α1 comprises substantially all of the polypeptide fragments selected from the group consisting of SEQ ID: 286-488; (ii) a mixture of polypeptides and/or polypeptide fragments derived from collagen 1 β1 comprises substantially all of the polypeptide fragments selected from the group consisting of SEQ ID: 489-657; (iii) a mixture of polypeptides and/or polypeptide fragments derived from CTFG comprises substantially all of the polypeptide fragments selected from the group consisting of SEQ ID: 658-722; and (iv) a mixture of polypeptides and/or polypeptide fragments derived from Decorin substantially all of the polypeptide fragments selected from the group consisting of SEQ ID: 723-809.

In some embodiments, the cell hydrolysate composition further comprises Lumican, Fibulin, Chondroitin, Chitosan, Glycosaminoglycan (chondroitin and heparan), Chondroadherin and Tropomyosin, etc.

Additionally, the invention also encompasses polypeptide fragments that are substantially similar in sequence to those selected from the group consisting of SEQ ID NOs: 1-809. In one embodiment, polypeptide fragment may have at least 80% sequence identity to a polypeptide fragment selected from the group consisting of SEQ ID NOs: 1-809. In another embodiment, the polypeptide fragment may have at least 90% sequence identity to a polypeptide fragment selected from the group consisting of SEQ ID NOs: 1-809.

It is also envisioned that the cell hydrolysate compositions of the invention may further comprise a non-hydrolyzed (i.e., intact) protein. The non-hydrolyzed protein may be present in an essentially intact preparation. Furthermore, the non-hydrolyzed protein may be isolated from a plant in vitro culture or isolated from an animal in vitro culture. The relative proportions of the protein hydrolysate and the non-hydrolyzed protein may vary depending on the application of the cell hydrolysate composition.

The multiple protein polypeptides, protein polypeptide fragments and/or other ingredients in the cell from the in vitro cell culture contained in the cell hydrolysate composition provide synergistic effects and benefits in varies applications including but not limited to promoting general health, hair health, skin health, wound healing, joint health and collagen regulation and cartilage development.

In some embodiments, the cell hydrolysate composition has a pH ranged from 6.5-8.5. In yet some embodiments, the cell hydrolysate composition is water soluble. Yet in some embodiments, the color of the cell hydrolysate composition is ranged from colorless to pale yellow.

Products Comprising the Cell Hydrolysate Composition

The cell hydrolysate composition of the present invention may be applied as a topical agent to dietary supplements, hair care, skincare, cosmetic, and wound care products. The hydrolysate may also be used as an active ingredient in various products, including but not limited to, dietary supplements, hair care, skincare, wound care, cosmetic, food products, supplements, drugs and other medicinal applications.

Yet another aspect of the present invention, a pharmaceutical composition comprising the cell hydrolysate composition; and a pharmaceutical acceptable carrier.

For the dietary supplements, hair care, skincare, wound care, cosmetic or topical product, the hydrolysate from cultivated cells is rich in nutrients, contains multiple protein polypeptides and/or polypeptides fragments that stimulate skin cell repair and regeneration, and have a molecular size smaller than 500 Daltons (Da). The hydrolysate of the present invention can reach and take effect on the deep skin layers (dermis, hypodermis) as the hydrolysate of the present invention is small enough to pass through the stratum corneum and also maintains the key protein domains of growth factors and cytokines to elicit their functional activities.

Figure 3A:
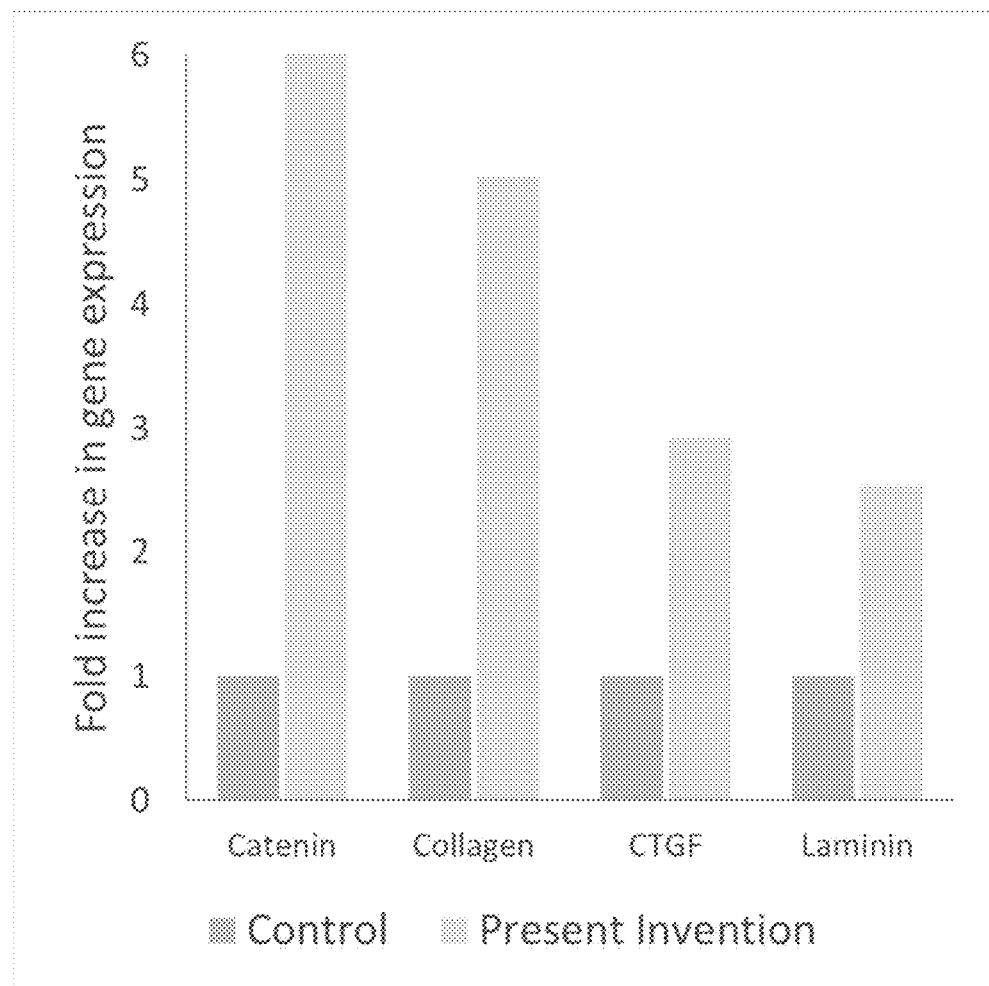
FIG. 3A is a chart depicting gene expression upon exposure to the hydrolysate in regeneration circumstance.

Referring to FIG. 3A, the chart illustrates the difference in gene expression between skin cells being treated with cell hydrolysate composition and skin cells not being treated with cell hydrolysate in regeneration circumstance. It shows that the cell hydrolysate composition of the present invention boosts healthy protein metabolisms of the skin, increases collagen production, strengthens skin microstructure, revitalizes healthy complexion and skin tone from the inside out, and maintains skin and hair follicle integrity.

Figure 3B:
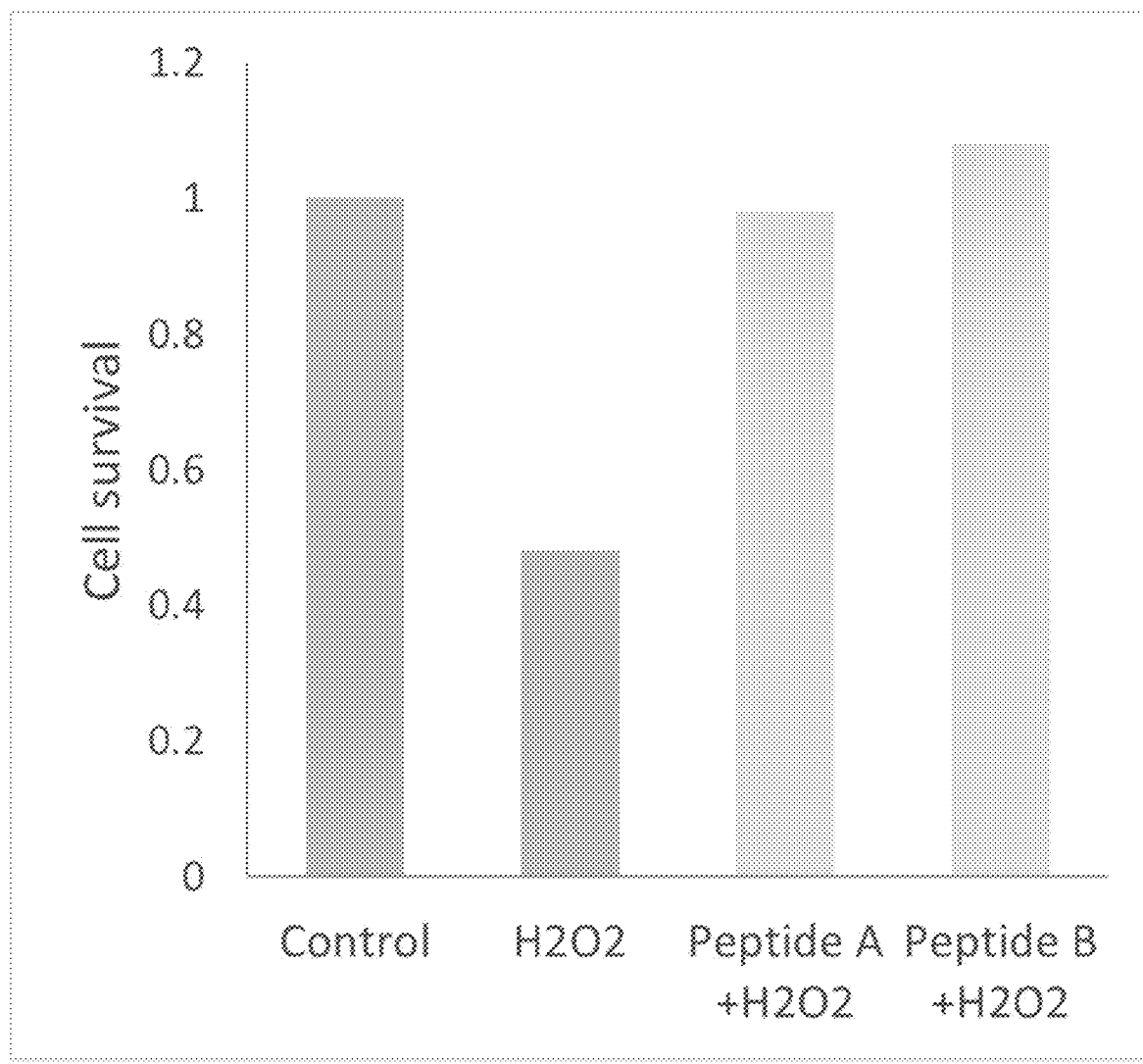
FIG. 3B is a chart depicting cell survival upon exposure to the hydrolysate in anti-oxidant circumstance.

Referring to FIG. 3B, the chart illustrates the difference in cell survival between skin cells being treated with cell hydrolysate composition (Peptide A means cell hydrolysate composition of the present invention comprising SEQ ID: 286-809; and Peptide B means cell hydrolysate composition of the present invention comprising SEQ ID: 1-285) and skin cells not being treated with cell hydrolysate in antioxidant circumstance (in this specific example, under hydrogen peroxide circumstance). It shows that the cell hydrolysate compositions of the present invention, especially Peptide B, promotes the cell's own antioxidant defense, helps to protect the cells from harmful environmental irritants and pollutants, which cause premature skin aging, and increases skin cell survival from oxidative stress.

Figure 3C:
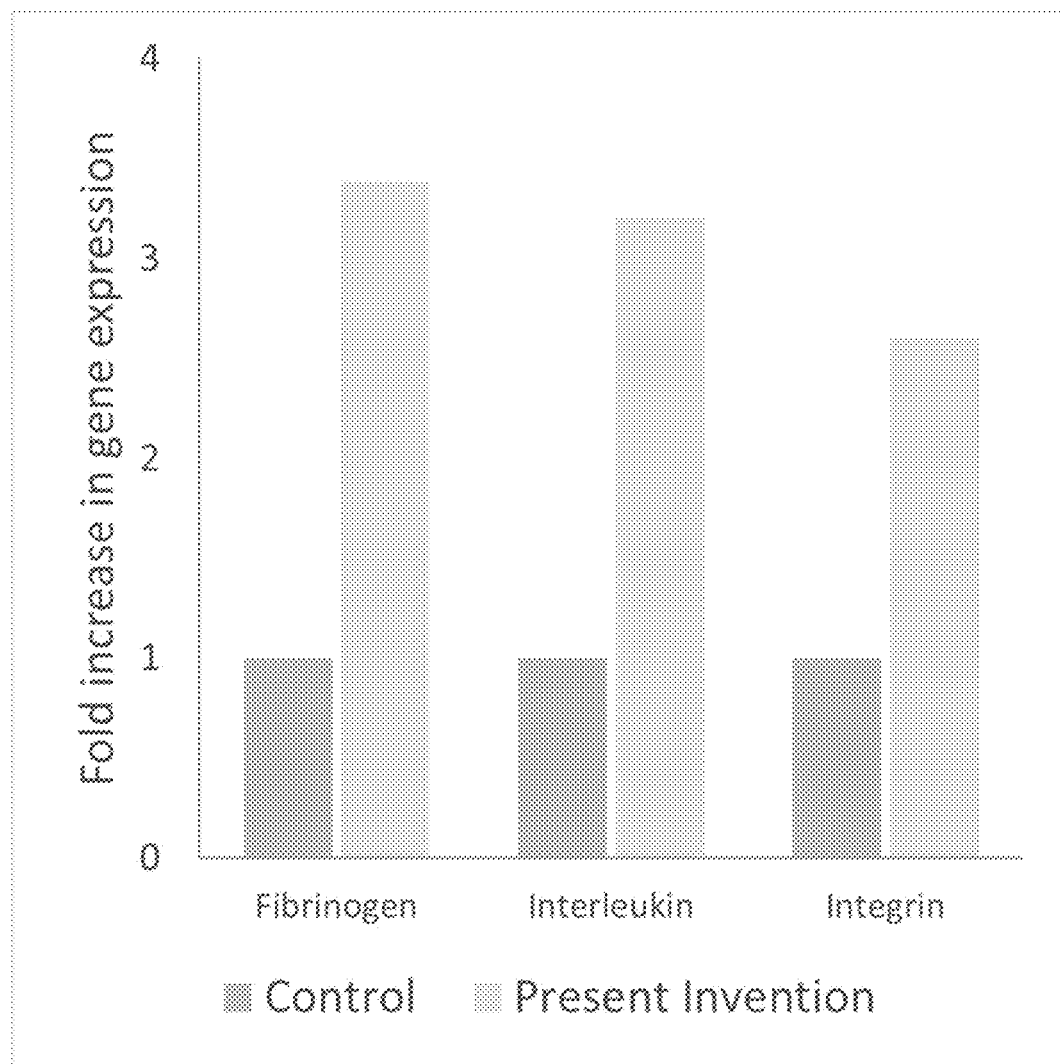
FIG. 3C is a chart depicting gene expression upon exposure to the hydrolysate in skin repair circumstance.

Referring to FIG. 3C, the chart illustrates the difference in gene expression between skin cells being treated with cell hydrolysate and skin cells not being treated with cell hydrolysate in skin repairing circumstance. It shows that the cell hydrolysate composition of the present invention strengthens skin barrier that protects the body from dehydration or trauma, repairs damage skin and prevents premature aging, and improves overall skin health for a youthful appearance.

The above description is illustrative and is not restrictive. Many variations of embodiments may become apparent to those skilled in the art upon review of the disclosure. The scope embodiments should, therefore, be determined not with reference to the above description, but instead should be determined with reference to the pending claims along with their full scope or equivalents.

One or more features from any embodiment may be combined with one or more features of any other embodiment without departing from the scope embodiments. A recitation of "a", "an" or "the" is intended to mean "one or more" unless specifically indicated to the contrary. Recitation of "and/or" is intended to represent the most inclusive sense of the term unless specifically indicated to the contrary.

While the present disclosure may be embodied in many different forms, the drawings and discussion are presented with the understanding that the present disclosure is an exemplification of the principles of one or more inventions and is not intended to limit anyone embodiment to the embodiments illustrated.

The disclosure, in its broader aspects, is therefore not limited to the specific details, representative system and methods, and illustrative examples shown and described above. Various modifications and variations may be made to the above specification without departing from the scope or spirit of the present disclosure, and it is intended that the present disclosure covers all such modifications and variations provided they come within the scope of the following claims and their equivalents.

What is claimed is:

1. A controlled process of producing an artificially generated cell hydrolysate composition from an in vitro cell culture comprising the steps of:
   - obtaining the artificially generated cell hydrolysate composition from the in vitro cell culture, comprising the steps:
     - (i) harvesting the cells from in vitro cell culture;
     - (ii) lysing the harvested cells to release all the protein polypeptides from the harvested cells;
     - (iii) optionally cutting or cleaving the protein polypeptides from the lysing step, wherein the harvesting step further comprises the step of isolating the cells from cell culture medium through centrifugation or filtration,
   - wherein the lysing step further comprises at least one of the following: sonication, high pressure homogenizer, manual grinding, freeze/thaw cycles, heating, osmotic shock, cavitation, alkali, detergent(s), acid, enzyme(s) and/or chemical reagent(s);
   - wherein the enzyme(s) or chemical reagent(s) comprises at least one of subtilisin, chymotrypsin, trypsin, carboxypeptidase, elastase, pepsin, proteinase K and/or cyanogen bromide; and
   - further comprises obtaining non-hydrolyzed proteins from a plurality of cells, harvesting the cell hydrolysate from the in vitro cell culture upon lysis, and obtaining the protein polypeptides in the artificially generated cell hydrolysate composition with a purity higher than that in a cell hydrolysate obtained from an animal tissue or a plant tissue.

2. The controlled process of claim 1, wherein the cutting or cleaving of the protein polypeptide is performed by proteinase K.

3. The controlled process of claim 1, wherein the cutting or cleaving the protein polypeptide is performed by trypsin.

4. The controlled process of claim 1, wherein the artificially generated cell hydrolysate composition comprises one or more of a mixture of protein polypeptides and/or polypeptide fragments from the group consisting of lumican, tropomyosin, chondroadherin and fibulin.

5. The controlled process of claim 1, wherein the artificially generated cell hydrolysate composition comprises:
   - (i) the mixture of polypeptides and/or polypeptide fragments from collagen 1 α1 comprises at least 101 polypeptide fragments selected from the group consisting of SEQ ID NOs: 286-488;
   - (ii) a mixture of polypeptides and/or polypeptide fragments from collagen 1 β1 comprises at least 84 polypeptide fragments selected from the group consisting of SEQ ID NOs: 489-657;
   - (i ii) a mixture of polypeptides and/or polypeptide fragments from connective tissue growth factor (CTGF) comprises at least 32 polypeptide fragments selected from the group consisting of SEQ ID NOs: 658-722; and
   - (iv) a mixture of polypeptides and/or polypeptide fragments from Decorin comprises at least 43 polypeptide fragments selected from the group consisting of SEQ ID NOs: 723-809.

* * * * *

```
                         SEQUENCE LISTING

<160> NUMBER OF SEQ ID NOS: 809

<210> SEQ ID NO 1
<211> LENGTH: 59
<212> TYPE: PRT
<213> ORGANISM: Yellow Croaker

<400> SEQUENCE: 1

Asp Val Trp Lys Pro Glu Pro Cys Gln Ile Cys Val Cys Asp Ser Gly
1               5                   10                  15

Thr Val Met Cys Asp Glu Val Ile Cys Glu Asp Thr Thr Asp Cys Pro
            20                  25                  30

Asn Pro Val Ile Pro His Asp Glu Cys Cys Pro Val Cys Pro Asp Asp
        35                  40                  45

Gly Phe Gln Glu Pro Gln Val Glu Gly Pro Lys
    50                  55

<210> SEQ ID NO 2
<211> LENGTH: 44
<212> TYPE: PRT
<213> ORGANISM: Yellow Croaker

<400> SEQUENCE: 2

Gly Pro Ala Gly Pro Pro Gly Asn Asp Gly Ile Pro Gly Gln Pro Gly
1               5                   10                  15

Met Pro Gly Pro Pro Gly Pro Pro Gly Pro Pro Gly Leu Gly Gly Asn
            20                  25                  30

Phe Ser Pro Gln Met Ser Gly Gly Tyr Asp Asp Lys
        35                  40

<210> SEQ ID NO 3
<211> LENGTH: 45
<212> TYPE: PRT
<213> ORGANISM: Yellow Croaker

<400> SEQUENCE: 3

Gly Glu Gln Gly Pro Ala Gly Gly Pro Gly Phe Gln Gly Leu Pro Gly
1               5                   10                  15

Pro Gln Gly Ala Val Gly Glu Thr Gly Lys Pro Gly Glu Gln Gly Leu
            20                  25                  30

Pro Gly Glu Ala Gly Ala Pro Gly Pro Ala Gly Ser Arg
        35                  40                  45

<210> SEQ ID NO 4
<211> LENGTH: 34
<212> TYPE: PRT
<213> ORGANISM: Yellow Croaker

<400> SEQUENCE: 4
```

```
His Val Trp Phe Gly Glu Ala Met Thr Asp Gly Phe Gln Phe Glu Tyr
1               5                   10                  15

Gly Ser Glu Gly Ser Leu Pro Glu Asp Val Asn Ile Gln Leu Thr Phe
            20                  25                  30

Leu Arg

<210> SEQ ID NO 5
<211> LENGTH: 37
<212> TYPE: PRT
<213> ORGANISM: Yellow Croaker

<400> SEQUENCE: 5

Ser Gly Glu Met Gly Pro Ala Gly Pro Pro Gly Pro Pro Gly Pro Pro
1               5                   10                  15

Gly Ala Pro Gly Ala Pro Gly Gly Phe Asp Leu Gly Phe Ile Ala
            20                  25                  30

Gln Pro Gln Glu Lys
        35

<210> SEQ ID NO 6
<211> LENGTH: 28
<212> TYPE: PRT
<213> ORGANISM: Yellow Croaker

<400> SEQUENCE: 6

Leu Pro Ile Ile Asp Ile Ala Pro Met Asp Val Gly Ala Pro Asp Gln
1               5                   10                  15

Glu Phe Gly Leu Glu Val Gly Pro Val Cys Phe Leu
            20                  25

<210> SEQ ID NO 7
<211> LENGTH: 33
<212> TYPE: PRT
<213> ORGANISM: Yellow Croaker

<400> SEQUENCE: 7

Gly Pro Pro Gly Pro Ala Gly Ala Ser Gly Pro Gln Gly Phe Thr Gly
1               5                   10                  15

Pro Pro Gly Glu Pro Gly Glu Pro Gly Ala Ser Gly Ala Met Gly Pro
            20                  25                  30

Arg

<210> SEQ ID NO 8
<211> LENGTH: 30
<212> TYPE: PRT
<213> ORGANISM: Yellow Croaker

<400> SEQUENCE: 8

Gly Phe Thr Gly Met Gln Gly Pro Pro Gly Pro Ser Gly Pro Ser Gly
1               5                   10                  15

Asp Gln Gly Pro Ala Gly Ala Ala Gly Pro Ala Gly Pro Arg
            20                  25                  30

<210> SEQ ID NO 9
<211> LENGTH: 30
<212> TYPE: PRT
<213> ORGANISM: Yellow Croaker

<400> SEQUENCE: 9

Gly Asn Asp Gly Ala Ala Gly Ala Ala Gly Pro Pro Gly Pro Thr Gly
```

```
                1               5                   10                  15
Pro Ala Gly Pro Pro Gly Phe Pro Gly Gly Pro Gly Ala Lys
                20                  25                  30

<210> SEQ ID NO 10
<211> LENGTH: 21
<212> TYPE: PRT
<213> ORGANISM: Yellow Croaker

<400> SEQUENCE: 10

Val Tyr Cys Asn Met Glu Thr Gly Glu Thr Cys Val Thr Pro Thr Gln
1               5                   10                  15

Ser Glu Val Ala Lys
            20

<210> SEQ ID NO 11
<211> LENGTH: 22
<212> TYPE: PRT
<213> ORGANISM: Yellow Croaker

<400> SEQUENCE: 11

Ala Gln Gly Glu Asp Asp His Thr Gly Gly Ser Cys Thr Leu Asp Gly
1               5                   10                  15

Gln Val Phe Ala Asp Arg
            20

<210> SEQ ID NO 12
<211> LENGTH: 27
<212> TYPE: PRT
<213> ORGANISM: Yellow Croaker

<400> SEQUENCE: 12

Gly Glu Pro Gly Asn Pro Gly Pro Ala Gly Ala Ala Gly Pro Ser Gly
1               5                   10                  15

Asn Pro Gly Ala Asp Gly Ala Thr Gly Pro Lys
            20                  25

<210> SEQ ID NO 13
<211> LENGTH: 27
<212> TYPE: PRT
<213> ORGANISM: Yellow Croaker

<400> SEQUENCE: 13

Gly Asp Ala Gly Pro Pro Gly Ala Ala Gly Pro Thr Gly Ala Pro Gly
1               5                   10                  15

Pro Gln Gly Pro Val Gly Asn Thr Gly Ala Lys
            20                  25

<210> SEQ ID NO 14
<211> LENGTH: 26
<212> TYPE: PRT
<213> ORGANISM: Yellow Croaker

<400> SEQUENCE: 14

Gly Glu Thr Gly Pro Asn Gly Ala Thr Gly Ala Pro Gly Pro Pro Gly
1               5                   10                  15

Ala Pro Gly Pro Val Gly Pro Ala Gly Lys
            20                  25

<210> SEQ ID NO 15
<211> LENGTH: 24
<212> TYPE: PRT
```

-continued

<213> ORGANISM: Yellow Croaker

<400> SEQUENCE: 15

Gly Asp Ala Gly Ala Pro Gly Ala Pro Gly Ala Gln Gly Pro Pro Gly
1               5                   10                  15

Leu Gln Gly Met Pro Gly Glu Arg
            20

<210> SEQ ID NO 16
<211> LENGTH: 19
<212> TYPE: PRT
<213> ORGANISM: Yellow Croaker

<400> SEQUENCE: 16

Phe Thr Tyr Ser Val Leu Glu Asp Gly Cys Thr Ser His Thr Gly Thr
1               5                   10                  15

Trp Gly Lys

<210> SEQ ID NO 17
<211> LENGTH: 24
<212> TYPE: PRT
<213> ORGANISM: Yellow Croaker

<400> SEQUENCE: 17

Gly Ser Pro Gly Ala Glu Gly Ala Ser Gly Ser Ala Gly Leu Pro Gly
1               5                   10                  15

Pro Gln Gly Ile Ala Gly Gln Arg
            20

<210> SEQ ID NO 18
<211> LENGTH: 24
<212> TYPE: PRT
<213> ORGANISM: Yellow Croaker

<400> SEQUENCE: 18

Gly Glu Ser Gly Pro Pro Gly Pro Ala Gly Phe Ala Gly Pro Pro Gly
1               5                   10                  15

Ala Asp Gly Gln Pro Gly Ala Lys
            20

<210> SEQ ID NO 19
<211> LENGTH: 18
<212> TYPE: PRT
<213> ORGANISM: Yellow Croaker

<400> SEQUENCE: 19

Ser Gly Glu Tyr Trp Ile Asp Pro Asp Gln Gly Cys Thr Gln Asp Ala
1               5                   10                  15

Ile Lys

<210> SEQ ID NO 20
<211> LENGTH: 22
<212> TYPE: PRT
<213> ORGANISM: Yellow Croaker

<400> SEQUENCE: 20

Thr Gly Pro Val Gly Ala Ala Gly Gln Asp Gly Arg Pro Gly Pro Pro
1               5                   10                  15

Gly Thr Val Gly Ala Arg
            20

```
<210> SEQ ID NO 21
<211> LENGTH: 21
<212> TYPE: PRT
<213> ORGANISM: Yellow Croaker

<400> SEQUENCE: 21

Val Gly Pro Pro Gly Pro Ser Gly Asn Pro Gly Pro Pro Gly Pro Ala
1               5                   10                  15

Gly Pro Ser Gly Lys
            20

<210> SEQ ID NO 22
<211> LENGTH: 20
<212> TYPE: PRT
<213> ORGANISM: Yellow Croaker

<400> SEQUENCE: 22

Gly Glu Gly Gly Ala Pro Gly Val Gln Pro Pro Gly Pro Ser Gly
1               5                   10                  15

Glu Glu Gly Lys
            20

<210> SEQ ID NO 23
<211> LENGTH: 20
<212> TYPE: PRT
<213> ORGANISM: Yellow Croaker

<400> SEQUENCE: 23

Gly Pro Pro Gly Pro Met Gly Pro Gly Leu Ala Gly Ser Pro Gly
1               5                   10                  15

Glu Ala Gly Arg
            20

<210> SEQ ID NO 24
<211> LENGTH: 15
<212> TYPE: PRT
<213> ORGANISM: Yellow Croaker

<400> SEQUENCE: 24

Leu Met Ser Thr Glu Ala Ser Gln Asn Ile Thr Tyr His Cys Lys
1               5                   10                  15

<210> SEQ ID NO 25
<211> LENGTH: 19
<212> TYPE: PRT
<213> ORGANISM: Yellow Croaker

<400> SEQUENCE: 25

Asp Gly Asp Val Gly Ala Pro Gly Ala Pro Gly Pro Ala Gly Pro Ala
1               5                   10                  15

Gly Glu Arg

<210> SEQ ID NO 26
<211> LENGTH: 18
<212> TYPE: PRT
<213> ORGANISM: Yellow Croaker

<400> SEQUENCE: 26

Gly Glu Ser Gly Ser Ala Gly Glu Asn Gly Thr Pro Gly Ala Met Gly
1               5                   10                  15

Pro Arg
```

```
<210> SEQ ID NO 27
<211> LENGTH: 16
<212> TYPE: PRT
<213> ORGANISM: Yellow Croaker

<400> SEQUENCE: 27

Ser Pro Ala Met Pro Val Ile Gly Pro Met Gly Pro Met Gly Pro Arg
1               5                   10                  15

<210> SEQ ID NO 28
<211> LENGTH: 18
<212> TYPE: PRT
<213> ORGANISM: Yellow Croaker

<400> SEQUENCE: 28

Gly Leu Thr Gly Pro Ile Gly Leu Pro Gly Pro Ala Gly Ala Thr Gly
1               5                   10                  15

Asp Lys

<210> SEQ ID NO 29
<211> LENGTH: 18
<212> TYPE: PRT
<213> ORGANISM: Yellow Croaker

<400> SEQUENCE: 29

Gly Glu Thr Gly Pro Ala Gly Pro Ser Gly Ala Pro Gly Pro Ala Gly
1               5                   10                  15

Pro Arg

<210> SEQ ID NO 30
<211> LENGTH: 18
<212> TYPE: PRT
<213> ORGANISM: Yellow Croaker

<400> SEQUENCE: 30

Gly Ala Pro Gly Ala Ala Gly Val Ala Gly Ala Pro Gly Phe Pro Gly
1               5                   10                  15

Pro Arg

<210> SEQ ID NO 31
<211> LENGTH: 16
<212> TYPE: PRT
<213> ORGANISM: Yellow Croaker

<400> SEQUENCE: 31

Asp Gly Met Ser Gly Leu Pro Gly Pro Thr Gly Pro Pro Gly Pro Arg
1               5                   10                  15

<210> SEQ ID NO 32
<211> LENGTH: 16
<212> TYPE: PRT
<213> ORGANISM: Yellow Croaker

<400> SEQUENCE: 32

Thr Gly Glu Met Gly Ala Ala Gly Pro Pro Gly Thr Pro Gly Glu Lys
1               5                   10                  15

<210> SEQ ID NO 33
<211> LENGTH: 13
<212> TYPE: PRT
<213> ORGANISM: Yellow Croaker

<400> SEQUENCE: 33
```

Ala Leu Leu Leu Gln Gly Ser Asn Glu Ile Glu Ile Arg
1               5                   10

<210> SEQ ID NO 34
<211> LENGTH: 17
<212> TYPE: PRT
<213> ORGANISM: Yellow Croaker

<400> SEQUENCE: 34

Gly Pro Ser Gly Pro Pro Gly Ala Thr Gly Phe Pro Gly Ala Ala Gly
1               5                   10                  15

Arg

<210> SEQ ID NO 35
<211> LENGTH: 14
<212> TYPE: PRT
<213> ORGANISM: Yellow Croaker

<400> SEQUENCE: 35

Asn Ser Val Ala Tyr Met Asp Ala Ser Ala Gly Asn Leu Lys
1               5                   10

<210> SEQ ID NO 36
<211> LENGTH: 13
<212> TYPE: PRT
<213> ORGANISM: Yellow Croaker

<400> SEQUENCE: 36

Leu Ala Leu Leu Leu Ser Ala Ala Val Leu Leu Val Arg
1               5                   10

<210> SEQ ID NO 37
<211> LENGTH: 15
<212> TYPE: PRT
<213> ORGANISM: Yellow Croaker

<400> SEQUENCE: 37

Gly Glu Pro Gly Ala Val Gly Ile Ile Gly Leu Ala Gly Ala Arg
1               5                   10                  15

<210> SEQ ID NO 38
<211> LENGTH: 14
<212> TYPE: PRT
<213> ORGANISM: Yellow Croaker

<400> SEQUENCE: 38

Gly Phe Pro Gly Leu Pro Gly Pro Ser Gly Glu Val Gly Lys
1               5                   10

<210> SEQ ID NO 39
<211> LENGTH: 15
<212> TYPE: PRT
<213> ORGANISM: Yellow Croaker

<400> SEQUENCE: 39

Gly Pro Ser Gly Pro Gln Gly Ala Ala Gly Ala Pro Gly Pro Lys
1               5                   10                  15

<210> SEQ ID NO 40
<211> LENGTH: 14
<212> TYPE: PRT
<213> ORGANISM: Yellow Croaker

<400> SEQUENCE: 40

```
Gly Met Thr Gly Ser Pro Gly Asn Pro Gly Ala Asp Gly Lys
1               5                   10
```

<210> SEQ ID NO 41
<211> LENGTH: 14
<212> TYPE: PRT
<213> ORGANISM: Yellow Croaker

<400> SEQUENCE: 41

```
Gly Val Met Gly Pro Thr Gly Pro Thr Gly Ala Pro Gly Lys
1               5                   10
```

<210> SEQ ID NO 42
<211> LENGTH: 12
<212> TYPE: PRT
<213> ORGANISM: Yellow Croaker

<400> SEQUENCE: 42

```
Asn Gly Glu Asp Gly Glu Ser Gly Lys Pro Gly Arg
1               5                   10
```

<210> SEQ ID NO 43
<211> LENGTH: 10
<212> TYPE: PRT
<213> ORGANISM: Yellow Croaker

<400> SEQUENCE: 43

```
Ser Leu Ser Gln Gln Ile Glu Gln Ile Arg
1               5                   10
```

<210> SEQ ID NO 44
<211> LENGTH: 12
<212> TYPE: PRT
<213> ORGANISM: Yellow Croaker

<400> SEQUENCE: 44

```
Gly Gln Pro Gly Val Met Gly Phe Pro Gly Pro Lys
1               5                   10
```

<210> SEQ ID NO 45
<211> LENGTH: 12
<212> TYPE: PRT
<213> ORGANISM: Yellow Croaker

<400> SEQUENCE: 45

```
Gly Phe Pro Gly Thr Pro Gly Leu Pro Gly Ile Lys
1               5                   10
```

<210> SEQ ID NO 46
<211> LENGTH: 12
<212> TYPE: PRT
<213> ORGANISM: Yellow Croaker

<400> SEQUENCE: 46

```
Glu Gly Thr Pro Gly Asn Glu Gly Ala Ala Gly Arg
1               5                   10
```

<210> SEQ ID NO 47
<211> LENGTH: 12
<212> TYPE: PRT
<213> ORGANISM: Yellow Croaker

<400> SEQUENCE: 47

```
Gly Ala Ala Gly Glu Gly Gly Lys Pro Gly Glu Arg
1               5                   10
```

<210> SEQ ID NO 48
<211> LENGTH: 12
<212> TYPE: PRT
<213> ORGANISM: Yellow Croaker

<400> SEQUENCE: 48

Gly Phe Pro Gly Ser Asp Gly Ser Ala Gly Pro Lys
1               5                   10

<210> SEQ ID NO 49
<211> LENGTH: 12
<212> TYPE: PRT
<213> ORGANISM: Yellow Croaker

<400> SEQUENCE: 49

Gly Asn Thr Gly Glu Ala Gly Ala Pro Gly Ala Lys
1               5                   10

<210> SEQ ID NO 50
<211> LENGTH: 12
<212> TYPE: PRT
<213> ORGANISM: Yellow Croaker

<400> SEQUENCE: 50

Gly Ser Pro Gly Ala Pro Gly Asn Asp Gly Ala Lys
1               5                   10

<210> SEQ ID NO 51
<211> LENGTH: 12
<212> TYPE: PRT
<213> ORGANISM: Yellow Croaker

<400> SEQUENCE: 51

Gly Ala Pro Gly Val Ala Gly Pro Val Gly Ser Arg
1               5                   10

<210> SEQ ID NO 52
<211> LENGTH: 8
<212> TYPE: PRT
<213> ORGANISM: Yellow Croaker

<400> SEQUENCE: 52

Met Phe Ser Phe Val Asp Leu Arg
1               5

<210> SEQ ID NO 53
<211> LENGTH: 9
<212> TYPE: PRT
<213> ORGANISM: Yellow Croaker

<400> SEQUENCE: 53

Asp Leu Glu Val Asp Gly Thr Leu Lys
1               5

<210> SEQ ID NO 54
<211> LENGTH: 10
<212> TYPE: PRT
<213> ORGANISM: Yellow Croaker

<400> SEQUENCE: 54

Gln Gly Pro Ser Gly Pro Gly Gly Glu Arg
1               5                   10

<210> SEQ ID NO 55
<211> LENGTH: 10
<212> TYPE: PRT
<213> ORGANISM: Yellow Croaker

<400> SEQUENCE: 55

Thr Gly Glu Pro Gly Leu Pro Gly Ala Lys
1               5                   10

<210> SEQ ID NO 56
<211> LENGTH: 7
<212> TYPE: PRT
<213> ORGANISM: Yellow Croaker

<400> SEQUENCE: 56

Met Cys His Pro Asp Trp Lys
1               5

<210> SEQ ID NO 57
<211> LENGTH: 9
<212> TYPE: PRT
<213> ORGANISM: Yellow Croaker

<400> SEQUENCE: 57

Gly Glu Thr Gly Glu Ala Gly Glu Arg
1               5

<210> SEQ ID NO 58
<211> LENGTH: 9
<212> TYPE: PRT
<213> ORGANISM: Yellow Croaker

<400> SEQUENCE: 58

Gly Ile Val Gly Leu Pro Gly Gln Arg
1               5

<210> SEQ ID NO 59
<211> LENGTH: 11
<212> TYPE: PRT
<213> ORGANISM: Yellow Croaker

<400> SEQUENCE: 59

Gly Pro Ala Gly Ser Ala Gly Ser Pro Gly Lys
1               5                   10

<210> SEQ ID NO 60
<211> LENGTH: 8
<212> TYPE: PRT
<213> ORGANISM: Yellow Croaker

<400> SEQUENCE: 60

Ala Asp Asp Ala Asn Val Leu Arg
1               5

<210> SEQ ID NO 61
<211> LENGTH: 9
<212> TYPE: PRT
<213> ORGANISM: Yellow Croaker

<400> SEQUENCE: 61

Gly Phe Ser Gly Leu Asp Gly Ala Lys
1               5

<210> SEQ ID NO 62
<211> LENGTH: 9

-continued

```
<212> TYPE: PRT
<213> ORGANISM: Yellow Croaker

<400> SEQUENCE: 62

Gly Glu Ala Gly Glu Asn Gly Ala Lys
1               5

<210> SEQ ID NO 63
<211> LENGTH: 9
<212> TYPE: PRT
<213> ORGANISM: Yellow Croaker

<400> SEQUENCE: 63

Gly Asp Ala Gly Pro Gln Gly Ala Arg
1               5

<210> SEQ ID NO 64
<211> LENGTH: 9
<212> TYPE: PRT
<213> ORGANISM: Yellow Croaker

<400> SEQUENCE: 64

Gly Ala Ala Gly Leu Pro Gly Leu Arg
1               5

<210> SEQ ID NO 65
<211> LENGTH: 9
<212> TYPE: PRT
<213> ORGANISM: Yellow Croaker

<400> SEQUENCE: 65

Gly Pro Pro Gly Ala Gln Gly Ala Arg
1               5

<210> SEQ ID NO 66
<211> LENGTH: 9
<212> TYPE: PRT
<213> ORGANISM: Yellow Croaker

<400> SEQUENCE: 66

Gly Pro Ala Gly Ala Val Gly Leu Arg
1               5

<210> SEQ ID NO 67
<211> LENGTH: 6
<212> TYPE: PRT
<213> ORGANISM: Yellow Croaker

<400> SEQUENCE: 67

Asn Trp Tyr Val Ser Lys
1               5

<210> SEQ ID NO 68
<211> LENGTH: 9
<212> TYPE: PRT
<213> ORGANISM: Yellow Croaker

<400> SEQUENCE: 68

Gly Ala Glu Gly Pro Ala Gly Ala Arg
1               5

<210> SEQ ID NO 69
<211> LENGTH: 9
<212> TYPE: PRT
<213> ORGANISM: Yellow Croaker
```

-continued

```
<400> SEQUENCE: 69

Gly Asp Ser Gly Pro Ala Gly Pro Lys
1               5

<210> SEQ ID NO 70
<211> LENGTH: 10
<212> TYPE: PRT
<213> ORGANISM: Yellow Croaker

<400> SEQUENCE: 70

Ala Gly Ala Ala Gly Ala Ala Gly Ala Arg
1               5                   10

<210> SEQ ID NO 71
<211> LENGTH: 9
<212> TYPE: PRT
<213> ORGANISM: Yellow Croaker

<400> SEQUENCE: 71

Gly Glu Pro Gly Ala Ala Gly Gly Arg
1               5

<210> SEQ ID NO 72
<211> LENGTH: 9
<212> TYPE: PRT
<213> ORGANISM: Yellow Croaker

<400> SEQUENCE: 72

Gly Ala Pro Gly Ala Val Gly Pro Lys
1               5

<210> SEQ ID NO 73
<211> LENGTH: 8
<212> TYPE: PRT
<213> ORGANISM: Yellow Croaker

<400> SEQUENCE: 73

Gly Ala Thr Gly Glu Pro Gly Arg
1               5

<210> SEQ ID NO 74
<211> LENGTH: 8
<212> TYPE: PRT
<213> ORGANISM: Yellow Croaker

<400> SEQUENCE: 74

Gly Glu Thr Gly Pro Ala Gly Arg
1               5

<210> SEQ ID NO 75
<211> LENGTH: 6
<212> TYPE: PRT
<213> ORGANISM: Yellow Croaker

<400> SEQUENCE: 75

Thr Val Ile Asp Tyr Lys
1               5

<210> SEQ ID NO 76
<211> LENGTH: 6
<212> TYPE: PRT
<213> ORGANISM: Yellow Croaker

<400> SEQUENCE: 76
```

```
Ala Pro Asp Pro Tyr Arg
1               5

<210> SEQ ID NO 77
<211> LENGTH: 8
<212> TYPE: PRT
<213> ORGANISM: Yellow Croaker

<400> SEQUENCE: 77

Gly Thr Asp Gly Ala Pro Gly Lys
1               5

<210> SEQ ID NO 78
<211> LENGTH: 8
<212> TYPE: PRT
<213> ORGANISM: Yellow Croaker

<400> SEQUENCE: 78

Gly Ala Ala Gly Ile Pro Gly Lys
1               5

<210> SEQ ID NO 79
<211> LENGTH: 6
<212> TYPE: PRT
<213> ORGANISM: Yellow Croaker

<400> SEQUENCE: 79

Gly Phe Pro Gly Glu Arg
1               5

<210> SEQ ID NO 80
<211> LENGTH: 6
<212> TYPE: PRT
<213> ORGANISM: Yellow Croaker

<400> SEQUENCE: 80

Ala Glu Gly Asn Ser Arg
1               5

<210> SEQ ID NO 81
<211> LENGTH: 6
<212> TYPE: PRT
<213> ORGANISM: Yellow Croaker

<400> SEQUENCE: 81

Ser Pro Asp Gly Thr Arg
1               5

<210> SEQ ID NO 82
<211> LENGTH: 6
<212> TYPE: PRT
<213> ORGANISM: Yellow Croaker

<400> SEQUENCE: 82

Gly Leu Pro Gly Glu Arg
1               5

<210> SEQ ID NO 83
<211> LENGTH: 7
<212> TYPE: PRT
<213> ORGANISM: Yellow Croaker

<400> SEQUENCE: 83

Asp Gly Ala Ala Gly Pro Lys
```

```
1               5

<210> SEQ ID NO 84
<211> LENGTH: 6
<212> TYPE: PRT
<213> ORGANISM: Yellow Croaker

<400> SEQUENCE: 84

Gly Val Pro Gly Glu Arg
1               5

<210> SEQ ID NO 85
<211> LENGTH: 6
<212> TYPE: PRT
<213> ORGANISM: Yellow Croaker

<400> SEQUENCE: 85

Gly Pro Pro Gly Glu Arg
1               5

<210> SEQ ID NO 86
<211> LENGTH: 6
<212> TYPE: PRT
<213> ORGANISM: Yellow Croaker

<400> SEQUENCE: 86

Gly Ala Asn Gly Glu Arg
1               5

<210> SEQ ID NO 87
<211> LENGTH: 6
<212> TYPE: PRT
<213> ORGANISM: Yellow Croaker

<400> SEQUENCE: 87

Gly Asp Gln Gly Ala Lys
1               5

<210> SEQ ID NO 88
<211> LENGTH: 6
<212> TYPE: PRT
<213> ORGANISM: Yellow Croaker

<400> SEQUENCE: 88

Gly Glu Ala Gly Ala Lys
1               5

<210> SEQ ID NO 89
<211> LENGTH: 6
<212> TYPE: PRT
<213> ORGANISM: Yellow Croaker

<400> SEQUENCE: 89

Gly Ala Pro Gly Gly Arg
1               5

<210> SEQ ID NO 90
<211> LENGTH: 3
<212> TYPE: PRT
<213> ORGANISM: Yellow Croaker

<400> SEQUENCE: 90

Met Tyr Arg
1
```

-continued

```
<210> SEQ ID NO 91
<211> LENGTH: 4
<212> TYPE: PRT
<213> ORGANISM: Yellow Croaker

<400> SEQUENCE: 91

Asn Gly Asp Arg
1

<210> SEQ ID NO 92
<211> LENGTH: 4
<212> TYPE: PRT
<213> ORGANISM: Yellow Croaker

<400> SEQUENCE: 92

Asn Pro Ala Arg
1

<210> SEQ ID NO 93
<211> LENGTH: 4
<212> TYPE: PRT
<213> ORGANISM: Yellow Croaker

<400> SEQUENCE: 93

Ser Gly Glu Arg
1

<210> SEQ ID NO 94
<211> LENGTH: 4
<212> TYPE: PRT
<213> ORGANISM: Yellow Croaker

<400> SEQUENCE: 94

Asp Gly Pro Arg
1

<210> SEQ ID NO 95
<211> LENGTH: 4
<212> TYPE: PRT
<213> ORGANISM: Yellow Croaker

<400> SEQUENCE: 95

Glu Gly Pro Lys
1

<210> SEQ ID NO 96
<211> LENGTH: 3
<212> TYPE: PRT
<213> ORGANISM: Yellow Croaker

<400> SEQUENCE: 96

Thr Cys Arg
1

<210> SEQ ID NO 97
<211> LENGTH: 3
<212> TYPE: PRT
<213> ORGANISM: Yellow Croaker

<400> SEQUENCE: 97

Asp Leu Lys
1

<210> SEQ ID NO 98
```

```
<211> LENGTH: 3
<212> TYPE: PRT
<213> ORGANISM: Yellow Croaker

<400> SEQUENCE: 98

Asn Ile Lys
1

<210> SEQ ID NO 99
<211> LENGTH: 3
<212> TYPE: PRT
<213> ORGANISM: Yellow Croaker

<400> SEQUENCE: 99

Gly His Arg
1

<210> SEQ ID NO 100
<211> LENGTH: 3
<212> TYPE: PRT
<213> ORGANISM: Yellow Croaker

<400> SEQUENCE: 100

Thr Ser Arg
1

<210> SEQ ID NO 101
<211> LENGTH: 3
<212> TYPE: PRT
<213> ORGANISM: Yellow Croaker

<400> SEQUENCE: 101

Gly Glu Arg
1

<210> SEQ ID NO 102
<211> LENGTH: 3
<212> TYPE: PRT
<213> ORGANISM: Yellow Croaker

<400> SEQUENCE: 102

Gly Asp Arg
1

<210> SEQ ID NO 103
<211> LENGTH: 3
<212> TYPE: PRT
<213> ORGANISM: Yellow Croaker

<400> SEQUENCE: 103

Gly Asn Arg
1

<210> SEQ ID NO 104
<211> LENGTH: 3
<212> TYPE: PRT
<213> ORGANISM: Yellow Croaker

<400> SEQUENCE: 104

Thr Ser Lys
1

<210> SEQ ID NO 105
<211> LENGTH: 3
<212> TYPE: PRT
```

-continued

```
<213> ORGANISM: Yellow Croaker

<400> SEQUENCE: 105

Gly Met Lys
1

<210> SEQ ID NO 106
<211> LENGTH: 3
<212> TYPE: PRT
<213> ORGANISM: Yellow Croaker

<400> SEQUENCE: 106

Gly Pro Arg
1

<210> SEQ ID NO 107
<211> LENGTH: 3
<212> TYPE: PRT
<213> ORGANISM: Yellow Croaker

<400> SEQUENCE: 107

Gly Asp Lys
1

<210> SEQ ID NO 108
<211> LENGTH: 3
<212> TYPE: PRT
<213> ORGANISM: Yellow Croaker

<400> SEQUENCE: 108

Gly Ala Arg
1

<210> SEQ ID NO 109
<211> LENGTH: 3
<212> TYPE: PRT
<213> ORGANISM: Yellow Croaker

<400> SEQUENCE: 109

Gly Pro Lys
1

<210> SEQ ID NO 110
<211> LENGTH: 2
<212> TYPE: PRT
<213> ORGANISM: Yellow Croaker

<400> SEQUENCE: 110

Asp Arg
1

<210> SEQ ID NO 111
<211> LENGTH: 2
<212> TYPE: PRT
<213> ORGANISM: Yellow Croaker

<400> SEQUENCE: 111

Glu Lys
1

<210> SEQ ID NO 112
<211> LENGTH: 2
<212> TYPE: PRT
<213> ORGANISM: Yellow Croaker
```

<400> SEQUENCE: 112

Gly Arg
1

<210> SEQ ID NO 113
<211> LENGTH: 34
<212> TYPE: PRT
<213> ORGANISM: Yellow Croaker

<400> SEQUENCE: 113

His Val Trp Phe Gly Glu Thr Ile Asn Gly Gly Thr Glu Phe Thr Tyr
1               5                   10                  15

Asn Asp Glu Thr Ile Ser Pro Gln Ser Met Ala Thr Gln Leu Ala Phe
            20                  25                  30

Met Arg

<210> SEQ ID NO 114
<211> LENGTH: 37
<212> TYPE: PRT
<213> ORGANISM: Yellow Croaker

<400> SEQUENCE: 114

Gly Pro Pro Gly Tyr Val Gly Pro Ser Gly Pro Pro Gly Ser Pro Gly
1               5                   10                  15

Leu Pro Gly Pro Pro Gly Pro Ala Gly Gly Gly Tyr Asp Val Ser Gly
            20                  25                  30

Tyr Asp Glu Tyr Arg
        35

<210> SEQ ID NO 115
<211> LENGTH: 33
<212> TYPE: PRT
<213> ORGANISM: Yellow Croaker

<400> SEQUENCE: 115

Gly Pro Pro Gly Pro Pro Gly Pro Pro Gly Ser Gln Gly His Thr Gly
1               5                   10                  15

His Pro Gly Glu Pro Gly Glu Pro Gly Gln Pro Gly Pro Val Gly Ala
            20                  25                  30

Arg

<210> SEQ ID NO 116
<211> LENGTH: 28
<212> TYPE: PRT
<213> ORGANISM: Yellow Croaker

<400> SEQUENCE: 116

Leu Pro Ile Leu Asp Ile Ala Pro Leu Asp Ile Gly Gly Ala Glu Gln
1               5                   10                  15

Glu Phe Gly Leu Asp Ile Gly Pro Val Cys Phe Lys
            20                  25

<210> SEQ ID NO 117
<211> LENGTH: 33
<212> TYPE: PRT
<213> ORGANISM: Yellow Croaker

<400> SEQUENCE: 117

Gly Pro Ser Gly Glu Ser Gly Pro Pro Gly Ala Pro Gly Val Pro Gly
1               5                   10                  15

```
Ser Gly Gly Pro Leu Gly Leu Gln Gly Phe Val Gly Leu Pro Gly Ala
            20                  25                  30

Arg

<210> SEQ ID NO 118
<211> LENGTH: 25
<212> TYPE: PRT
<213> ORGANISM: Yellow Croaker

<400> SEQUENCE: 118

Leu Ser His Pro Glu Trp Thr Ser Gly Phe Tyr Trp Ile Asp Pro Asn
1               5                   10                  15

Gln Gly Cys Thr Asn Asp Ala Ile Lys
            20                  25

<210> SEQ ID NO 119
<211> LENGTH: 30
<212> TYPE: PRT
<213> ORGANISM: Yellow Croaker

<400> SEQUENCE: 119

Asp Gly Lys Pro Gly Leu Pro Gly Pro Pro Gly Pro Pro Gly Pro Pro
1               5                   10                  15

Gly Leu Gly Gly Asn Phe Ala Ala Gln Tyr Asp Gly Ser Lys
            20                  25                  30

<210> SEQ ID NO 120
<211> LENGTH: 30
<212> TYPE: PRT
<213> ORGANISM: Yellow Croaker

<400> SEQUENCE: 120

Gly Glu Gln Gly Pro Ala Gly Ala Pro Gly Phe Gln Gly Leu Pro Gly
1               5                   10                  15

Pro Ala Gly Pro Ala Gly Glu Ala Gly Lys Pro Gly Asp Arg
            20                  25                  30

<210> SEQ ID NO 121
<211> LENGTH: 30
<212> TYPE: PRT
<213> ORGANISM: Yellow Croaker

<400> SEQUENCE: 121

Gly His Ala Gly Leu Gln Gly Met Pro Gly Pro Ser Gly Pro Ser Gly
1               5                   10                  15

Asp Thr Gly Val Ala Gly Pro His Gly Pro Ala Gly Pro Arg
            20                  25                  30

<210> SEQ ID NO 122
<211> LENGTH: 30
<212> TYPE: PRT
<213> ORGANISM: Yellow Croaker

<400> SEQUENCE: 122

Gly Ala Asp Gly Asn Val Gly Pro Ala Gly Pro Ala Gly Pro Leu Gly
1               5                   10                  15

Ala Ala Gly Pro Pro Gly Phe Pro Gly Gly Pro Gly Pro Lys
            20                  25                  30

<210> SEQ ID NO 123
<211> LENGTH: 30
<212> TYPE: PRT
```

<213> ORGANISM: Yellow Croaker

<400> SEQUENCE: 123

Gly Glu Val Gly Ser Ala Gly Pro Ala Gly Pro Ala Gly Gln Ser Gly
1               5                   10                  15

Pro Ala Gly Pro Thr Gly Ala Ala Gly Pro Thr Gly Ala Arg
            20                  25                  30

<210> SEQ ID NO 124
<211> LENGTH: 27
<212> TYPE: PRT
<213> ORGANISM: Yellow Croaker

<400> SEQUENCE: 124

Gly Glu Pro Gly Pro Asn Gly Ala Val Gly Val Gly Pro Pro Gly
1               5                   10                  15

Asn Pro Gly Asn Asn Gly Leu Asn Gly Ala Lys
            20                  25

<210> SEQ ID NO 125
<211> LENGTH: 26
<212> TYPE: PRT
<213> ORGANISM: Yellow Croaker

<400> SEQUENCE: 125

Gly Glu Pro Gly Ser Pro Gly Ala Met Gly Leu Ala Gly Leu Pro Gly
1               5                   10                  15

Pro Ala Gly Pro Thr Gly Ala Val Gly Arg
            20                  25

<210> SEQ ID NO 126
<211> LENGTH: 24
<212> TYPE: PRT
<213> ORGANISM: Yellow Croaker

<400> SEQUENCE: 126

Gly Asp Ser Gly Pro Ala Gly Pro Ser Gly Glu Gln Gly Met Val Gly
1               5                   10                  15

Pro Pro Gly Pro Ala Gly Glu Lys
            20

<210> SEQ ID NO 127
<211> LENGTH: 24
<212> TYPE: PRT
<213> ORGANISM: Yellow Croaker

<400> SEQUENCE: 127

Gly Glu Pro Gly Ser Ala Gly Ala Ala Gly Ala Ala Gly His Gln Gly
1               5                   10                  15

Pro Gly Gly Met Pro Gly Glu Arg
            20

<210> SEQ ID NO 128
<211> LENGTH: 24
<212> TYPE: PRT
<213> ORGANISM: Yellow Croaker

<400> SEQUENCE: 128

Gly Glu Val Gly Pro Ala Gly Ala Ala Gly Phe Ala Gly Pro Pro Gly
1               5                   10                  15

Ala Asp Gly Gln Thr Gly Ala Arg
            20

<210> SEQ ID NO 129
<211> LENGTH: 24
<212> TYPE: PRT
<213> ORGANISM: Yellow Croaker

<400> SEQUENCE: 129

Gly Ala Pro Gly Pro Asp Gly Asn Asn Gly Ala Thr Gly Pro Gly Gly
1               5                   10                  15

Val Val Gly Asn Ala Gly Glu Lys
            20

<210> SEQ ID NO 130
<211> LENGTH: 20
<212> TYPE: PRT
<213> ORGANISM: Yellow Croaker

<400> SEQUENCE: 130

Gly Pro Pro Gly Asn Ile Gly Leu Pro Gly Met Thr Gly Pro Gln Gly
1               5                   10                  15

Glu Ala Gly Arg
            20

<210> SEQ ID NO 131
<211> LENGTH: 19
<212> TYPE: PRT
<213> ORGANISM: Yellow Croaker

<400> SEQUENCE: 131

Glu Gly Asn Pro Gly Asn Asp Gly Pro Pro Gly Arg Pro Gly Ile Pro
1               5                   10                  15

Gly Phe Lys

<210> SEQ ID NO 132
<211> LENGTH: 20
<212> TYPE: PRT
<213> ORGANISM: Yellow Croaker

<400> SEQUENCE: 132

Gly Glu Pro Gly Asn Ser Gly Ala Gln Gly Pro Pro Gly Pro Gln Gly
1               5                   10                  15

Glu Glu Gly Lys
            20

<210> SEQ ID NO 133
<211> LENGTH: 16
<212> TYPE: PRT
<213> ORGANISM: Yellow Croaker

<400> SEQUENCE: 133

Ser Leu Asn Thr Gln Ile Glu Asn Leu Leu Thr Pro Glu Gly Ser Arg
1               5                   10                  15

<210> SEQ ID NO 134
<211> LENGTH: 15
<212> TYPE: PRT
<213> ORGANISM: Yellow Croaker

<400> SEQUENCE: 134

Leu Leu Ser Asn Gln Ala Ser Gln Asn Ile Thr Tyr His Cys Lys
1               5                   10                  15

```
<210> SEQ ID NO 135
<211> LENGTH: 21
<212> TYPE: PRT
<213> ORGANISM: Yellow Croaker

<400> SEQUENCE: 135

Val Gly Ala Ala Gly Pro Ala Gly Ile Val Gly Pro Pro Gly Ala Val
1               5                   10                  15

Gly Pro Ala Gly Lys
            20

<210> SEQ ID NO 136
<211> LENGTH: 16
<212> TYPE: PRT
<213> ORGANISM: Yellow Croaker

<400> SEQUENCE: 136

Ala Gly Glu Asp Gly Asn Asn Gly Arg Pro Gly Lys Pro Gly Asp Arg
1               5                   10                  15

<210> SEQ ID NO 137
<211> LENGTH: 14
<212> TYPE: PRT
<213> ORGANISM: Yellow Croaker

<400> SEQUENCE: 137

Glu Thr Cys Ile Tyr Ala His Pro Glu Ser Ile Ala Gln Lys
1               5                   10

<210> SEQ ID NO 138
<211> LENGTH: 18
<212> TYPE: PRT
<213> ORGANISM: Yellow Croaker

<400> SEQUENCE: 138

Gly Met Pro Gly Pro Ala Gly Pro Gly Pro Thr Gly Ala Asn Gly
1               5                   10                  15

Asp Lys

<210> SEQ ID NO 139
<211> LENGTH: 18
<212> TYPE: PRT
<213> ORGANISM: Yellow Croaker

<400> SEQUENCE: 139

Gly Asn Pro Gly Ala Ala Gly Ala Ser Gly Pro Gln Gly Pro Met Gly
1               5                   10                  15

Ser Arg

<210> SEQ ID NO 140
<211> LENGTH: 18
<212> TYPE: PRT
<213> ORGANISM: Yellow Croaker

<400> SEQUENCE: 140

Gly Ala Ser Gly Thr Pro Gly Val Ala Gly Ala Pro Gly Phe Pro Gly
1               5                   10                  15

Pro Arg

<210> SEQ ID NO 141
<211> LENGTH: 18
<212> TYPE: PRT
<213> ORGANISM: Yellow Croaker
```

-continued

<400> SEQUENCE: 141

Gly Glu Leu Gly Ala Ala Gly Ala Val Gly Pro Ser Gly Pro Gln Gly
1               5                   10                  15

Ala Arg

<210> SEQ ID NO 142
<211> LENGTH: 18
<212> TYPE: PRT
<213> ORGANISM: Yellow Croaker

<400> SEQUENCE: 142

Gly Glu Pro Gly Ala His Gly Ala Ala Gly Thr Pro Gly Leu Ala Gly
1               5                   10                  15

Ala Arg

<210> SEQ ID NO 143
<211> LENGTH: 17
<212> TYPE: PRT
<213> ORGANISM: Yellow Croaker

<400> SEQUENCE: 143

Gly Glu Thr Gly Pro Ala Gly Leu Thr Gly Phe Pro Gly Ala Ala Gly
1               5                   10                  15

Arg

<210> SEQ ID NO 144
<211> LENGTH: 14
<212> TYPE: PRT
<213> ORGANISM: Yellow Croaker

<400> SEQUENCE: 144

Asn Ser Val Ala Tyr Met Asp Gly Glu Ser Gly Ser Leu Lys
1               5                   10

<210> SEQ ID NO 145
<211> LENGTH: 18
<212> TYPE: PRT
<213> ORGANISM: Yellow Croaker

<400> SEQUENCE: 145

Gly Glu Ala Gly Pro Gly Gly Pro Ala Gly Pro Val Gly Ala Ala Gly
1               5                   10                  15

Ala Arg

<210> SEQ ID NO 146
<211> LENGTH: 15
<212> TYPE: PRT
<213> ORGANISM: Yellow Croaker

<400> SEQUENCE: 146

Ala Pro Asp Pro Gly Pro Gly Pro Met Gly Met Met Gly Ala Arg
1               5                   10                  15

<210> SEQ ID NO 147
<211> LENGTH: 13
<212> TYPE: PRT
<213> ORGANISM: Yellow Croaker

<400> SEQUENCE: 147

Ala Val Val Leu Gln Gly Ser Asn Asp Val Glu Leu Arg
1               5                   10

<210> SEQ ID NO 148
<211> LENGTH: 12
<212> TYPE: PRT
<213> ORGANISM: Yellow Croaker

<400> SEQUENCE: 148

Phe Thr Phe Ser Val Leu Glu Asp Gly Cys Thr Arg
1               5                   10

<210> SEQ ID NO 149
<211> LENGTH: 15
<212> TYPE: PRT
<213> ORGANISM: Yellow Croaker

<400> SEQUENCE: 149

Gly Pro Thr Gly Glu Leu Gly Ala Thr Gly Val Ala Gly Asn Arg
1               5                   10                  15

<210> SEQ ID NO 150
<211> LENGTH: 15
<212> TYPE: PRT
<213> ORGANISM: Yellow Croaker

<400> SEQUENCE: 150

Gly Glu Ser Gly Ala Phe Gly Pro Ala Gly Pro Ser Gly Pro Arg
1               5                   10                  15

<210> SEQ ID NO 151
<211> LENGTH: 15
<212> TYPE: PRT
<213> ORGANISM: Yellow Croaker

<400> SEQUENCE: 151

Gly Gly Pro Gly Pro Gln Gly Pro Gln Gly Ala Ala Gly Gln Arg
1               5                   10                  15

<210> SEQ ID NO 152
<211> LENGTH: 15
<212> TYPE: PRT
<213> ORGANISM: Yellow Croaker

<400> SEQUENCE: 152

Gly Ile Pro Gly Asp Gln Gly Leu Ala Gly Ala Ala Gly Gly Lys
1               5                   10                  15

<210> SEQ ID NO 153
<211> LENGTH: 14
<212> TYPE: PRT
<213> ORGANISM: Yellow Croaker

<400> SEQUENCE: 153

Gly Leu Pro Gly Ser Pro Gly Ser Ser Gly Pro Thr Gly Lys
1               5                   10

<210> SEQ ID NO 154
<211> LENGTH: 12
<212> TYPE: PRT
<213> ORGANISM: Yellow Croaker

<400> SEQUENCE: 154

Gly Gln Pro Gly Asn Ile Gly Phe Pro Gly Pro Lys
1               5                   10

```
<210> SEQ ID NO 155
<211> LENGTH: 12
<212> TYPE: PRT
<213> ORGANISM: Yellow Croaker

<400> SEQUENCE: 155

Gly Phe Pro Gly Thr Pro Gly Leu Pro Gly Met Lys
1               5                   10

<210> SEQ ID NO 156
<211> LENGTH: 14
<212> TYPE: PRT
<213> ORGANISM: Yellow Croaker

<400> SEQUENCE: 156

Gly Ser Pro Gly Gly Ala Gly Ala Leu Gly Glu Ala Gly Arg
1               5                   10

<210> SEQ ID NO 157
<211> LENGTH: 12
<212> TYPE: PRT
<213> ORGANISM: Yellow Croaker

<400> SEQUENCE: 157

Gly Pro Ser Gly Glu Pro Gly Lys Pro Gly Glu Lys
1               5                   10

<210> SEQ ID NO 158
<211> LENGTH: 12
<212> TYPE: PRT
<213> ORGANISM: Yellow Croaker

<400> SEQUENCE: 158

Glu Gly Pro Ala Gly Pro Ala Gly Gln Asp Gly Arg
1               5                   10

<210> SEQ ID NO 159
<211> LENGTH: 12
<212> TYPE: PRT
<213> ORGANISM: Yellow Croaker

<400> SEQUENCE: 159

Gly Leu Ala Gly Asp Pro Gly Val Gln Gly Val Lys
1               5                   10

<210> SEQ ID NO 160
<211> LENGTH: 13
<212> TYPE: PRT
<213> ORGANISM: Yellow Croaker

<400> SEQUENCE: 160

Ala Gly Gly His Gly Gly Met Gly Ala Pro Gly Ala Arg
1               5                   10

<210> SEQ ID NO 161
<211> LENGTH: 9
<212> TYPE: PRT
<213> ORGANISM: Yellow Croaker

<400> SEQUENCE: 161

Asp Tyr Glu Val Asp Ala Thr Ile Lys
1               5

<210> SEQ ID NO 162
<211> LENGTH: 9
```

<212> TYPE: PRT
<213> ORGANISM: Yellow Croaker

<400> SEQUENCE: 162

Met His Cys Val Val Leu Gly Pro Arg
1               5

<210> SEQ ID NO 163
<211> LENGTH: 8
<212> TYPE: PRT
<213> ORGANISM: Yellow Croaker

<400> SEQUENCE: 163

Val Phe Cys Asp Phe Thr Thr Arg
1               5

<210> SEQ ID NO 164
<211> LENGTH: 12
<212> TYPE: PRT
<213> ORGANISM: Yellow Croaker

<400> SEQUENCE: 164

Gly Pro Ala Gly Ala Pro Gly Ser Asp Gly Gly Lys
1               5                   10

<210> SEQ ID NO 165
<211> LENGTH: 11
<212> TYPE: PRT
<213> ORGANISM: Yellow Croaker

<400> SEQUENCE: 165

Gly Pro Ala Gly Pro His Gly Pro Ala Gly Lys
1               5                   10

<210> SEQ ID NO 166
<211> LENGTH: 10
<212> TYPE: PRT
<213> ORGANISM: Yellow Croaker

<400> SEQUENCE: 166

Thr Gly Pro Val Gly Met Pro Gly Ala Arg
1               5                   10

<210> SEQ ID NO 167
<211> LENGTH: 10
<212> TYPE: PRT
<213> ORGANISM: Yellow Croaker

<400> SEQUENCE: 167

Thr Gly Pro Pro Gly Pro Thr Gly Pro Arg
1               5                   10

<210> SEQ ID NO 168
<211> LENGTH: 10
<212> TYPE: PRT
<213> ORGANISM: Yellow Croaker

<400> SEQUENCE: 168

Ala Gly Glu Pro Gly Ala Ala Gly Leu Arg
1               5                   10

<210> SEQ ID NO 169
<211> LENGTH: 10
<212> TYPE: PRT
<213> ORGANISM: Yellow Croaker

<400> SEQUENCE: 169

Val Gly Pro Ala Gly Ser Pro Gly Ala Arg
1               5                   10

<210> SEQ ID NO 170
<211> LENGTH: 7
<212> TYPE: PRT
<213> ORGANISM: Yellow Croaker

<400> SEQUENCE: 170

His Thr Gly Glu Trp Ser Lys
1               5

<210> SEQ ID NO 171
<211> LENGTH: 8
<212> TYPE: PRT
<213> ORGANISM: Yellow Croaker

<400> SEQUENCE: 171

Gly Tyr Thr Gly Leu Asp Gly Arg
1               5

<210> SEQ ID NO 172
<211> LENGTH: 10
<212> TYPE: PRT
<213> ORGANISM: Yellow Croaker

<400> SEQUENCE: 172

Ala Gly Pro Ala Gly Pro Ala Gly Ala Arg
1               5                   10

<210> SEQ ID NO 173
<211> LENGTH: 9
<212> TYPE: PRT
<213> ORGANISM: Yellow Croaker

<400> SEQUENCE: 173

Gly Ala Pro Gly Pro Gln Gly Ala Arg
1               5

<210> SEQ ID NO 174
<211> LENGTH: 9
<212> TYPE: PRT
<213> ORGANISM: Yellow Croaker

<400> SEQUENCE: 174

Gly Ala Thr Gly Pro Ala Gly Leu Arg
1               5

<210> SEQ ID NO 175
<211> LENGTH: 9
<212> TYPE: PRT
<213> ORGANISM: Yellow Croaker

<400> SEQUENCE: 175

Gly Glu Pro Gly Ala Ala Gly Pro Lys
1               5

<210> SEQ ID NO 176
<211> LENGTH: 6
<212> TYPE: PRT
<213> ORGANISM: Yellow Croaker

<400> SEQUENCE: 176

```
Thr Val Ile Glu Tyr Arg
1               5

<210> SEQ ID NO 177
<211> LENGTH: 9
<212> TYPE: PRT
<213> ORGANISM: Yellow Croaker

<400> SEQUENCE: 177

Gly Ala Pro Gly Pro Ala Gly Pro Arg
1               5

<210> SEQ ID NO 178
<211> LENGTH: 9
<212> TYPE: PRT
<213> ORGANISM: Yellow Croaker

<400> SEQUENCE: 178

Gly Ser Thr Gly Ala Ala Gly Pro Arg
1               5

<210> SEQ ID NO 179
<211> LENGTH: 7
<212> TYPE: PRT
<213> ORGANISM: Yellow Croaker

<400> SEQUENCE: 179

Ala Asp Gln Pro Ala Leu Arg
1               5

<210> SEQ ID NO 180
<211> LENGTH: 8
<212> TYPE: PRT
<213> ORGANISM: Yellow Croaker

<400> SEQUENCE: 180

Gly Pro Asp Gly Asn Ser Gly Arg
1               5

<210> SEQ ID NO 181
<211> LENGTH: 8
<212> TYPE: PRT
<213> ORGANISM: Yellow Croaker

<400> SEQUENCE: 181

Gly Leu Pro Gly Ala Glu Gly Arg
1               5

<210> SEQ ID NO 182
<211> LENGTH: 8
<212> TYPE: PRT
<213> ORGANISM: Yellow Croaker

<400> SEQUENCE: 182

Gly Pro Gln Gly Pro Asn Gly Lys
1               5

<210> SEQ ID NO 183
<211> LENGTH: 8
<212> TYPE: PRT
<213> ORGANISM: Yellow Croaker

<400> SEQUENCE: 183

Gly Pro Pro Gly Asp Ala Gly Arg
```

```
1               5
```

<210> SEQ ID NO 184
<211> LENGTH: 9
<212> TYPE: PRT
<213> ORGANISM: Yellow Croaker

<400> SEQUENCE: 184

```
Gly Ala Ala Gly Pro Pro Gly Gly Lys
1               5
```

<210> SEQ ID NO 185
<211> LENGTH: 6
<212> TYPE: PRT
<213> ORGANISM: Yellow Croaker

<400> SEQUENCE: 185

```
Thr Asn Lys Pro Ser Arg
1               5
```

<210> SEQ ID NO 186
<211> LENGTH: 8
<212> TYPE: PRT
<213> ORGANISM: Yellow Croaker

<400> SEQUENCE: 186

```
Gly Pro Pro Gly Pro Ala Gly Lys
1               5
```

<210> SEQ ID NO 187
<211> LENGTH: 6
<212> TYPE: PRT
<213> ORGANISM: Yellow Croaker

<400> SEQUENCE: 187

```
Gly Glu Pro Gly His Arg
1               5
```

<210> SEQ ID NO 188
<211> LENGTH: 6
<212> TYPE: PRT
<213> ORGANISM: Yellow Croaker

<400> SEQUENCE: 188

```
Ala Glu Gly Asn Ser Arg
1               5
```

<210> SEQ ID NO 189
<211> LENGTH: 4
<212> TYPE: PRT
<213> ORGANISM: Yellow Croaker

<400> SEQUENCE: 189

```
Asn Trp Phe Arg
1
```

<210> SEQ ID NO 190
<211> LENGTH: 6
<212> TYPE: PRT
<213> ORGANISM: Yellow Croaker

<400> SEQUENCE: 190

```
Gly Leu Ala Gly Glu Arg
1               5
```

<210> SEQ ID NO 191
<211> LENGTH: 6
<212> TYPE: PRT
<213> ORGANISM: Yellow Croaker

<400> SEQUENCE: 191

Gly Val Ala Gly Glu Arg
1               5

<210> SEQ ID NO 192
<211> LENGTH: 6
<212> TYPE: PRT
<213> ORGANISM: Yellow Croaker

<400> SEQUENCE: 192

Gly Ala Pro Gly Glu Arg
1               5

<210> SEQ ID NO 193
<211> LENGTH: 6
<212> TYPE: PRT
<213> ORGANISM: Yellow Croaker

<400> SEQUENCE: 193

Gly Asp Ala Gly Pro Lys
1               5

<210> SEQ ID NO 194
<211> LENGTH: 5
<212> TYPE: PRT
<213> ORGANISM: Yellow Croaker

<400> SEQUENCE: 194

Ser Thr Glu Ala Lys
1               5

<210> SEQ ID NO 195
<211> LENGTH: 6
<212> TYPE: PRT
<213> ORGANISM: Yellow Croaker

<400> SEQUENCE: 195

Gly Ala Pro Gly Gly Arg
1               5

<210> SEQ ID NO 196
<211> LENGTH: 6
<212> TYPE: PRT
<213> ORGANISM: Yellow Croaker

<400> SEQUENCE: 196

Gly Pro Ser Gly Gly Lys
1               5

<210> SEQ ID NO 197
<211> LENGTH: 4
<212> TYPE: PRT
<213> ORGANISM: Yellow Croaker

<400> SEQUENCE: 197

Asn Pro Ala Arg
1

<210> SEQ ID NO 198

```
<211> LENGTH: 4
<212> TYPE: PRT
<213> ORGANISM: Yellow Croaker

<400> SEQUENCE: 198

Asp Gly Pro Arg
1

<210> SEQ ID NO 199
<211> LENGTH: 4
<212> TYPE: PRT
<213> ORGANISM: Yellow Croaker

<400> SEQUENCE: 199

Asp Gly Ala Arg
1

<210> SEQ ID NO 200
<211> LENGTH: 3
<212> TYPE: PRT
<213> ORGANISM: Yellow Croaker

<400> SEQUENCE: 200

Asp Ile Arg
1

<210> SEQ ID NO 201
<211> LENGTH: 3
<212> TYPE: PRT
<213> ORGANISM: Yellow Croaker

<400> SEQUENCE: 201

Thr Cys Arg
1

<210> SEQ ID NO 202
<211> LENGTH: 3
<212> TYPE: PRT
<213> ORGANISM: Yellow Croaker

<400> SEQUENCE: 202

Gly His Arg
1

<210> SEQ ID NO 203
<211> LENGTH: 3
<212> TYPE: PRT
<213> ORGANISM: Yellow Croaker

<400> SEQUENCE: 203

Gly Glu Arg
1

<210> SEQ ID NO 204
<211> LENGTH: 4
<212> TYPE: PRT
<213> ORGANISM: Yellow Croaker

<400> SEQUENCE: 204

Ala Gly Gly Arg
1

<210> SEQ ID NO 205
<211> LENGTH: 3
<212> TYPE: PRT
```

<213> ORGANISM: Yellow Croaker

<400> SEQUENCE: 205

Gly Asp Arg
1

<210> SEQ ID NO 206
<211> LENGTH: 3
<212> TYPE: PRT
<213> ORGANISM: Yellow Croaker

<400> SEQUENCE: 206

Asp Gly Arg
1

<210> SEQ ID NO 207
<211> LENGTH: 3
<212> TYPE: PRT
<213> ORGANISM: Yellow Croaker

<400> SEQUENCE: 207

Gly Leu Arg
1

<210> SEQ ID NO 208
<211> LENGTH: 3
<212> TYPE: PRT
<213> ORGANISM: Yellow Croaker

<400> SEQUENCE: 208

Gly Met Lys
1

<210> SEQ ID NO 209
<211> LENGTH: 3
<212> TYPE: PRT
<213> ORGANISM: Yellow Croaker

<400> SEQUENCE: 209

Gly Glu Lys
1

<210> SEQ ID NO 210
<211> LENGTH: 3
<212> TYPE: PRT
<213> ORGANISM: Yellow Croaker

<400> SEQUENCE: 210

Gly Pro Arg
1

<210> SEQ ID NO 211
<211> LENGTH: 3
<212> TYPE: PRT
<213> ORGANISM: Yellow Croaker

<400> SEQUENCE: 211

Gly Asp Lys
1

<210> SEQ ID NO 212
<211> LENGTH: 3
<212> TYPE: PRT
<213> ORGANISM: Yellow Croaker

<400> SEQUENCE: 212

Gly Ala Arg
1

<210> SEQ ID NO 213
<211> LENGTH: 2
<212> TYPE: PRT
<213> ORGANISM: Yellow Croaker

<400> SEQUENCE: 213

Gly Arg
1

<210> SEQ ID NO 214
<211> LENGTH: 2
<212> TYPE: PRT
<213> ORGANISM: Yellow Croaker

<400> SEQUENCE: 214

Ala Lys
1

<210> SEQ ID NO 215
<211> LENGTH: 48
<212> TYPE: PRT
<213> ORGANISM: Yellow Croaker

<400> SEQUENCE: 215

Met Ile Leu Val Pro Phe Leu Cys Ile Met Leu Ser Tyr Met Ala Val
1               5                   10                  15

Gly Gln Glu Cys Ser Gly Gln Cys Ser Cys Pro Ser Thr Pro Pro Gln
            20                  25                  30

Cys Arg Pro Gly Val Ser Leu Val Leu Asp Gly Cys Gly Cys Cys Arg
        35                  40                  45

<210> SEQ ID NO 216
<211> LENGTH: 24
<212> TYPE: PRT
<213> ORGANISM: Yellow Croaker

<400> SEQUENCE: 216

Cys Cys Glu Glu Trp Glu Cys Asp Ser Pro Tyr Arg Pro Thr Phe Met
1               5                   10                  15

Gly Ser Ala Leu Ala Ala Tyr Arg
            20

<210> SEQ ID NO 217
<211> LENGTH: 21
<212> TYPE: PRT
<213> ORGANISM: Yellow Croaker

<400> SEQUENCE: 217

Ser Cys Ala Cys His His Asn Cys Pro Gly Glu Asn Asp Ile Phe Glu
1               5                   10                  15

Ser Met Tyr Tyr Lys
            20

<210> SEQ ID NO 218
<211> LENGTH: 21
<212> TYPE: PRT
<213> ORGANISM: Yellow Croaker

<400> SEQUENCE: 218

Tyr Gln Cys Thr Cys Leu Asp Gly Ala Val Gly Cys Val Pro Leu Cys
1               5                   10                  15

Ser Met Asp Val Arg
            20

<210> SEQ ID NO 219
<211> LENGTH: 16
<212> TYPE: PRT
<213> ORGANISM: Yellow Croaker

<400> SEQUENCE: 219

Leu Cys Met Val Arg Pro Cys Glu Ser Gln Leu Glu Gln Ser Ile Arg
1               5                   10                  15

<210> SEQ ID NO 220
<211> LENGTH: 15
<212> TYPE: PRT
<213> ORGANISM: Yellow Croaker

<400> SEQUENCE: 220

Glu Asn Cys Leu Val Gln Thr Thr Glu Trp Ser Ala Cys Ser Lys
1               5                   10                  15

<210> SEQ ID NO 221
<211> LENGTH: 13
<212> TYPE: PRT
<213> ORGANISM: Yellow Croaker

<400> SEQUENCE: 221

Glu Glu Glu Thr Tyr Gly Pro Asp Pro Ser Met Met Arg
1               5                   10

<210> SEQ ID NO 222
<211> LENGTH: 12
<212> TYPE: PRT
<213> ORGANISM: Yellow Croaker

<400> SEQUENCE: 222

Gly Leu Tyr Cys Asp Phe Gly Ala Pro Ile Asn Arg
1               5                   10

<210> SEQ ID NO 223
<211> LENGTH: 13
<212> TYPE: PRT
<213> ORGANISM: Yellow Croaker

<400> SEQUENCE: 223

Asp Gly Ala Thr Cys Val Phe Gly Gly Thr Val Tyr Lys
1               5                   10

<210> SEQ ID NO 224
<211> LENGTH: 10
<212> TYPE: PRT
<213> ORGANISM: Yellow Croaker

<400> SEQUENCE: 224

Leu Pro Ser Pro Asp Cys Pro Met Pro Arg
1               5                   10

<210> SEQ ID NO 225
<211> LENGTH: 10
<212> TYPE: PRT
<213> ORGANISM: Yellow Croaker

```
<400> SEQUENCE: 225

Phe Glu Ile Ser Gly Cys Thr Thr Thr Lys
1               5                   10

<210> SEQ ID NO 226
<211> LENGTH: 10
<212> TYPE: PRT
<213> ORGANISM: Yellow Croaker

<400> SEQUENCE: 226

Ser Gly Glu Thr Phe Gln Ser Ser Cys Lys
1               5                   10

<210> SEQ ID NO 227
<211> LENGTH: 9
<212> TYPE: PRT
<213> ORGANISM: Yellow Croaker

<400> SEQUENCE: 227

Thr Thr Thr Leu Pro Met Glu Phe Lys
1               5

<210> SEQ ID NO 228
<211> LENGTH: 9
<212> TYPE: PRT
<213> ORGANISM: Yellow Croaker

<400> SEQUENCE: 228

Gln Met Gly Glu Leu Cys Thr Glu Lys
1               5

<210> SEQ ID NO 229
<211> LENGTH: 9
<212> TYPE: PRT
<213> ORGANISM: Yellow Croaker

<400> SEQUENCE: 229

Phe Cys Gly Val Cys Leu Asp Gly Arg
1               5

<210> SEQ ID NO 230
<211> LENGTH: 9
<212> TYPE: PRT
<213> ORGANISM: Yellow Croaker

<400> SEQUENCE: 230

Thr Cys Gly Leu Gly Ile Ser Thr Arg
1               5

<210> SEQ ID NO 231
<211> LENGTH: 8
<212> TYPE: PRT
<213> ORGANISM: Yellow Croaker

<400> SEQUENCE: 231

Cys Pro Asp Gly Gln Val Met Lys
1               5

<210> SEQ ID NO 232
<211> LENGTH: 7
<212> TYPE: PRT
<213> ORGANISM: Yellow Croaker

<400> SEQUENCE: 232
```

Asp Leu Cys Asp Pro His Lys
1               5

<210> SEQ ID NO 233
<211> LENGTH: 6
<212> TYPE: PRT
<213> ORGANISM: Yellow Croaker

<400> SEQUENCE: 233

His Met Met Phe Ile Lys
1               5

<210> SEQ ID NO 234
<211> LENGTH: 7
<212> TYPE: PRT
<213> ORGANISM: Yellow Croaker

<400> SEQUENCE: 234

Ile Gly Val Cys Thr Ala Arg
1               5

<210> SEQ ID NO 235
<211> LENGTH: 6
<212> TYPE: PRT
<213> ORGANISM: Yellow Croaker

<400> SEQUENCE: 235

Val Thr Asn Asp Asn Arg
1               5

<210> SEQ ID NO 236
<211> LENGTH: 6
<212> TYPE: PRT
<213> ORGANISM: Yellow Croaker

<400> SEQUENCE: 236

Cys Cys Thr Pro His Arg
1               5

<210> SEQ ID NO 237
<211> LENGTH: 6
<212> TYPE: PRT
<213> ORGANISM: Yellow Croaker

<400> SEQUENCE: 237

Leu Ser Lys Pro Met Lys
1               5

<210> SEQ ID NO 238
<211> LENGTH: 6
<212> TYPE: PRT
<213> ORGANISM: Yellow Croaker

<400> SEQUENCE: 238

Met Met Gly Asp Met Ala
1               5

<210> SEQ ID NO 239
<211> LENGTH: 5
<212> TYPE: PRT
<213> ORGANISM: Yellow Croaker

<400> SEQUENCE: 239

Ser Tyr Arg Pro Lys
1               5

```
<210> SEQ ID NO 240
<211> LENGTH: 6
<212> TYPE: PRT
<213> ORGANISM: Yellow Croaker

<400> SEQUENCE: 240

Met Ser Ala Gly Met Lys
1               5

<210> SEQ ID NO 241
<211> LENGTH: 4
<212> TYPE: PRT
<213> ORGANISM: Yellow Croaker

<400> SEQUENCE: 241

Val Cys Ala Lys
1

<210> SEQ ID NO 242
<211> LENGTH: 3
<212> TYPE: PRT
<213> ORGANISM: Yellow Croaker

<400> SEQUENCE: 242

Gln Thr Arg
1

<210> SEQ ID NO 243
<211> LENGTH: 4
<212> TYPE: PRT
<213> ORGANISM: Yellow Croaker

<400> SEQUENCE: 243

Val Pro Gly Lys
1

<210> SEQ ID NO 244
<211> LENGTH: 3
<212> TYPE: PRT
<213> ORGANISM: Yellow Croaker

<400> SEQUENCE: 244

Asp Cys Arg
1

<210> SEQ ID NO 245
<211> LENGTH: 3
<212> TYPE: PRT
<213> ORGANISM: Yellow Croaker

<400> SEQUENCE: 245

Cys Ile Arg
1

<210> SEQ ID NO 246
<211> LENGTH: 3
<212> TYPE: PRT
<213> ORGANISM: Yellow Croaker

<400> SEQUENCE: 246

Leu Glu Lys
1
```

```
<210> SEQ ID NO 247
<211> LENGTH: 3
<212> TYPE: PRT
<213> ORGANISM: Yellow Croaker

<400> SEQUENCE: 247

Thr Pro Arg
1

<210> SEQ ID NO 248
<211> LENGTH: 2
<212> TYPE: PRT
<213> ORGANISM: Yellow Croaker

<400> SEQUENCE: 248

Val Lys
1

<210> SEQ ID NO 249
<211> LENGTH: 2
<212> TYPE: PRT
<213> ORGANISM: Yellow Croaker

<400> SEQUENCE: 249

Gly Lys
1

<210> SEQ ID NO 250
<211> LENGTH: 32
<212> TYPE: PRT
<213> ORGANISM: Yellow Croaker

<400> SEQUENCE: 250

Gln Ser Gly Phe Leu Asp Phe Met Met Glu Asp Asp Pro Gly Ser Gly
1               5                   10                  15

Asp Glu Ile Thr Glu Thr Ala Phe Ala Pro Val Pro Glu Gly Pro Lys
            20                  25                  30

<210> SEQ ID NO 251
<211> LENGTH: 24
<212> TYPE: PRT
<213> ORGANISM: Yellow Croaker

<400> SEQUENCE: 251

Ala Met Tyr Ser Gly Ile Ser Leu Phe Ser Asn Pro Val Pro Tyr Trp
1               5                   10                  15

Glu Val Gln Pro Val Thr Phe Arg
            20

<210> SEQ ID NO 252
<211> LENGTH: 23
<212> TYPE: PRT
<213> ORGANISM: Yellow Croaker

<400> SEQUENCE: 252

Leu Gly Leu Ser Phe Asn Glu Ile Ser Ser Val Glu Asn Gly Thr Leu
1               5                   10                  15

Ala Asn Val Pro His Leu Arg
            20

<210> SEQ ID NO 253
<211> LENGTH: 20
<212> TYPE: PRT
<213> ORGANISM: Yellow Croaker
```

```
<400> SEQUENCE: 253

Glu Leu His Leu Asp Asn Asn Ala Leu Thr Ser Val Pro Pro Gly Leu
1               5                   10                  15

Ser Asp His Lys
            20

<210> SEQ ID NO 254
<211> LENGTH: 20
<212> TYPE: PRT
<213> ORGANISM: Yellow Croaker

<400> SEQUENCE: 254

Ala Ser Phe Gln Gly Met Ser His Val Ile Val Met Glu Leu Gly Ser
1               5                   10                  15

Asn Pro Leu Lys
            20

<210> SEQ ID NO 255
<211> LENGTH: 18
<212> TYPE: PRT
<213> ORGANISM: Yellow Croaker

<400> SEQUENCE: 255

Ser Ala Cys Leu Ser Leu Leu Val Thr Ala Cys Trp Ala Leu Pro
1               5                   10                  15

Phe Arg

<210> SEQ ID NO 256
<211> LENGTH: 15
<212> TYPE: PRT
<213> ORGANISM: Yellow Croaker

<400> SEQUENCE: 256

Asp Ile Pro Asp Asp Thr Thr Leu Leu Asp Leu Gln Asn Asn Lys
1               5                   10                  15

<210> SEQ ID NO 257
<211> LENGTH: 17
<212> TYPE: PRT
<213> ORGANISM: Yellow Croaker

<400> SEQUENCE: 257

Ile Ala Ala Val Gly Thr Gly Asp Phe Cys Pro Pro Gly Leu Asn Ser
1               5                   10                  15

Lys

<210> SEQ ID NO 258
<211> LENGTH: 15
<212> TYPE: PRT
<213> ORGANISM: Yellow Croaker

<400> SEQUENCE: 258

Gly Leu Pro Thr Ser Leu Ser Glu Leu His Leu Asp Gly Asn Lys
1               5                   10                  15

<210> SEQ ID NO 259
<211> LENGTH: 11
<212> TYPE: PRT
<213> ORGANISM: Yellow Croaker

<400> SEQUENCE: 259
```

Tyr Ile Gln Val Val Tyr Leu His Ala Asn Lys
1               5                   10

<210> SEQ ID NO 260
<211> LENGTH: 13
<212> TYPE: PRT
<213> ORGANISM: Yellow Croaker

<400> SEQUENCE: 260

Ser Ala Gly Ile Asp Gly Gly Ala Phe Ala Asp Leu Lys
1               5                   10

<210> SEQ ID NO 261
<211> LENGTH: 11
<212> TYPE: PRT
<213> ORGANISM: Yellow Croaker

<400> SEQUENCE: 261

Ile Ala Asp Thr Asn Ile Thr Glu Ile Pro Lys
1               5                   10

<210> SEQ ID NO 262
<211> LENGTH: 11
<212> TYPE: PRT
<213> ORGANISM: Yellow Croaker

<400> SEQUENCE: 262

Gly Leu His Ala Leu Ile Leu Val Asn Asn Lys
1               5                   10

<210> SEQ ID NO 263
<211> LENGTH: 10
<212> TYPE: PRT
<213> ORGANISM: Yellow Croaker

<400> SEQUENCE: 263

Val Ile Gln Cys Ser Asp Leu Gly Leu Lys
1               5                   10

<210> SEQ ID NO 264
<211> LENGTH: 9
<212> TYPE: PRT
<213> ORGANISM: Yellow Croaker

<400> SEQUENCE: 264

Ser Ala Ile Gln Leu Gly Asn Tyr Arg
1               5

<210> SEQ ID NO 265
<211> LENGTH: 10
<212> TYPE: PRT
<213> ORGANISM: Yellow Croaker

<400> SEQUENCE: 265

Met Thr Ala Gly Ser Leu Glu Gly Leu Lys
1               5                   10

<210> SEQ ID NO 266
<211> LENGTH: 8
<212> TYPE: PRT
<213> ORGANISM: Yellow Croaker

<400> SEQUENCE: 266

Ile His Glu Asn Glu Ile Thr Lys
1               5

```
<210> SEQ ID NO 267
<211> LENGTH: 8
<212> TYPE: PRT
<213> ORGANISM: Yellow Croaker

<400> SEQUENCE: 267

Glu Ile Pro Ala Asn Met Pro Lys
1               5

<210> SEQ ID NO 268
<211> LENGTH: 7
<212> TYPE: PRT
<213> ORGANISM: Yellow Croaker

<400> SEQUENCE: 268

Ile Thr Ile Ile His Ala Lys
1               5

<210> SEQ ID NO 269
<211> LENGTH: 6
<212> TYPE: PRT
<213> ORGANISM: Yellow Croaker

<400> SEQUENCE: 269

Cys Gln Cys His Leu Arg
1               5

<210> SEQ ID NO 270
<211> LENGTH: 6
<212> TYPE: PRT
<213> ORGANISM: Yellow Croaker

<400> SEQUENCE: 270

Ser Leu Gln Glu Leu Arg
1               5

<210> SEQ ID NO 271
<211> LENGTH: 7
<212> TYPE: PRT
<213> ORGANISM: Yellow Croaker

<400> SEQUENCE: 271

Ala Leu Ser Pro Leu Thr Lys
1               5

<210> SEQ ID NO 272
<211> LENGTH: 5
<212> TYPE: PRT
<213> ORGANISM: Yellow Croaker

<400> SEQUENCE: 272

Glu Asn Asp Phe Lys
1               5

<210> SEQ ID NO 273
<211> LENGTH: 5
<212> TYPE: PRT
<213> ORGANISM: Yellow Croaker

<400> SEQUENCE: 273

Cys Val Phe Asp Arg
1               5
```

```
<210> SEQ ID NO 274
<211> LENGTH: 5
<212> TYPE: PRT
<213> ORGANISM: Yellow Croaker

<400> SEQUENCE: 274

Val Ser Tyr Ile Arg
1               5

<210> SEQ ID NO 275
<211> LENGTH: 5
<212> TYPE: PRT
<213> ORGANISM: Yellow Croaker

<400> SEQUENCE: 275

Leu Tyr Leu Ser Lys
1               5

<210> SEQ ID NO 276
<211> LENGTH: 5
<212> TYPE: PRT
<213> ORGANISM: Yellow Croaker

<400> SEQUENCE: 276

Ile Thr Glu Ile Lys
1               5

<210> SEQ ID NO 277
<211> LENGTH: 4
<212> TYPE: PRT
<213> ORGANISM: Yellow Croaker

<400> SEQUENCE: 277

Cys Pro Phe Arg
1

<210> SEQ ID NO 278
<211> LENGTH: 4
<212> TYPE: PRT
<213> ORGANISM: Yellow Croaker

<400> SEQUENCE: 278

Asn Met Leu Lys
1

<210> SEQ ID NO 279
<211> LENGTH: 4
<212> TYPE: PRT
<213> ORGANISM: Yellow Croaker

<400> SEQUENCE: 279

Asn Leu Ala Lys
1

<210> SEQ ID NO 280
<211> LENGTH: 3
<212> TYPE: PRT
<213> ORGANISM: Yellow Croaker

<400> SEQUENCE: 280

Leu Gln Arg
1

<210> SEQ ID NO 281
<211> LENGTH: 4
```

```
<212> TYPE: PRT
<213> ORGANISM: Yellow Croaker

<400> SEQUENCE: 281

Ala Val Pro Lys
1

<210> SEQ ID NO 282
<211> LENGTH: 3
<212> TYPE: PRT
<213> ORGANISM: Yellow Croaker

<400> SEQUENCE: 282

Asn Leu Lys
1

<210> SEQ ID NO 283
<211> LENGTH: 3
<212> TYPE: PRT
<213> ORGANISM: Yellow Croaker

<400> SEQUENCE: 283

Ile Thr Lys
1

<210> SEQ ID NO 284
<211> LENGTH: 2
<212> TYPE: PRT
<213> ORGANISM: Yellow Croaker

<400> SEQUENCE: 284

Met Arg
1

<210> SEQ ID NO 285
<211> LENGTH: 2
<212> TYPE: PRT
<213> ORGANISM: Yellow Croaker

<400> SEQUENCE: 285

Ile Lys
1

<210> SEQ ID NO 286
<211> LENGTH: 24
<212> TYPE: PRT
<213> ORGANISM: Yellow Croaker

<400> SEQUENCE: 286

Pro Gly Lys Asn Gly Glu Asp Gly Glu Ser Gly Lys Pro Gly Arg Ser
1               5                   10                  15

Gly Glu Arg Gly Pro Pro Gly Ala
            20

<210> SEQ ID NO 287
<211> LENGTH: 23
<212> TYPE: PRT
<213> ORGANISM: Yellow Croaker

<400> SEQUENCE: 287

Gly Lys Gln Gly Pro Ser Gly Pro Gly Glu Arg Gly Pro Pro Gly
1               5                   10                  15

Pro Met Gly Pro Pro Gly Leu
            20
```

<210> SEQ ID NO 288
<211> LENGTH: 21
<212> TYPE: PRT
<213> ORGANISM: Yellow Croaker

<400> SEQUENCE: 288

Gln Gly Pro Pro Gly Pro Ser Gly Glu Glu Gly Lys Arg Gly Pro Arg
1               5                   10                  15

Gly Glu Pro Gly Ala
            20

<210> SEQ ID NO 289
<211> LENGTH: 19
<212> TYPE: PRT
<213> ORGANISM: Yellow Croaker

<400> SEQUENCE: 289

Pro Gly Pro Thr Gly Pro Pro Gly Pro Arg Gly Arg Ser Gly Glu Met
1               5                   10                  15

Gly Pro Ala

<210> SEQ ID NO 290
<211> LENGTH: 18
<212> TYPE: PRT
<213> ORGANISM: Yellow Croaker

<400> SEQUENCE: 290

Gly Pro Ser Gly Lys Glu Gly Pro Lys Gly Asn Arg Gly Glu Thr Gly
1               5                   10                  15

Pro Ala

<210> SEQ ID NO 291
<211> LENGTH: 19
<212> TYPE: PRT
<213> ORGANISM: Yellow Croaker

<400> SEQUENCE: 291

Thr Gly Met Gln Gly Pro Pro Gly Pro Ser Gly Pro Ser Gly Asp Gln
1               5                   10                  15

Gly Pro Ala

<210> SEQ ID NO 292
<211> LENGTH: 16
<212> TYPE: PRT
<213> ORGANISM: Yellow Croaker

<400> SEQUENCE: 292

Glu Gly Pro Lys Gly Glu Arg Gly Pro Lys Gly Glu Arg Gly Pro Ala
1               5                   10                  15

<210> SEQ ID NO 293
<211> LENGTH: 18
<212> TYPE: PRT
<213> ORGANISM: Yellow Croaker

<400> SEQUENCE: 293

Pro Gly Gln Pro Gly Met Pro Gly Pro Gly Pro Gly Pro Pro
1               5                   10                  15

Gly Leu

```
<210> SEQ ID NO 294
<211> LENGTH: 16
<212> TYPE: PRT
<213> ORGANISM: Yellow Croaker

<400> SEQUENCE: 294

Arg Gly Pro Pro Gly Glu Arg Gly Glu Ser Gly Pro Pro Gly Pro Ala
1               5                   10                  15

<210> SEQ ID NO 295
<211> LENGTH: 15
<212> TYPE: PRT
<213> ORGANISM: Yellow Croaker

<400> SEQUENCE: 295

Gly Pro Met Gly Pro Met Gly Pro Arg Gly Pro Pro Gly Pro Ala
1               5                   10                  15

<210> SEQ ID NO 296
<211> LENGTH: 13
<212> TYPE: PRT
<213> ORGANISM: Yellow Croaker

<400> SEQUENCE: 296

Gln Gly Glu Asp Asp His Thr Gly Gly Ser Cys Thr Leu
1               5                   10

<210> SEQ ID NO 297
<211> LENGTH: 14
<212> TYPE: PRT
<213> ORGANISM: Yellow Croaker

<400> SEQUENCE: 297

Gly Pro Lys Gly Asp Arg Gly Glu Thr Gly Pro Asn Gly Ala
1               5                   10

<210> SEQ ID NO 298
<211> LENGTH: 15
<212> TYPE: PRT
<213> ORGANISM: Yellow Croaker

<400> SEQUENCE: 298

Gly Pro Pro Gly Pro Ser Gly Asn Pro Gly Pro Pro Gly Pro Ala
1               5                   10                  15

<210> SEQ ID NO 299
<211> LENGTH: 11
<212> TYPE: PRT
<213> ORGANISM: Yellow Croaker

<400> SEQUENCE: 299

Gly Glu Arg Gly Met Lys Gly His Arg Gly Phe
1               5                   10

<210> SEQ ID NO 300
<211> LENGTH: 14
<212> TYPE: PRT
<213> ORGANISM: Yellow Croaker

<400> SEQUENCE: 300

Gly Pro Pro Gly Thr Pro Gly Glu Lys Gly Ser Pro Gly Ala
1               5                   10

<210> SEQ ID NO 301
<211> LENGTH: 11
```

-continued

<212> TYPE: PRT
<213> ORGANISM: Yellow Croaker

<400> SEQUENCE: 301

Arg Ser Pro Asp Gly Thr Arg Lys Asn Pro Ala
1               5                   10

<210> SEQ ID NO 302
<211> LENGTH: 11
<212> TYPE: PRT
<213> ORGANISM: Yellow Croaker

<400> SEQUENCE: 302

Glu Asp Gly Cys Thr Ser His Thr Gly Thr Trp
1               5                   10

<210> SEQ ID NO 303
<211> LENGTH: 11
<212> TYPE: PRT
<213> ORGANISM: Yellow Croaker

<400> SEQUENCE: 303

Cys Glu Asp Thr Thr Asp Cys Pro Asn Pro Val
1               5                   10

<210> SEQ ID NO 304
<211> LENGTH: 12
<212> TYPE: PRT
<213> ORGANISM: Yellow Croaker

<400> SEQUENCE: 304

Thr Gly Glu Pro Gly Arg Thr Gly Glu Pro Gly Leu
1               5                   10

<210> SEQ ID NO 305
<211> LENGTH: 12
<212> TYPE: PRT
<213> ORGANISM: Yellow Croaker

<400> SEQUENCE: 305

Gly Lys Asn Gly Asp Arg Gly Glu Thr Gly Pro Ala
1               5                   10

<210> SEQ ID NO 306
<211> LENGTH: 12
<212> TYPE: PRT
<213> ORGANISM: Yellow Croaker

<400> SEQUENCE: 306

Gly Gln Asp Gly Arg Pro Gly Pro Pro Gly Thr Val
1               5                   10

<210> SEQ ID NO 307
<211> LENGTH: 10
<212> TYPE: PRT
<213> ORGANISM: Yellow Croaker

<400> SEQUENCE: 307

Cys Asn Met Glu Thr Gly Glu Thr Cys Val
1               5                   10

<210> SEQ ID NO 308
<211> LENGTH: 12
<212> TYPE: PRT
<213> ORGANISM: Yellow Croaker

```
<400> SEQUENCE: 308

Pro Gly Pro Arg Gly Pro Ser Gly Pro Gln Gly Ala
1               5                   10

<210> SEQ ID NO 309
<211> LENGTH: 12
<212> TYPE: PRT
<213> ORGANISM: Yellow Croaker

<400> SEQUENCE: 309

Lys Gly Met Thr Gly Ser Pro Gly Asn Pro Gly Ala
1               5                   10

<210> SEQ ID NO 310
<211> LENGTH: 11
<212> TYPE: PRT
<213> ORGANISM: Yellow Croaker

<400> SEQUENCE: 310

Gly Glu Thr Gly Lys Pro Gly Glu Gln Gly Leu
1               5                   10

<210> SEQ ID NO 311
<211> LENGTH: 12
<212> TYPE: PRT
<213> ORGANISM: Yellow Croaker

<400> SEQUENCE: 311

Thr Gly Pro Pro Gly Glu Pro Gly Glu Pro Gly Ala
1               5                   10

<210> SEQ ID NO 312
<211> LENGTH: 10
<212> TYPE: PRT
<213> ORGANISM: Yellow Croaker

<400> SEQUENCE: 312

Asp Pro Asp Gln Gly Cys Thr Gln Asp Ala
1               5                   10

<210> SEQ ID NO 313
<211> LENGTH: 11
<212> TYPE: PRT
<213> ORGANISM: Yellow Croaker

<400> SEQUENCE: 313

Gly Arg Glu Gly Thr Pro Gly Asn Glu Gly Ala
1               5                   10

<210> SEQ ID NO 314
<211> LENGTH: 11
<212> TYPE: PRT
<213> ORGANISM: Yellow Croaker

<400> SEQUENCE: 314

Gly Glu Gly Gly Lys Pro Gly Glu Arg Gly Val
1               5                   10

<210> SEQ ID NO 315
<211> LENGTH: 10
<212> TYPE: PRT
<213> ORGANISM: Yellow Croaker

<400> SEQUENCE: 315
```

Arg Gly Asp Lys Gly Glu Thr Gly Glu Ala
1               5                   10

<210> SEQ ID NO 316
<211> LENGTH: 11
<212> TYPE: PRT
<213> ORGANISM: Yellow Croaker

<400> SEQUENCE: 316

Gly Ser Pro Gly Lys Asp Gly Met Ser Gly Leu
1               5                   10

<210> SEQ ID NO 317
<211> LENGTH: 9
<212> TYPE: PRT
<213> ORGANISM: Yellow Croaker

<400> SEQUENCE: 317

Pro Gly Gln Arg Gly Glu Arg Gly Phe
1               5

<210> SEQ ID NO 318
<211> LENGTH: 10
<212> TYPE: PRT
<213> ORGANISM: Yellow Croaker

<400> SEQUENCE: 318

Arg Gly Glu Pro Gly Asn Pro Gly Pro Ala
1               5                   10

<210> SEQ ID NO 319
<211> LENGTH: 9
<212> TYPE: PRT
<213> ORGANISM: Yellow Croaker

<400> SEQUENCE: 319

Arg Gly Asp Arg Gly Asp Gln Gly Ala
1               5

<210> SEQ ID NO 320
<211> LENGTH: 10
<212> TYPE: PRT
<213> ORGANISM: Yellow Croaker

<400> SEQUENCE: 320

Pro Gly Pro Lys Gly Asn Thr Gly Glu Ala
1               5                   10

<210> SEQ ID NO 321
<211> LENGTH: 8
<212> TYPE: PRT
<213> ORGANISM: Yellow Croaker

<400> SEQUENCE: 321

Lys Thr Ser Lys Thr Ser Arg Leu
1               5

<210> SEQ ID NO 322
<211> LENGTH: 7
<212> TYPE: PRT
<213> ORGANISM: Yellow Croaker

<400> SEQUENCE: 322

Lys Met Cys His Pro Asp Trp

-continued

```
<210> SEQ ID NO 323
<211> LENGTH: 9
<212> TYPE: PRT
<213> ORGANISM: Yellow Croaker

<400> SEQUENCE: 323

Gln Gly Met Pro Gly Glu Arg Gly Ala
1               5

<210> SEQ ID NO 324
<211> LENGTH: 11
<212> TYPE: PRT
<213> ORGANISM: Yellow Croaker

<400> SEQUENCE: 324

Gly Pro Pro Gly Pro Pro Gly Pro Pro Gly Ala
1               5                   10

<210> SEQ ID NO 325
<211> LENGTH: 9
<212> TYPE: PRT
<213> ORGANISM: Yellow Croaker

<400> SEQUENCE: 325

Gly Glu Arg Gly Glu Gln Gly Pro Ala
1               5

<210> SEQ ID NO 326
<211> LENGTH: 8
<212> TYPE: PRT
<213> ORGANISM: Yellow Croaker

<400> SEQUENCE: 326

Pro His Asp Glu Cys Cys Pro Val
1               5

<210> SEQ ID NO 327
<211> LENGTH: 9
<212> TYPE: PRT
<213> ORGANISM: Yellow Croaker

<400> SEQUENCE: 327

Pro Gly Lys Asp Gly Pro Arg Gly Leu
1               5

<210> SEQ ID NO 328
<211> LENGTH: 8
<212> TYPE: PRT
<213> ORGANISM: Yellow Croaker

<400> SEQUENCE: 328

Gly Ser Arg Gly Asp Arg Gly Phe
1               5

<210> SEQ ID NO 329
<211> LENGTH: 9
<212> TYPE: PRT
<213> ORGANISM: Yellow Croaker

<400> SEQUENCE: 329

Thr Gly Asp Lys Gly Glu Pro Gly Ala
1               5
```

```
<210> SEQ ID NO 330
<211> LENGTH: 8
<212> TYPE: PRT
<213> ORGANISM: Yellow Croaker

<400> SEQUENCE: 330

Ser Pro Gln Met Ser Gly Gly Tyr
1               5

<210> SEQ ID NO 331
<211> LENGTH: 7
<212> TYPE: PRT
<213> ORGANISM: Yellow Croaker

<400> SEQUENCE: 331

Lys Pro Glu Pro Cys Gln Ile
1               5

<210> SEQ ID NO 332
<211> LENGTH: 9
<212> TYPE: PRT
<213> ORGANISM: Yellow Croaker

<400> SEQUENCE: 332

Arg Gly Pro Ser Gly Pro Pro Gly Ala
1               5

<210> SEQ ID NO 333
<211> LENGTH: 9
<212> TYPE: PRT
<213> ORGANISM: Yellow Croaker

<400> SEQUENCE: 333

Gly Pro Lys Gly Glu Ser Gly Ser Ala
1               5

<210> SEQ ID NO 334
<211> LENGTH: 9
<212> TYPE: PRT
<213> ORGANISM: Yellow Croaker

<400> SEQUENCE: 334

Met Gly Pro Thr Gly Pro Thr Gly Ala
1               5

<210> SEQ ID NO 335
<211> LENGTH: 8
<212> TYPE: PRT
<213> ORGANISM: Yellow Croaker

<400> SEQUENCE: 335

Gly Arg Thr Gly Glu Met Gly Ala
1               5

<210> SEQ ID NO 336
<211> LENGTH: 6
<212> TYPE: PRT
<213> ORGANISM: Yellow Croaker

<400> SEQUENCE: 336

Lys Glu Lys Lys His Val
1               5

<210> SEQ ID NO 337
```

```
<210> SEQ ID NO 337
<211> LENGTH: 6
<212> TYPE: PRT
<213> ORGANISM: Yellow Croaker

<400> SEQUENCE: 337

Arg Thr Cys Arg Asp Leu
1               5

<210> SEQ ID NO 338
<211> LENGTH: 7
<212> TYPE: PRT
<213> ORGANISM: Yellow Croaker

<400> SEQUENCE: 338

Thr Pro Thr Gln Ser Glu Val
1               5

<210> SEQ ID NO 339
<211> LENGTH: 9
<212> TYPE: PRT
<213> ORGANISM: Yellow Croaker

<400> SEQUENCE: 339

Gly Pro Pro Gly Pro Thr Gly Pro Ala
1               5

<210> SEQ ID NO 340
<211> LENGTH: 7
<212> TYPE: PRT
<213> ORGANISM: Yellow Croaker

<400> SEQUENCE: 340

Pro Gly Glu Arg Gly Arg Ala
1               5

<210> SEQ ID NO 341
<211> LENGTH: 8
<212> TYPE: PRT
<213> ORGANISM: Yellow Croaker

<400> SEQUENCE: 341

Gly Pro Pro Gly Asn Asp Gly Ile
1               5

<210> SEQ ID NO 342
<211> LENGTH: 6
<212> TYPE: PRT
<213> ORGANISM: Yellow Croaker

<400> SEQUENCE: 342

Glu Gly Asn Ser Arg Phe
1               5

<210> SEQ ID NO 343
<211> LENGTH: 8
<212> TYPE: PRT
<213> ORGANISM: Yellow Croaker

<400> SEQUENCE: 343

Gly Glu Asn Gly Thr Pro Gly Ala
1               5

<210> SEQ ID NO 344
<211> LENGTH: 6
<212> TYPE: PRT
```

<213> ORGANISM: Yellow Croaker

<400> SEQUENCE: 344

Lys Gly His Arg Gly Phe
1               5

<210> SEQ ID NO 345
<211> LENGTH: 6
<212> TYPE: PRT
<213> ORGANISM: Yellow Croaker

<400> SEQUENCE: 345

Gln Pro Gln Glu Lys Ala
1               5

<210> SEQ ID NO 346
<211> LENGTH: 8
<212> TYPE: PRT
<213> ORGANISM: Yellow Croaker

<400> SEQUENCE: 346

Gly Ser Arg Gly Ser Pro Gly Ala
1               5

<210> SEQ ID NO 347
<211> LENGTH: 7
<212> TYPE: PRT
<213> ORGANISM: Yellow Croaker

<400> SEQUENCE: 347

Pro Gly Lys Asp Gly Asp Val
1               5

<210> SEQ ID NO 348
<211> LENGTH: 6
<212> TYPE: PRT
<213> ORGANISM: Yellow Croaker

<400> SEQUENCE: 348

His Cys Lys Asn Ser Val
1               5

<210> SEQ ID NO 349
<211> LENGTH: 5
<212> TYPE: PRT
<213> ORGANISM: Yellow Croaker

<400> SEQUENCE: 349

Arg Asp Arg Asp Leu
1               5

<210> SEQ ID NO 350
<211> LENGTH: 7
<212> TYPE: PRT
<213> ORGANISM: Yellow Croaker

<400> SEQUENCE: 350

Asp Gly Lys Thr Gly Pro Val
1               5

<210> SEQ ID NO 351
<211> LENGTH: 8
<212> TYPE: PRT
<213> ORGANISM: Yellow Croaker

```
<400> SEQUENCE: 351

Gly Pro Ser Gly Asn Pro Gly Ala
1               5

<210> SEQ ID NO 352
<211> LENGTH: 6
<212> TYPE: PRT
<213> ORGANISM: Yellow Croaker

<400> SEQUENCE: 352

Cys Pro Asp Asp Gly Phe
1               5

<210> SEQ ID NO 353
<211> LENGTH: 7
<212> TYPE: PRT
<213> ORGANISM: Yellow Croaker

<400> SEQUENCE: 353

Pro Gly Pro Gln Gly Pro Val
1               5

<210> SEQ ID NO 354
<211> LENGTH: 6
<212> TYPE: PRT
<213> ORGANISM: Yellow Croaker

<400> SEQUENCE: 354

Gln Gly Ser Asn Glu Ile
1               5

<210> SEQ ID NO 355
<211> LENGTH: 7
<212> TYPE: PRT
<213> ORGANISM: Yellow Croaker

<400> SEQUENCE: 355

Pro Gly Pro Ser Gly Glu Val
1               5

<210> SEQ ID NO 356
<211> LENGTH: 5
<212> TYPE: PRT
<213> ORGANISM: Yellow Croaker

<400> SEQUENCE: 356

Pro Asp Gln Glu Phe
1               5

<210> SEQ ID NO 357
<211> LENGTH: 6
<212> TYPE: PRT
<213> ORGANISM: Yellow Croaker

<400> SEQUENCE: 357

Asp Asp Lys Ser Pro Ala
1               5

<210> SEQ ID NO 358
<211> LENGTH: 7
<212> TYPE: PRT
<213> ORGANISM: Yellow Croaker

<400> SEQUENCE: 358
```

```
Lys Gly Asp Ser Gly Pro Ala
1               5

<210> SEQ ID NO 359
<211> LENGTH: 6
<212> TYPE: PRT
<213> ORGANISM: Yellow Croaker

<400> SEQUENCE: 359

Met Gly Pro Arg Gly Leu
1               5

<210> SEQ ID NO 360
<211> LENGTH: 6
<212> TYPE: PRT
<213> ORGANISM: Yellow Croaker

<400> SEQUENCE: 360

Arg Gly Gln Pro Gly Val
1               5

<210> SEQ ID NO 361
<211> LENGTH: 6
<212> TYPE: PRT
<213> ORGANISM: Yellow Croaker

<400> SEQUENCE: 361

Asn Gly Glu Arg Gly Ala
1               5

<210> SEQ ID NO 362
<211> LENGTH: 5
<212> TYPE: PRT
<213> ORGANISM: Yellow Croaker

<400> SEQUENCE: 362

Gln Glu Pro Gln Val
1               5

<210> SEQ ID NO 363
<211> LENGTH: 5
<212> TYPE: PRT
<213> ORGANISM: Yellow Croaker

<400> SEQUENCE: 363

Met Cys Asp Glu Val
1               5

<210> SEQ ID NO 364
<211> LENGTH: 6
<212> TYPE: PRT
<213> ORGANISM: Yellow Croaker

<400> SEQUENCE: 364

Ser Gly Pro Gln Gly Phe
1               5

<210> SEQ ID NO 365
<211> LENGTH: 6
<212> TYPE: PRT
<213> ORGANISM: Yellow Croaker

<400> SEQUENCE: 365

Pro Gly Gly Arg Gly Phe
1               5
```

```
<210> SEQ ID NO 366
<211> LENGTH: 7
<212> TYPE: PRT
<213> ORGANISM: Yellow Croaker

<400> SEQUENCE: 366

Pro Gly Ser Asp Gly Ser Ala
1               5

<210> SEQ ID NO 367
<211> LENGTH: 6
<212> TYPE: PRT
<213> ORGANISM: Yellow Croaker

<400> SEQUENCE: 367

Arg Gly Asn Asp Gly Ala
1               5

<210> SEQ ID NO 368
<211> LENGTH: 6
<212> TYPE: PRT
<213> ORGANISM: Yellow Croaker

<400> SEQUENCE: 368

Met Gly Pro Arg Gly Ala
1               5

<210> SEQ ID NO 369
<211> LENGTH: 6
<212> TYPE: PRT
<213> ORGANISM: Yellow Croaker

<400> SEQUENCE: 369

Pro Gly Glu Arg Gly Ala
1               5

<210> SEQ ID NO 370
<211> LENGTH: 6
<212> TYPE: PRT
<213> ORGANISM: Yellow Croaker

<400> SEQUENCE: 370

Pro Gly Glu Arg Gly Ala
1               5

<210> SEQ ID NO 371
<211> LENGTH: 5
<212> TYPE: PRT
<213> ORGANISM: Yellow Croaker

<400> SEQUENCE: 371

Lys Ser Gly Glu Tyr
1               5

<210> SEQ ID NO 372
<211> LENGTH: 6
<212> TYPE: PRT
<213> ORGANISM: Yellow Croaker

<400> SEQUENCE: 372

Cys Asp Ser Gly Thr Val
1               5
```

<210> SEQ ID NO 373
<211> LENGTH: 4
<212> TYPE: PRT
<213> ORGANISM: Yellow Croaker

<400> SEQUENCE: 373

Lys Lys Asn Trp
1

<210> SEQ ID NO 374
<211> LENGTH: 5
<212> TYPE: PRT
<213> ORGANISM: Yellow Croaker

<400> SEQUENCE: 374

Met Thr Asp Gly Phe
1               5

<210> SEQ ID NO 375
<211> LENGTH: 6
<212> TYPE: PRT
<213> ORGANISM: Yellow Croaker

<400> SEQUENCE: 375

Gln Gly Pro Pro Gly Leu
1               5

<210> SEQ ID NO 376
<211> LENGTH: 6
<212> TYPE: PRT
<213> ORGANISM: Yellow Croaker

<400> SEQUENCE: 376

Pro Gly Pro Gln Gly Ile
1               5

<210> SEQ ID NO 377
<211> LENGTH: 6
<212> TYPE: PRT
<213> ORGANISM: Yellow Croaker

<400> SEQUENCE: 377

Gly Pro Arg Gly Pro Ala
1               5

<210> SEQ ID NO 378
<211> LENGTH: 6
<212> TYPE: PRT
<213> ORGANISM: Yellow Croaker

<400> SEQUENCE: 378

Gly Ser Glu Gly Ser Leu
1               5

<210> SEQ ID NO 379
<211> LENGTH: 6
<212> TYPE: PRT
<213> ORGANISM: Yellow Croaker

<400> SEQUENCE: 379

Lys Gly Thr Asp Gly Ala
1               5

<210> SEQ ID NO 380
<211> LENGTH: 6

-continued

<212> TYPE: PRT
<213> ORGANISM: Yellow Croaker

<400> SEQUENCE: 380

Asp Gly Gln Pro Gly Ala
1               5

<210> SEQ ID NO 381
<211> LENGTH: 6
<212> TYPE: PRT
<213> ORGANISM: Yellow Croaker

<400> SEQUENCE: 381

Pro Gly Thr Pro Gly Leu
1               5

<210> SEQ ID NO 382
<211> LENGTH: 5
<212> TYPE: PRT
<213> ORGANISM: Yellow Croaker

<400> SEQUENCE: 382

Met Ser Thr Glu Ala
1               5

<210> SEQ ID NO 383
<211> LENGTH: 5
<212> TYPE: PRT
<213> ORGANISM: Yellow Croaker

<400> SEQUENCE: 383

Gly Gln Arg Gly Ile
1               5

<210> SEQ ID NO 384
<211> LENGTH: 6
<212> TYPE: PRT
<213> ORGANISM: Yellow Croaker

<400> SEQUENCE: 384

Thr Gly Pro Lys Gly Ala
1               5

<210> SEQ ID NO 385
<211> LENGTH: 6
<212> TYPE: PRT
<213> ORGANISM: Yellow Croaker

<400> SEQUENCE: 385

Pro Gly Asn Asp Gly Ala
1               5

<210> SEQ ID NO 386
<211> LENGTH: 6
<212> TYPE: PRT
<213> ORGANISM: Yellow Croaker

<400> SEQUENCE: 386

Pro Gly Pro Lys Gly Ala
1               5

<210> SEQ ID NO 387
<211> LENGTH: 6
<212> TYPE: PRT
<213> ORGANISM: Yellow Croaker

```
<400> SEQUENCE: 387

Pro Gly Pro Gln Gly Ala
1               5

<210> SEQ ID NO 388
<211> LENGTH: 6
<212> TYPE: PRT
<213> ORGANISM: Yellow Croaker

<400> SEQUENCE: 388

Lys Gly Glu Gly Gly Ala
1               5

<210> SEQ ID NO 389
<211> LENGTH: 6
<212> TYPE: PRT
<213> ORGANISM: Yellow Croaker

<400> SEQUENCE: 389

Gly Ser Pro Gly Glu Ala
1               5

<210> SEQ ID NO 390
<211> LENGTH: 4
<212> TYPE: PRT
<213> ORGANISM: Yellow Croaker

<400> SEQUENCE: 390

Asp Arg Asp Val
1

<210> SEQ ID NO 391
<211> LENGTH: 6
<212> TYPE: PRT
<213> ORGANISM: Yellow Croaker

<400> SEQUENCE: 391

Pro Gly Pro Pro Gly Ala
1               5

<210> SEQ ID NO 392
<211> LENGTH: 4
<212> TYPE: PRT
<213> ORGANISM: Yellow Croaker

<400> SEQUENCE: 392

Pro Asp Pro Tyr
1

<210> SEQ ID NO 393
<211> LENGTH: 4
<212> TYPE: PRT
<213> ORGANISM: Yellow Croaker

<400> SEQUENCE: 393

Ser Gln Gln Ile
1

<210> SEQ ID NO 394
<211> LENGTH: 5
<212> TYPE: PRT
<213> ORGANISM: Yellow Croaker

<400> SEQUENCE: 394
```

Gly Arg Asp Gly Ala
1               5

<210> SEQ ID NO 395
<211> LENGTH: 5
<212> TYPE: PRT
<213> ORGANISM: Yellow Croaker

<400> SEQUENCE: 395

Gly Pro Pro Gly Phe
1               5

<210> SEQ ID NO 396
<211> LENGTH: 3
<212> TYPE: PRT
<213> ORGANISM: Yellow Croaker

<400> SEQUENCE: 396

Arg Met Tyr
1

<210> SEQ ID NO 397
<211> LENGTH: 4
<212> TYPE: PRT
<213> ORGANISM: Yellow Croaker

<400> SEQUENCE: 397

Ser Lys Asn Ile
1

<210> SEQ ID NO 398
<211> LENGTH: 4
<212> TYPE: PRT
<213> ORGANISM: Yellow Croaker

<400> SEQUENCE: 398

Ser Gln Asn Ile
1

<210> SEQ ID NO 399
<211> LENGTH: 4
<212> TYPE: PRT
<213> ORGANISM: Yellow Croaker

<400> SEQUENCE: 399

Pro Met Asp Val
1

<210> SEQ ID NO 400
<211> LENGTH: 4
<212> TYPE: PRT
<213> ORGANISM: Yellow Croaker

<400> SEQUENCE: 400

Pro Glu Asp Val
1

<210> SEQ ID NO 401
<211> LENGTH: 6
<212> TYPE: PRT
<213> ORGANISM: Yellow Croaker

<400> SEQUENCE: 401

Pro Gly Gly Pro Gly Ala

```
1               5

<210> SEQ ID NO 402
<211> LENGTH: 5
<212> TYPE: PRT
<213> ORGANISM: Yellow Croaker

<400> SEQUENCE: 402

Gly Glu Asn Gly Ala
1               5

<210> SEQ ID NO 403
<211> LENGTH: 5
<212> TYPE: PRT
<213> ORGANISM: Yellow Croaker

<400> SEQUENCE: 403

Gly Gly Arg Gly Val
1               5

<210> SEQ ID NO 404
<211> LENGTH: 5
<212> TYPE: PRT
<213> ORGANISM: Yellow Croaker

<400> SEQUENCE: 404

Gly Gly Pro Gly Phe
1               5

<210> SEQ ID NO 405
<211> LENGTH: 5
<212> TYPE: PRT
<213> ORGANISM: Yellow Croaker

<400> SEQUENCE: 405

Pro Gly Gly Gly Phe
1               5

<210> SEQ ID NO 406
<211> LENGTH: 5
<212> TYPE: PRT
<213> ORGANISM: Yellow Croaker

<400> SEQUENCE: 406

Gly Pro Lys Gly Ala
1               5

<210> SEQ ID NO 407
<211> LENGTH: 5
<212> TYPE: PRT
<213> ORGANISM: Yellow Croaker

<400> SEQUENCE: 407

Gly Pro Lys Gly Ala
1               5

<210> SEQ ID NO 408
<211> LENGTH: 5
<212> TYPE: PRT
<213> ORGANISM: Yellow Croaker

<400> SEQUENCE: 408

Gly Pro Gln Gly Ala
1               5
```

<210> SEQ ID NO 409
<211> LENGTH: 5
<212> TYPE: PRT
<213> ORGANISM: Yellow Croaker

<400> SEQUENCE: 409

Gly Asn Thr Gly Ala
1               5

<210> SEQ ID NO 410
<211> LENGTH: 4
<212> TYPE: PRT
<213> ORGANISM: Yellow Croaker

<400> SEQUENCE: 410

Asp Gly Gln Val
1

<210> SEQ ID NO 411
<211> LENGTH: 4
<212> TYPE: PRT
<213> ORGANISM: Yellow Croaker

<400> SEQUENCE: 411

Asp Gly Thr Leu
1

<210> SEQ ID NO 412
<211> LENGTH: 4
<212> TYPE: PRT
<213> ORGANISM: Yellow Croaker

<400> SEQUENCE: 412

Gly Lys Thr Val
1

<210> SEQ ID NO 413
<211> LENGTH: 4
<212> TYPE: PRT
<213> ORGANISM: Yellow Croaker

<400> SEQUENCE: 413

Lys Gly Glu Ala
1

<210> SEQ ID NO 414
<211> LENGTH: 4
<212> TYPE: PRT
<213> ORGANISM: Yellow Croaker

<400> SEQUENCE: 414

Lys Gly Glu Ala
1

<210> SEQ ID NO 415
<211> LENGTH: 5
<212> TYPE: PRT
<213> ORGANISM: Yellow Croaker

<400> SEQUENCE: 415

Gly Pro Thr Gly Ala
1               5

<210> SEQ ID NO 416

```
<211> LENGTH: 5
<212> TYPE: PRT
<213> ORGANISM: Yellow Croaker

<400> SEQUENCE: 416

Gly Pro Pro Gly Ala
1               5

<210> SEQ ID NO 417
<211> LENGTH: 5
<212> TYPE: PRT
<213> ORGANISM: Yellow Croaker

<400> SEQUENCE: 417

Gly Pro Pro Gly Ala
1               5

<210> SEQ ID NO 418
<211> LENGTH: 4
<212> TYPE: PRT
<213> ORGANISM: Yellow Croaker

<400> SEQUENCE: 418

Gly Gly Asn Phe
1

<210> SEQ ID NO 419
<211> LENGTH: 4
<212> TYPE: PRT
<213> ORGANISM: Yellow Croaker

<400> SEQUENCE: 419

Lys Gly Asp Ala
1

<210> SEQ ID NO 420
<211> LENGTH: 4
<212> TYPE: PRT
<213> ORGANISM: Yellow Croaker

<400> SEQUENCE: 420

Lys Gly Asp Ala
1

<210> SEQ ID NO 421
<211> LENGTH: 4
<212> TYPE: PRT
<213> ORGANISM: Yellow Croaker

<400> SEQUENCE: 421

Lys Gly Asp Ala
1

<210> SEQ ID NO 422
<211> LENGTH: 3
<212> TYPE: PRT
<213> ORGANISM: Yellow Croaker

<400> SEQUENCE: 422

Glu Gln Ile
1

<210> SEQ ID NO 423
<211> LENGTH: 5
<212> TYPE: PRT
```

<213> ORGANISM: Yellow Croaker

<400> SEQUENCE: 423

Gly Pro Ser Gly Ala
1               5

<210> SEQ ID NO 424
<211> LENGTH: 4
<212> TYPE: PRT
<213> ORGANISM: Yellow Croaker

<400> SEQUENCE: 424

Thr Gly Pro Ile
1

<210> SEQ ID NO 425
<211> LENGTH: 3
<212> TYPE: PRT
<213> ORGANISM: Yellow Croaker

<400> SEQUENCE: 425

Arg Gly Phe
1

<210> SEQ ID NO 426
<211> LENGTH: 4
<212> TYPE: PRT
<213> ORGANISM: Yellow Croaker

<400> SEQUENCE: 426

Glu Gly Pro Ala
1

<210> SEQ ID NO 427
<211> LENGTH: 4
<212> TYPE: PRT
<213> ORGANISM: Yellow Croaker

<400> SEQUENCE: 427

Pro Gly Glu Ala
1

<210> SEQ ID NO 428
<211> LENGTH: 4
<212> TYPE: PRT
<213> ORGANISM: Yellow Croaker

<400> SEQUENCE: 428

Pro Gly Pro Val
1

<210> SEQ ID NO 429
<211> LENGTH: 3
<212> TYPE: PRT
<213> ORGANISM: Yellow Croaker

<400> SEQUENCE: 429

Met Gly Phe
1

<210> SEQ ID NO 430
<211> LENGTH: 3
<212> TYPE: PRT
<213> ORGANISM: Yellow Croaker

```
<400> SEQUENCE: 430

Lys Ser Leu
1

<210> SEQ ID NO 431
<211> LENGTH: 3
<212> TYPE: PRT
<213> ORGANISM: Yellow Croaker

<400> SEQUENCE: 431

Lys Lys Ala
1

<210> SEQ ID NO 432
<211> LENGTH: 3
<212> TYPE: PRT
<213> ORGANISM: Yellow Croaker

<400> SEQUENCE: 432

Met Pro Val
1

<210> SEQ ID NO 433
<211> LENGTH: 4
<212> TYPE: PRT
<213> ORGANISM: Yellow Croaker

<400> SEQUENCE: 433

Pro Gly Pro Ala
1

<210> SEQ ID NO 434
<211> LENGTH: 4
<212> TYPE: PRT
<213> ORGANISM: Yellow Croaker

<400> SEQUENCE: 434

Pro Gly Pro Ala
1

<210> SEQ ID NO 435
<211> LENGTH: 4
<212> TYPE: PRT
<213> ORGANISM: Yellow Croaker

<400> SEQUENCE: 435

Pro Gly Pro Ala
1

<210> SEQ ID NO 436
<211> LENGTH: 4
<212> TYPE: PRT
<213> ORGANISM: Yellow Croaker

<400> SEQUENCE: 436

Pro Gly Pro Ala
1

<210> SEQ ID NO 437
<211> LENGTH: 3
<212> TYPE: PRT
<213> ORGANISM: Yellow Croaker

<400> SEQUENCE: 437
```

Met Asp Ala
1

<210> SEQ ID NO 438
<211> LENGTH: 3
<212> TYPE: PRT
<213> ORGANISM: Yellow Croaker

<400> SEQUENCE: 438

Gly Arg Val
1

<210> SEQ ID NO 439
<211> LENGTH: 3
<212> TYPE: PRT
<213> ORGANISM: Yellow Croaker

<400> SEQUENCE: 439

Thr Gly Phe
1

<210> SEQ ID NO 440
<211> LENGTH: 4
<212> TYPE: PRT
<213> ORGANISM: Yellow Croaker

<400> SEQUENCE: 440

Ser Gly Ser Ala
1

<210> SEQ ID NO 441
<211> LENGTH: 3
<212> TYPE: PRT
<213> ORGANISM: Yellow Croaker

<400> SEQUENCE: 441

Pro Gly Phe
1

<210> SEQ ID NO 442
<211> LENGTH: 3
<212> TYPE: PRT
<213> ORGANISM: Yellow Croaker

<400> SEQUENCE: 442

Asp Asp Ala
1

<210> SEQ ID NO 443
<211> LENGTH: 3
<212> TYPE: PRT
<213> ORGANISM: Yellow Croaker

<400> SEQUENCE: 443

Gln Gly Leu
1

<210> SEQ ID NO 444
<211> LENGTH: 2
<212> TYPE: PRT
<213> ORGANISM: Yellow Croaker

<400> SEQUENCE: 444

Glu Tyr
1

```
<210> SEQ ID NO 445
<211> LENGTH: 3
<212> TYPE: PRT
<213> ORGANISM: Yellow Croaker

<400> SEQUENCE: 445

Arg Gly Ala
1

<210> SEQ ID NO 446
<211> LENGTH: 3
<212> TYPE: PRT
<213> ORGANISM: Yellow Croaker

<400> SEQUENCE: 446

Gly Asn Leu
1

<210> SEQ ID NO 447
<211> LENGTH: 2
<212> TYPE: PRT
<213> ORGANISM: Yellow Croaker

<400> SEQUENCE: 447

Met Phe
1

<210> SEQ ID NO 448
<211> LENGTH: 2
<212> TYPE: PRT
<213> ORGANISM: Yellow Croaker

<400> SEQUENCE: 448

Asp Tyr
1

<210> SEQ ID NO 449
<211> LENGTH: 2
<212> TYPE: PRT
<213> ORGANISM: Yellow Croaker

<400> SEQUENCE: 449

Gln Phe
1

<210> SEQ ID NO 450
<211> LENGTH: 2
<212> TYPE: PRT
<213> ORGANISM: Yellow Croaker

<400> SEQUENCE: 450

Arg Leu
1

<210> SEQ ID NO 451
<211> LENGTH: 3
<212> TYPE: PRT
<213> ORGANISM: Yellow Croaker

<400> SEQUENCE: 451

Pro Gly Ile
1
```

```
<210> SEQ ID NO 452
<211> LENGTH: 3
<212> TYPE: PRT
<213> ORGANISM: Yellow Croaker

<400> SEQUENCE: 452

Pro Gly Leu
1

<210> SEQ ID NO 453
<211> LENGTH: 2
<212> TYPE: PRT
<213> ORGANISM: Yellow Croaker

<400> SEQUENCE: 453

Thr Tyr
1

<210> SEQ ID NO 454
<211> LENGTH: 3
<212> TYPE: PRT
<213> ORGANISM: Yellow Croaker

<400> SEQUENCE: 454

Ser Gly Leu
1

<210> SEQ ID NO 455
<211> LENGTH: 3
<212> TYPE: PRT
<213> ORGANISM: Yellow Croaker

<400> SEQUENCE: 455

Glu Gly Ala
1

<210> SEQ ID NO 456
<211> LENGTH: 3
<212> TYPE: PRT
<213> ORGANISM: Yellow Croaker

<400> SEQUENCE: 456

Gly Glu Ala
1

<210> SEQ ID NO 457
<211> LENGTH: 3
<212> TYPE: PRT
<213> ORGANISM: Yellow Croaker

<400> SEQUENCE: 457

Lys Gly Ala
1

<210> SEQ ID NO 458
<211> LENGTH: 3
<212> TYPE: PRT
<213> ORGANISM: Yellow Croaker

<400> SEQUENCE: 458

Gln Gly Ala
1

<210> SEQ ID NO 459
<211> LENGTH: 3
```

```
<212> TYPE: PRT
<213> ORGANISM: Yellow Croaker

<400> SEQUENCE: 459

Pro Gly Val
1

<210> SEQ ID NO 460
<211> LENGTH: 3
<212> TYPE: PRT
<213> ORGANISM: Yellow Croaker

<400> SEQUENCE: 460

Gly Pro Val
1

<210> SEQ ID NO 461
<211> LENGTH: 2
<212> TYPE: PRT
<213> ORGANISM: Yellow Croaker

<400> SEQUENCE: 461

Cys Phe
1

<210> SEQ ID NO 462
<211> LENGTH: 2
<212> TYPE: PRT
<213> ORGANISM: Yellow Croaker

<400> SEQUENCE: 462

Thr Phe
1

<210> SEQ ID NO 463
<211> LENGTH: 3
<212> TYPE: PRT
<213> ORGANISM: Yellow Croaker

<400> SEQUENCE: 463

Asp Gly Ala
1

<210> SEQ ID NO 464
<211> LENGTH: 2
<212> TYPE: PRT
<213> ORGANISM: Yellow Croaker

<400> SEQUENCE: 464

Glu Ile
1

<210> SEQ ID NO 465
<211> LENGTH: 2
<212> TYPE: PRT
<213> ORGANISM: Yellow Croaker

<400> SEQUENCE: 465

Gln Leu
1

<210> SEQ ID NO 466
<211> LENGTH: 2
<212> TYPE: PRT
<213> ORGANISM: Yellow Croaker
```

```
<400> SEQUENCE: 466

Ser Phe
1

<210> SEQ ID NO 467
<211> LENGTH: 3
<212> TYPE: PRT
<213> ORGANISM: Yellow Croaker

<400> SEQUENCE: 467

Thr Gly Ala
1

<210> SEQ ID NO 468
<211> LENGTH: 2
<212> TYPE: PRT
<213> ORGANISM: Yellow Croaker

<400> SEQUENCE: 468

Asp Leu
1

<210> SEQ ID NO 469
<211> LENGTH: 2
<212> TYPE: PRT
<213> ORGANISM: Yellow Croaker

<400> SEQUENCE: 469

Glu Val
1

<210> SEQ ID NO 470
<211> LENGTH: 2
<212> TYPE: PRT
<213> ORGANISM: Yellow Croaker

<400> SEQUENCE: 470

Asp Ile
1

<210> SEQ ID NO 471
<211> LENGTH: 2
<212> TYPE: PRT
<213> ORGANISM: Yellow Croaker

<400> SEQUENCE: 471

Glu Val
1

<210> SEQ ID NO 472
<211> LENGTH: 2
<212> TYPE: PRT
<213> ORGANISM: Yellow Croaker

<400> SEQUENCE: 472

Lys Val
1

<210> SEQ ID NO 473
<211> LENGTH: 2
<212> TYPE: PRT
<213> ORGANISM: Yellow Croaker

<400> SEQUENCE: 473
```

<210> SEQ ID NO 474
<211> LENGTH: 2
<212> TYPE: PRT
<213> ORGANISM: Yellow Croaker

<400> SEQUENCE: 474

Asn Ile
1

<210> SEQ ID NO 475
<211> LENGTH: 3
<212> TYPE: PRT
<213> ORGANISM: Yellow Croaker

<400> SEQUENCE: 475

Pro Gly Ala
1

<210> SEQ ID NO 476
<211> LENGTH: 3
<212> TYPE: PRT
<213> ORGANISM: Yellow Croaker

<400> SEQUENCE: 476

Gly Pro Ala
1

<210> SEQ ID NO 477
<211> LENGTH: 3
<212> TYPE: PRT
<213> ORGANISM: Yellow Croaker

<400> SEQUENCE: 477

Ser Gly Ala
1

<210> SEQ ID NO 478
<211> LENGTH: 3
<212> TYPE: PRT
<213> ORGANISM: Yellow Croaker

<400> SEQUENCE: 478

Gly Ser Ala
1

<210> SEQ ID NO 479
<211> LENGTH: 2
<212> TYPE: PRT
<213> ORGANISM: Yellow Croaker

<400> SEQUENCE: 479

Asn Val
1

<210> SEQ ID NO 480
<211> LENGTH: 2
<212> TYPE: PRT
<213> ORGANISM: Yellow Croaker

<400> SEQUENCE: 480

Pro Ile

Arg Ala
1

```
<210> SEQ ID NO 481
<211> LENGTH: 2
<212> TYPE: PRT
<213> ORGANISM: Yellow Croaker

<400> SEQUENCE: 481

Gly Phe
1

<210> SEQ ID NO 482
<211> LENGTH: 2
<212> TYPE: PRT
<213> ORGANISM: Yellow Croaker

<400> SEQUENCE: 482

Cys Val
1

<210> SEQ ID NO 483
<211> LENGTH: 2
<212> TYPE: PRT
<213> ORGANISM: Yellow Croaker

<400> SEQUENCE: 483

Ser Val
1

<210> SEQ ID NO 484
<211> LENGTH: 2
<212> TYPE: PRT
<213> ORGANISM: Yellow Croaker

<400> SEQUENCE: 484

Gly Ile
1

<210> SEQ ID NO 485
<211> LENGTH: 2
<212> TYPE: PRT
<213> ORGANISM: Yellow Croaker

<400> SEQUENCE: 485

Gly Leu
1

<210> SEQ ID NO 486
<211> LENGTH: 2
<212> TYPE: PRT
<213> ORGANISM: Yellow Croaker

<400> SEQUENCE: 486

Ser Ala
1

<210> SEQ ID NO 487
<211> LENGTH: 2
<212> TYPE: PRT
<213> ORGANISM: Yellow Croaker

<400> SEQUENCE: 487

Gly Val
1
```

```
<210> SEQ ID NO 488
<211> LENGTH: 2
<212> TYPE: PRT
<213> ORGANISM: Yellow Croaker

<400> SEQUENCE: 488

Gly Ala
1

<210> SEQ ID NO 489
<211> LENGTH: 31
<212> TYPE: PRT
<213> ORGANISM: Yellow Croaker

<400> SEQUENCE: 489

Arg Gly Pro Pro Gly Pro Pro Gly Pro Pro Gly Ser Gln Gly His Thr
1               5                   10                  15

Gly His Pro Gly Glu Pro Gly Glu Pro Gly Gln Pro Gly Pro Val
            20                  25                  30

<210> SEQ ID NO 490
<211> LENGTH: 26
<212> TYPE: PRT
<213> ORGANISM: Yellow Croaker

<400> SEQUENCE: 490

Gly Pro Arg Gly Asp Lys Gly Pro Arg Gly Asp Arg Gly Pro Gln Gly
1               5                   10                  15

Pro Asn Gly Lys Asp Gly Lys Pro Gly Leu
            20                  25

<210> SEQ ID NO 491
<211> LENGTH: 26
<212> TYPE: PRT
<213> ORGANISM: Yellow Croaker

<400> SEQUENCE: 491

Gly Pro Pro Gly Gly Lys Gly Glu Lys Gly Glu Pro Gly His Arg Gly
1               5                   10                  15

Pro Asp Gly Asn Ser Gly Arg Asp Gly Ala
            20                  25

<210> SEQ ID NO 492
<211> LENGTH: 21
<212> TYPE: PRT
<213> ORGANISM: Yellow Croaker

<400> SEQUENCE: 492

Gly Gln Asp Gly Arg Thr Gly Pro Pro Gly Pro Thr Gly Pro Arg Gly
1               5                   10                  15

Gln Pro Gly Asn Ile
            20

<210> SEQ ID NO 493
<211> LENGTH: 19
<212> TYPE: PRT
<213> ORGANISM: Yellow Croaker

<400> SEQUENCE: 493

Gln Gly Pro Pro Gly Pro Gln Gly Glu Glu Gly Lys Arg Gly Pro Thr
1               5                   10                  15

Gly Glu Leu
```

<210> SEQ ID NO 494
<211> LENGTH: 17
<212> TYPE: PRT
<213> ORGANISM: Yellow Croaker

<400> SEQUENCE: 494

Gly Glu Asp Gly Asn Asn Gly Arg Pro Gly Lys Pro Gly Asp Arg Gly
1               5                   10                  15

Ala

<210> SEQ ID NO 495
<211> LENGTH: 18
<212> TYPE: PRT
<213> ORGANISM: Yellow Croaker

<400> SEQUENCE: 495

Pro Gly Pro Lys Gly Pro Ser Gly Glu Pro Gly Lys Pro Gly Glu Lys
1               5                   10                  15

Gly Ala

<210> SEQ ID NO 496
<211> LENGTH: 17
<212> TYPE: PRT
<213> ORGANISM: Yellow Croaker

<400> SEQUENCE: 496

Gly Arg Glu Gly Asn Pro Gly Asn Asp Gly Pro Pro Gly Arg Pro Gly
1               5                   10                  15

Ile

<210> SEQ ID NO 497
<211> LENGTH: 16
<212> TYPE: PRT
<213> ORGANISM: Yellow Croaker

<400> SEQUENCE: 497

Pro Gly Ser Pro Gly Ser Ser Gly Pro Thr Gly Lys Glu Gly Pro Ala
1               5                   10                  15

<210> SEQ ID NO 498
<211> LENGTH: 15
<212> TYPE: PRT
<213> ORGANISM: Yellow Croaker

<400> SEQUENCE: 498

Gln Gly Met Pro Gly Pro Ser Gly Pro Ser Gly Asp Thr Gly Val
1               5                   10                  15

<210> SEQ ID NO 499
<211> LENGTH: 15
<212> TYPE: PRT
<213> ORGANISM: Yellow Croaker

<400> SEQUENCE: 499

Pro Gly Pro Arg Gly Gly Pro Gly Pro Gln Gly Pro Gln Gly Ala
1               5                   10                  15

<210> SEQ ID NO 500
<211> LENGTH: 14
<212> TYPE: PRT
<213> ORGANISM: Yellow Croaker

```
<400> SEQUENCE: 500

Gly His Gln Gly Pro Gly Met Pro Gly Glu Arg Gly Ala
1               5                   10

<210> SEQ ID NO 501
<211> LENGTH: 11
<212> TYPE: PRT
<213> ORGANISM: Yellow Croaker

<400> SEQUENCE: 501

Glu Asp Gly Cys Thr Arg His Thr Gly Glu Trp
1               5                   10

<210> SEQ ID NO 502
<211> LENGTH: 13
<212> TYPE: PRT
<213> ORGANISM: Yellow Croaker

<400> SEQUENCE: 502

Arg Gly Glu Arg Gly Pro Ser Gly Gly Lys Gly Glu Val
1               5                   10

<210> SEQ ID NO 503
<211> LENGTH: 14
<212> TYPE: PRT
<213> ORGANISM: Yellow Croaker

<400> SEQUENCE: 503

Gly Glu Lys Gly Pro Ser Gly Glu Ser Gly Pro Pro Gly Ala
1               5                   10

<210> SEQ ID NO 504
<211> LENGTH: 13
<212> TYPE: PRT
<213> ORGANISM: Yellow Croaker

<400> SEQUENCE: 504

Pro Asp Pro Gly Pro Gly Pro Met Gly Met Met Gly Ala
1               5                   10

<210> SEQ ID NO 505
<211> LENGTH: 13
<212> TYPE: PRT
<213> ORGANISM: Yellow Croaker

<400> SEQUENCE: 505

Ser Gly Pro Gln Gly Pro Met Gly Ser Arg Gly Pro Ala
1               5                   10

<210> SEQ ID NO 506
<211> LENGTH: 11
<212> TYPE: PRT
<213> ORGANISM: Yellow Croaker

<400> SEQUENCE: 506

Gly Glu Arg Gly Glu Arg Gly Met Lys Gly Leu
1               5                   10

<210> SEQ ID NO 507
<211> LENGTH: 12
<212> TYPE: PRT
<213> ORGANISM: Yellow Croaker

<400> SEQUENCE: 507
```

Lys Gly Asp Arg Gly Glu Pro Gly Ser Pro Gly Ala
1               5                   10

<210> SEQ ID NO 508
<211> LENGTH: 13
<212> TYPE: PRT
<213> ORGANISM: Yellow Croaker

<400> SEQUENCE: 508

Pro Gly Ser Asp Gly Gly Lys Gly Glu Pro Gly Ser Ala
1               5                   10

<210> SEQ ID NO 509
<211> LENGTH: 10
<212> TYPE: PRT
<213> ORGANISM: Yellow Croaker

<400> SEQUENCE: 509

Thr Pro Glu Gly Ser Arg Lys Asn Pro Ala
1               5                   10

<210> SEQ ID NO 510
<211> LENGTH: 12
<212> TYPE: PRT
<213> ORGANISM: Yellow Croaker

<400> SEQUENCE: 510

Pro Gly Pro Pro Gly Pro Pro Gly Pro Pro Gly Leu
1               5                   10

<210> SEQ ID NO 511
<211> LENGTH: 10
<212> TYPE: PRT
<213> ORGANISM: Yellow Croaker

<400> SEQUENCE: 511

Asp Pro Asn Gln Gly Cys Thr Asn Asp Ala
1               5                   10

<210> SEQ ID NO 512
<211> LENGTH: 9
<212> TYPE: PRT
<213> ORGANISM: Yellow Croaker

<400> SEQUENCE: 512

Pro Gly Met Lys Gly His Arg Gly Tyr
1               5

<210> SEQ ID NO 513
<211> LENGTH: 11
<212> TYPE: PRT
<213> ORGANISM: Yellow Croaker

<400> SEQUENCE: 513

Gly Gly Lys Gly Glu Arg Gly Asn Pro Gly Ala
1               5                   10

<210> SEQ ID NO 514
<211> LENGTH: 11
<212> TYPE: PRT
<213> ORGANISM: Yellow Croaker

<400> SEQUENCE: 514

Gly Pro Pro Gly Asn Pro Gly Asn Asn Gly Leu
1               5                   10

<210> SEQ ID NO 515
<211> LENGTH: 8
<212> TYPE: PRT
<213> ORGANISM: Yellow Croaker

<400> SEQUENCE: 515

Arg Thr Asn Lys Pro Ser Arg Leu
1               5

<210> SEQ ID NO 516
<211> LENGTH: 11
<212> TYPE: PRT
<213> ORGANISM: Yellow Croaker

<400> SEQUENCE: 516

Gly Pro Lys Gly Glu Pro Gly Asn Ser Gly Ala
1               5                   10

<210> SEQ ID NO 517
<211> LENGTH: 10
<212> TYPE: PRT
<213> ORGANISM: Yellow Croaker

<400> SEQUENCE: 517

Pro Gly Met Thr Gly Pro Gln Gly Glu Ala
1               5                   10

<210> SEQ ID NO 518
<211> LENGTH: 10
<212> TYPE: PRT
<213> ORGANISM: Yellow Croaker

<400> SEQUENCE: 518

Arg Gly Asp Arg Gly Ser Pro Gly Gly Ala
1               5                   10

<210> SEQ ID NO 519
<211> LENGTH: 11
<212> TYPE: PRT
<213> ORGANISM: Yellow Croaker

<400> SEQUENCE: 519

Gly Pro Ser Gly Pro Pro Gly Ser Pro Gly Leu
1               5                   10

<210> SEQ ID NO 520
<211> LENGTH: 10
<212> TYPE: PRT
<213> ORGANISM: Yellow Croaker

<400> SEQUENCE: 520

Pro Gly Gly Pro Gly Pro Lys Gly Glu Leu
1               5                   10

<210> SEQ ID NO 521
<211> LENGTH: 9
<212> TYPE: PRT
<213> ORGANISM: Yellow Croaker

<400> SEQUENCE: 521

Asp Gly Arg Lys Gly Glu Pro Gly Ala
1               5

```
<210> SEQ ID NO 522
<211> LENGTH: 9
<212> TYPE: PRT
<213> ORGANISM: Yellow Croaker

<400> SEQUENCE: 522

Gly Glu Lys Gly Glu Gln Gly Pro Ala
1               5

<210> SEQ ID NO 523
<211> LENGTH: 9
<212> TYPE: PRT
<213> ORGANISM: Yellow Croaker

<400> SEQUENCE: 523

Gly Pro Ser Gly Glu Gln Gly Met Val
1               5

<210> SEQ ID NO 524
<211> LENGTH: 9
<212> TYPE: PRT
<213> ORGANISM: Yellow Croaker

<400> SEQUENCE: 524

Arg Gly Glu Pro Gly Pro Asn Gly Ala
1               5

<210> SEQ ID NO 525
<211> LENGTH: 9
<212> TYPE: PRT
<213> ORGANISM: Yellow Croaker

<400> SEQUENCE: 525

Asn Gly Asp Lys Gly Glu Ser Gly Ala
1               5

<210> SEQ ID NO 526
<211> LENGTH: 9
<212> TYPE: PRT
<213> ORGANISM: Yellow Croaker

<400> SEQUENCE: 526

Gly Pro Arg Gly Pro Pro Gly Asp Ala
1               5

<210> SEQ ID NO 527
<211> LENGTH: 7
<212> TYPE: PRT
<213> ORGANISM: Yellow Croaker

<400> SEQUENCE: 527

Thr Thr Arg Glu Thr Cys Ile
1               5

<210> SEQ ID NO 528
<211> LENGTH: 8
<212> TYPE: PRT
<213> ORGANISM: Yellow Croaker

<400> SEQUENCE: 528

Gly Lys Pro Gly Asp Arg Gly Ile
1               5

<210> SEQ ID NO 529
<211> LENGTH: 8
```

```
<212> TYPE: PRT
<213> ORGANISM: Yellow Croaker

<400> SEQUENCE: 529

Gly Lys Asp Gly Pro Arg Gly Leu
1               5

<210> SEQ ID NO 530
<211> LENGTH: 8
<212> TYPE: PRT
<213> ORGANISM: Yellow Croaker

<400> SEQUENCE: 530

Gly Pro Arg Gly Glu Lys Gly Val
1               5

<210> SEQ ID NO 531
<211> LENGTH: 9
<212> TYPE: PRT
<213> ORGANISM: Yellow Croaker

<400> SEQUENCE: 531

Pro Gly Pro Asp Gly Asn Asn Gly Ala
1               5

<210> SEQ ID NO 532
<211> LENGTH: 8
<212> TYPE: PRT
<213> ORGANISM: Yellow Croaker

<400> SEQUENCE: 532

Met Asp Gly Glu Ser Gly Ser Leu
1               5

<210> SEQ ID NO 533
<211> LENGTH: 6
<212> TYPE: PRT
<213> ORGANISM: Yellow Croaker

<400> SEQUENCE: 533

Arg Thr Cys Arg Asp Ile
1               5

<210> SEQ ID NO 534
<211> LENGTH: 7
<212> TYPE: PRT
<213> ORGANISM: Yellow Croaker

<400> SEQUENCE: 534

Pro Gly Glu Arg Gly Glu Val
1               5

<210> SEQ ID NO 535
<211> LENGTH: 7
<212> TYPE: PRT
<213> ORGANISM: Yellow Croaker

<400> SEQUENCE: 535

Glu Gly Arg Thr Gly Pro Val
1               5

<210> SEQ ID NO 536
<211> LENGTH: 8
<212> TYPE: PRT
<213> ORGANISM: Yellow Croaker
```

<400> SEQUENCE: 536

Gly Pro Lys Gly Glu Pro Gly Ala
1               5

<210> SEQ ID NO 537
<211> LENGTH: 7
<212> TYPE: PRT
<213> ORGANISM: Yellow Croaker

<400> SEQUENCE: 537

Arg Gly Pro Pro Gly Asn Ile
1               5

<210> SEQ ID NO 538
<211> LENGTH: 6
<212> TYPE: PRT
<213> ORGANISM: Yellow Croaker

<400> SEQUENCE: 538

Glu Gly Asn Ser Arg Phe
1               5

<210> SEQ ID NO 539
<211> LENGTH: 8
<212> TYPE: PRT
<213> ORGANISM: Yellow Croaker

<400> SEQUENCE: 539

Gly Pro Ser Gly Pro Arg Gly Ala
1               5

<210> SEQ ID NO 540
<211> LENGTH: 7
<212> TYPE: PRT
<213> ORGANISM: Yellow Croaker

<400> SEQUENCE: 540

Arg Gly Glu Thr Gly Pro Ala
1               5

<210> SEQ ID NO 541
<211> LENGTH: 6
<212> TYPE: PRT
<213> ORGANISM: Yellow Croaker

<400> SEQUENCE: 541

His Cys Lys Asn Ser Val
1               5

<210> SEQ ID NO 542
<211> LENGTH: 7
<212> TYPE: PRT
<213> ORGANISM: Yellow Croaker

<400> SEQUENCE: 542

Arg Gly Met Pro Gly Pro Ala
1               5

<210> SEQ ID NO 543
<211> LENGTH: 8
<212> TYPE: PRT
<213> ORGANISM: Yellow Croaker

<400> SEQUENCE: 543

Gly Pro Ser Gly Pro Gln Gly Ala
1               5

<210> SEQ ID NO 544
<211> LENGTH: 7
<212> TYPE: PRT
<213> ORGANISM: Yellow Croaker

<400> SEQUENCE: 544

Arg Gly Asp Ser Gly Pro Ala
1               5

<210> SEQ ID NO 545
<211> LENGTH: 5
<212> TYPE: PRT
<213> ORGANISM: Yellow Croaker

<400> SEQUENCE: 545

Ser His Pro Glu Trp
1               5

<210> SEQ ID NO 546
<211> LENGTH: 8
<212> TYPE: PRT
<213> ORGANISM: Yellow Croaker

<400> SEQUENCE: 546

Gly Pro Pro Gly Pro Thr Gly Ala
1               5

<210> SEQ ID NO 547
<211> LENGTH: 7
<212> TYPE: PRT
<213> ORGANISM: Yellow Croaker

<400> SEQUENCE: 547

Arg Gly Pro Pro Gly Pro Ala
1               5

<210> SEQ ID NO 548
<211> LENGTH: 6
<212> TYPE: PRT
<213> ORGANISM: Yellow Croaker

<400> SEQUENCE: 548

Arg Gly Pro Pro Gly Tyr
1               5

<210> SEQ ID NO 549
<211> LENGTH: 6
<212> TYPE: PRT
<213> ORGANISM: Yellow Croaker

<400> SEQUENCE: 549

Gly Glu Arg Gly Arg Ala
1               5

<210> SEQ ID NO 550
<211> LENGTH: 8
<212> TYPE: PRT
<213> ORGANISM: Yellow Croaker

<400> SEQUENCE: 550

Gly Gly His Gly Gly Met Gly Ala

```
1               5

<210> SEQ ID NO 551
<211> LENGTH: 6
<212> TYPE: PRT
<213> ORGANISM: Yellow Croaker

<400> SEQUENCE: 551

Asn Gly Gly Thr Glu Phe
1               5

<210> SEQ ID NO 552
<211> LENGTH: 6
<212> TYPE: PRT
<213> ORGANISM: Yellow Croaker

<400> SEQUENCE: 552

Ser Pro Gln Ser Met Ala
1               5

<210> SEQ ID NO 553
<211> LENGTH: 6
<212> TYPE: PRT
<213> ORGANISM: Yellow Croaker

<400> SEQUENCE: 553

Gln Gly Ser Asn Asp Val
1               5

<210> SEQ ID NO 554
<211> LENGTH: 6
<212> TYPE: PRT
<213> ORGANISM: Yellow Croaker

<400> SEQUENCE: 554

Gly Lys Asp Gly Arg Ala
1               5

<210> SEQ ID NO 555
<211> LENGTH: 7
<212> TYPE: PRT
<213> ORGANISM: Yellow Croaker

<400> SEQUENCE: 555

Pro Gly Pro Pro Gly Pro Ala
1               5

<210> SEQ ID NO 556
<211> LENGTH: 5
<212> TYPE: PRT
<213> ORGANISM: Yellow Croaker

<400> SEQUENCE: 556

Asn Asp Glu Thr Ile
1               5

<210> SEQ ID NO 557
<211> LENGTH: 6
<212> TYPE: PRT
<213> ORGANISM: Yellow Croaker

<400> SEQUENCE: 557

Pro Gly Asp Gln Gly Leu
1               5
```

<210> SEQ ID NO 558
<211> LENGTH: 7
<212> TYPE: PRT
<213> ORGANISM: Yellow Croaker

<400> SEQUENCE: 558

Pro Gly Ser Gly Gly Pro Leu
1               5

<210> SEQ ID NO 559
<211> LENGTH: 5
<212> TYPE: PRT
<213> ORGANISM: Yellow Croaker

<400> SEQUENCE: 559

His Pro Glu Ser Ile
1               5

<210> SEQ ID NO 560
<211> LENGTH: 4
<212> TYPE: PRT
<213> ORGANISM: Yellow Croaker

<400> SEQUENCE: 560

Gln Lys Asn Trp
1

<210> SEQ ID NO 561
<211> LENGTH: 5
<212> TYPE: PRT
<213> ORGANISM: Yellow Croaker

<400> SEQUENCE: 561

Arg Ser Thr Glu Ala
1               5

<210> SEQ ID NO 562
<211> LENGTH: 6
<212> TYPE: PRT
<213> ORGANISM: Yellow Croaker

<400> SEQUENCE: 562

Pro Gly Gly Arg Gly Leu
1               5

<210> SEQ ID NO 563
<211> LENGTH: 6
<212> TYPE: PRT
<213> ORGANISM: Yellow Croaker

<400> SEQUENCE: 563

Gly Pro Arg Gly Pro Ala
1               5

<210> SEQ ID NO 564
<211> LENGTH: 4
<212> TYPE: PRT
<213> ORGANISM: Yellow Croaker

<400> SEQUENCE: 564

Glu Gln Glu Phe
1

<210> SEQ ID NO 565

```
<211> LENGTH: 6
<212> TYPE: PRT
<213> ORGANISM: Yellow Croaker

<400> SEQUENCE: 565

Arg Gly Ser Thr Gly Ala
1               5

<210> SEQ ID NO 566
<211> LENGTH: 6
<212> TYPE: PRT
<213> ORGANISM: Yellow Croaker

<400> SEQUENCE: 566

Asp Gly Gln Thr Gly Ala
1               5

<210> SEQ ID NO 567
<211> LENGTH: 6
<212> TYPE: PRT
<213> ORGANISM: Yellow Croaker

<400> SEQUENCE: 567

Gly Gly Arg Gly Glu Ala
1               5

<210> SEQ ID NO 568
<211> LENGTH: 6
<212> TYPE: PRT
<213> ORGANISM: Yellow Croaker

<400> SEQUENCE: 568

Pro Gly Thr Pro Gly Leu
1               5

<210> SEQ ID NO 569
<211> LENGTH: 6
<212> TYPE: PRT
<213> ORGANISM: Yellow Croaker

<400> SEQUENCE: 569

Gly Pro His Gly Pro Ala
1               5

<210> SEQ ID NO 570
<211> LENGTH: 5
<212> TYPE: PRT
<213> ORGANISM: Yellow Croaker

<400> SEQUENCE: 570

Gly Gln Arg Gly Leu
1               5

<210> SEQ ID NO 571
<211> LENGTH: 6
<212> TYPE: PRT
<213> ORGANISM: Yellow Croaker

<400> SEQUENCE: 571

Pro Gly Pro Gln Gly Ala
1               5

<210> SEQ ID NO 572
<211> LENGTH: 6
<212> TYPE: PRT
```

```
<213> ORGANISM: Yellow Croaker

<400> SEQUENCE: 572

Ser Gly Thr Pro Gly Val
1               5

<210> SEQ ID NO 573
<211> LENGTH: 6
<212> TYPE: PRT
<213> ORGANISM: Yellow Croaker

<400> SEQUENCE: 573

Gly Gln Ser Gly Pro Ala
1               5

<210> SEQ ID NO 574
<211> LENGTH: 4
<212> TYPE: PRT
<213> ORGANISM: Yellow Croaker

<400> SEQUENCE: 574

Lys Lys His Val
1

<210> SEQ ID NO 575
<211> LENGTH: 6
<212> TYPE: PRT
<213> ORGANISM: Yellow Croaker

<400> SEQUENCE: 575

Gly Pro Pro Gly Pro Ala
1               5

<210> SEQ ID NO 576
<211> LENGTH: 4
<212> TYPE: PRT
<213> ORGANISM: Yellow Croaker

<400> SEQUENCE: 576

Met His Cys Val
1

<210> SEQ ID NO 577
<211> LENGTH: 6
<212> TYPE: PRT
<213> ORGANISM: Yellow Croaker

<400> SEQUENCE: 577

Thr Gly Pro Gly Gly Val
1               5

<210> SEQ ID NO 578
<211> LENGTH: 5
<212> TYPE: PRT
<213> ORGANISM: Yellow Croaker

<400> SEQUENCE: 578

Asp Gly Ser Lys Ala
1               5

<210> SEQ ID NO 579
<211> LENGTH: 4
<212> TYPE: PRT
<213> ORGANISM: Yellow Croaker
```

```
<400> SEQUENCE: 579

Asn Thr Gln Ile
1

<210> SEQ ID NO 580
<211> LENGTH: 5
<212> TYPE: PRT
<213> ORGANISM: Yellow Croaker

<400> SEQUENCE: 580

Gly Asn Arg Gly Ala
1               5

<210> SEQ ID NO 581
<211> LENGTH: 5
<212> TYPE: PRT
<213> ORGANISM: Yellow Croaker

<400> SEQUENCE: 581

Gly Pro Pro Gly Phe
1               5

<210> SEQ ID NO 582
<211> LENGTH: 4
<212> TYPE: PRT
<213> ORGANISM: Yellow Croaker

<400> SEQUENCE: 582

Ser Gln Asn Ile
1

<210> SEQ ID NO 583
<211> LENGTH: 6
<212> TYPE: PRT
<213> ORGANISM: Yellow Croaker

<400> SEQUENCE: 583

Gly Pro Gly Gly Pro Ala
1               5

<210> SEQ ID NO 584
<211> LENGTH: 5
<212> TYPE: PRT
<213> ORGANISM: Yellow Croaker

<400> SEQUENCE: 584

Gly Thr Pro Gly Leu
1               5

<210> SEQ ID NO 585
<211> LENGTH: 5
<212> TYPE: PRT
<213> ORGANISM: Yellow Croaker

<400> SEQUENCE: 585

Gly Asp Pro Gly Val
1               5

<210> SEQ ID NO 586
<211> LENGTH: 4
<212> TYPE: PRT
<213> ORGANISM: Yellow Croaker

<400> SEQUENCE: 586
```

Arg Gly His Ala
1

<210> SEQ ID NO 587
<211> LENGTH: 4
<212> TYPE: PRT
<213> ORGANISM: Yellow Croaker

<400> SEQUENCE: 587

Ser Lys Thr Val
1

<210> SEQ ID NO 588
<211> LENGTH: 5
<212> TYPE: PRT
<213> ORGANISM: Yellow Croaker

<400> SEQUENCE: 588

Gly Met Pro Gly Ala
1               5

<210> SEQ ID NO 589
<211> LENGTH: 4
<212> TYPE: PRT
<213> ORGANISM: Yellow Croaker

<400> SEQUENCE: 589

Asp Gln Pro Ala
1

<210> SEQ ID NO 590
<211> LENGTH: 5
<212> TYPE: PRT
<213> ORGANISM: Yellow Croaker

<400> SEQUENCE: 590

Gly Glu Pro Gly Ala
1               5

<210> SEQ ID NO 591
<211> LENGTH: 3
<212> TYPE: PRT
<213> ORGANISM: Yellow Croaker

<400> SEQUENCE: 591

Asp Glu Tyr
1

<210> SEQ ID NO 592
<211> LENGTH: 3
<212> TYPE: PRT
<213> ORGANISM: Yellow Croaker

<400> SEQUENCE: 592

Lys Asp Tyr
1

<210> SEQ ID NO 593
<211> LENGTH: 3
<212> TYPE: PRT
<213> ORGANISM: Yellow Croaker

<400> SEQUENCE: 593

Met Arg Leu
1

<210> SEQ ID NO 594
<211> LENGTH: 4
<212> TYPE: PRT
<213> ORGANISM: Yellow Croaker

<400> SEQUENCE: 594

Gly Glu Thr Ile
1

<210> SEQ ID NO 595
<211> LENGTH: 4
<212> TYPE: PRT
<213> ORGANISM: Yellow Croaker

<400> SEQUENCE: 595

Ser Asn Gln Ala
1

<210> SEQ ID NO 596
<211> LENGTH: 4
<212> TYPE: PRT
<213> ORGANISM: Yellow Croaker

<400> SEQUENCE: 596

Thr Ser Gly Phe
1

<210> SEQ ID NO 597
<211> LENGTH: 4
<212> TYPE: PRT
<213> ORGANISM: Yellow Croaker

<400> SEQUENCE: 597

Asp Gly Asn Val
1

<210> SEQ ID NO 598
<211> LENGTH: 5
<212> TYPE: PRT
<213> ORGANISM: Yellow Croaker

<400> SEQUENCE: 598

Gly Pro Thr Gly Ala
1               5

<210> SEQ ID NO 599
<211> LENGTH: 5
<212> TYPE: PRT
<213> ORGANISM: Yellow Croaker

<400> SEQUENCE: 599

Gly Pro Pro Gly Ala
1               5

<210> SEQ ID NO 600
<211> LENGTH: 4
<212> TYPE: PRT
<213> ORGANISM: Yellow Croaker

<400> SEQUENCE: 600

Gly Gly Asn Phe
1

<210> SEQ ID NO 601
<211> LENGTH: 4
<212> TYPE: PRT
<213> ORGANISM: Yellow Croaker

<400> SEQUENCE: 601

Lys Gly Asp Ala
1

<210> SEQ ID NO 602
<211> LENGTH: 5
<212> TYPE: PRT
<213> ORGANISM: Yellow Croaker

<400> SEQUENCE: 602

Gly Ser Pro Gly Ala
1               5

<210> SEQ ID NO 603
<211> LENGTH: 3
<212> TYPE: PRT
<213> ORGANISM: Yellow Croaker

<400> SEQUENCE: 603

Cys Asp Phe
1

<210> SEQ ID NO 604
<211> LENGTH: 3
<212> TYPE: PRT
<213> ORGANISM: Yellow Croaker

<400> SEQUENCE: 604

Arg Gly Phe
1

<210> SEQ ID NO 605
<211> LENGTH: 3
<212> TYPE: PRT
<213> ORGANISM: Yellow Croaker

<400> SEQUENCE: 605

Glu Asn Leu
1

<210> SEQ ID NO 606
<211> LENGTH: 3
<212> TYPE: PRT
<213> ORGANISM: Yellow Croaker

<400> SEQUENCE: 606

Thr Gln Leu
1

<210> SEQ ID NO 607
<211> LENGTH: 4
<212> TYPE: PRT
<213> ORGANISM: Yellow Croaker

<400> SEQUENCE: 607

Gly Gly Gly Tyr
1

<210> SEQ ID NO 608
<211> LENGTH: 3

```
<212> TYPE: PRT
<213> ORGANISM: Yellow Croaker

<400> SEQUENCE: 608

Gln Gly Phe
1

<210> SEQ ID NO 609
<211> LENGTH: 3
<212> TYPE: PRT
<213> ORGANISM: Yellow Croaker

<400> SEQUENCE: 609

Lys Ser Leu
1

<210> SEQ ID NO 610
<211> LENGTH: 3
<212> TYPE: PRT
<213> ORGANISM: Yellow Croaker

<400> SEQUENCE: 610

Lys Lys Ala
1

<210> SEQ ID NO 611
<211> LENGTH: 3
<212> TYPE: PRT
<213> ORGANISM: Yellow Croaker

<400> SEQUENCE: 611

Arg Gly Leu
1

<210> SEQ ID NO 612
<211> LENGTH: 4
<212> TYPE: PRT
<213> ORGANISM: Yellow Croaker

<400> SEQUENCE: 612

Thr Gly Pro Ala
1

<210> SEQ ID NO 613
<211> LENGTH: 4
<212> TYPE: PRT
<213> ORGANISM: Yellow Croaker

<400> SEQUENCE: 613

Pro Gly Pro Ala
1

<210> SEQ ID NO 614
<211> LENGTH: 3
<212> TYPE: PRT
<213> ORGANISM: Yellow Croaker

<400> SEQUENCE: 614

Gly Arg Val
1

<210> SEQ ID NO 615
<211> LENGTH: 3
<212> TYPE: PRT
<213> ORGANISM: Yellow Croaker
```

<400> SEQUENCE: 615

Ser Gly Tyr
1

<210> SEQ ID NO 616
<211> LENGTH: 3
<212> TYPE: PRT
<213> ORGANISM: Yellow Croaker

<400> SEQUENCE: 616

Thr Gly Phe
1

<210> SEQ ID NO 617
<211> LENGTH: 3
<212> TYPE: PRT
<213> ORGANISM: Yellow Croaker

<400> SEQUENCE: 617

Met Gly Leu
1

<210> SEQ ID NO 618
<211> LENGTH: 3
<212> TYPE: PRT
<213> ORGANISM: Yellow Croaker

<400> SEQUENCE: 618

Pro Gly Phe
1

<210> SEQ ID NO 619
<211> LENGTH: 3
<212> TYPE: PRT
<213> ORGANISM: Yellow Croaker

<400> SEQUENCE: 619

Gln Gly Leu
1

<210> SEQ ID NO 620
<211> LENGTH: 2
<212> TYPE: PRT
<213> ORGANISM: Yellow Croaker

<400> SEQUENCE: 620

Glu Tyr
1

<210> SEQ ID NO 621
<211> LENGTH: 2
<212> TYPE: PRT
<213> ORGANISM: Yellow Croaker

<400> SEQUENCE: 621

Gln Tyr
1

<210> SEQ ID NO 622
<211> LENGTH: 3
<212> TYPE: PRT
<213> ORGANISM: Yellow Croaker

<400> SEQUENCE: 622

Gly Arg Ala
1

<210> SEQ ID NO 623
<211> LENGTH: 3
<212> TYPE: PRT
<213> ORGANISM: Yellow Croaker

<400> SEQUENCE: 623

Arg Gly Ala
1

<210> SEQ ID NO 624
<211> LENGTH: 3
<212> TYPE: PRT
<213> ORGANISM: Yellow Croaker

<400> SEQUENCE: 624

Gln Gly Val
1

<210> SEQ ID NO 625
<211> LENGTH: 3
<212> TYPE: PRT
<213> ORGANISM: Yellow Croaker

<400> SEQUENCE: 625

Thr Gly Leu
1

<210> SEQ ID NO 626
<211> LENGTH: 2
<212> TYPE: PRT
<213> ORGANISM: Yellow Croaker

<400> SEQUENCE: 626

Arg Leu
1

<210> SEQ ID NO 627
<211> LENGTH: 3
<212> TYPE: PRT
<213> ORGANISM: Yellow Croaker

<400> SEQUENCE: 627

Gly Pro Leu
1

<210> SEQ ID NO 628
<211> LENGTH: 3
<212> TYPE: PRT
<213> ORGANISM: Yellow Croaker

<400> SEQUENCE: 628

His Gly Ala
1

<210> SEQ ID NO 629
<211> LENGTH: 2
<212> TYPE: PRT
<213> ORGANISM: Yellow Croaker

<400> SEQUENCE: 629

Thr Tyr

```
<210> SEQ ID NO 630
<211> LENGTH: 3
<212> TYPE: PRT
<213> ORGANISM: Yellow Croaker

<400> SEQUENCE: 630

Thr Gly Val
1

<210> SEQ ID NO 631
<211> LENGTH: 3
<212> TYPE: PRT
<213> ORGANISM: Yellow Croaker

<400> SEQUENCE: 631

Gly Glu Ala
1

<210> SEQ ID NO 632
<211> LENGTH: 3
<212> TYPE: PRT
<213> ORGANISM: Yellow Croaker

<400> SEQUENCE: 632

Gly Lys Ala
1

<210> SEQ ID NO 633
<211> LENGTH: 3
<212> TYPE: PRT
<213> ORGANISM: Yellow Croaker

<400> SEQUENCE: 633

Lys Gly Ala
1

<210> SEQ ID NO 634
<211> LENGTH: 3
<212> TYPE: PRT
<213> ORGANISM: Yellow Croaker

<400> SEQUENCE: 634

Gly Pro Val
1

<210> SEQ ID NO 635
<211> LENGTH: 3
<212> TYPE: PRT
<213> ORGANISM: Yellow Croaker

<400> SEQUENCE: 635

Pro Gly Val
1

<210> SEQ ID NO 636
<211> LENGTH: 2
<212> TYPE: PRT
<213> ORGANISM: Yellow Croaker

<400> SEQUENCE: 636

Cys Phe
1
```

```
<210> SEQ ID NO 637
<211> LENGTH: 2
<212> TYPE: PRT
<213> ORGANISM: Yellow Croaker

<400> SEQUENCE: 637

Thr Phe
1

<210> SEQ ID NO 638
<211> LENGTH: 2
<212> TYPE: PRT
<213> ORGANISM: Yellow Croaker

<400> SEQUENCE: 638

Glu Leu
1

<210> SEQ ID NO 639
<211> LENGTH: 3
<212> TYPE: PRT
<213> ORGANISM: Yellow Croaker

<400> SEQUENCE: 639

Asn Gly Ala
1

<210> SEQ ID NO 640
<211> LENGTH: 3
<212> TYPE: PRT
<213> ORGANISM: Yellow Croaker

<400> SEQUENCE: 640

Gly Asn Ala
1

<210> SEQ ID NO 641
<211> LENGTH: 2
<212> TYPE: PRT
<213> ORGANISM: Yellow Croaker

<400> SEQUENCE: 641

Glu Val
1

<210> SEQ ID NO 642
<211> LENGTH: 2
<212> TYPE: PRT
<213> ORGANISM: Yellow Croaker

<400> SEQUENCE: 642

Asp Ile
1

<210> SEQ ID NO 643
<211> LENGTH: 2
<212> TYPE: PRT
<213> ORGANISM: Yellow Croaker

<400> SEQUENCE: 643

Lys Val
1

<210> SEQ ID NO 644
```

```
<211> LENGTH: 2
<212> TYPE: PRT
<213> ORGANISM: Yellow Croaker

<400> SEQUENCE: 644

Arg Ala
1

<210> SEQ ID NO 645
<211> LENGTH: 3
<212> TYPE: PRT
<213> ORGANISM: Yellow Croaker

<400> SEQUENCE: 645

Gly Pro Ala
1

<210> SEQ ID NO 646
<211> LENGTH: 3
<212> TYPE: PRT
<213> ORGANISM: Yellow Croaker

<400> SEQUENCE: 646

Pro Gly Ala
1

<210> SEQ ID NO 647
<211> LENGTH: 3
<212> TYPE: PRT
<213> ORGANISM: Yellow Croaker

<400> SEQUENCE: 647

Gly Ser Ala
1

<210> SEQ ID NO 648
<211> LENGTH: 2
<212> TYPE: PRT
<213> ORGANISM: Yellow Croaker

<400> SEQUENCE: 648

Thr Ile
1

<210> SEQ ID NO 649
<211> LENGTH: 2
<212> TYPE: PRT
<213> ORGANISM: Yellow Croaker

<400> SEQUENCE: 649

Asp Val
1

<210> SEQ ID NO 650
<211> LENGTH: 2
<212> TYPE: PRT
<213> ORGANISM: Yellow Croaker

<400> SEQUENCE: 650

Pro Ile
1

<210> SEQ ID NO 651
<211> LENGTH: 2
<212> TYPE: PRT
```

```
<213> ORGANISM: Yellow Croaker

<400> SEQUENCE: 651

Pro Leu
1

<210> SEQ ID NO 652
<211> LENGTH: 2
<212> TYPE: PRT
<213> ORGANISM: Yellow Croaker

<400> SEQUENCE: 652

Gly Phe
1

<210> SEQ ID NO 653
<211> LENGTH: 2
<212> TYPE: PRT
<213> ORGANISM: Yellow Croaker

<400> SEQUENCE: 653

Ser Val
1

<210> SEQ ID NO 654
<211> LENGTH: 2
<212> TYPE: PRT
<213> ORGANISM: Yellow Croaker

<400> SEQUENCE: 654

Asp Ala
1

<210> SEQ ID NO 655
<211> LENGTH: 3
<212> TYPE: PRT
<213> ORGANISM: Yellow Croaker

<400> SEQUENCE: 655

Gly Gly Ala
1

<210> SEQ ID NO 656
<211> LENGTH: 2
<212> TYPE: PRT
<213> ORGANISM: Yellow Croaker

<400> SEQUENCE: 656

Gly Leu
1

<210> SEQ ID NO 657
<211> LENGTH: 2
<212> TYPE: PRT
<213> ORGANISM: Yellow Croaker

<400> SEQUENCE: 657

Gly Ala
1

<210> SEQ ID NO 658
<211> LENGTH: 21
<212> TYPE: PRT
<213> ORGANISM: Yellow Croaker
```

```
<400> SEQUENCE: 658

Gly Gln Glu Cys Ser Gly Gln Cys Ser Cys Pro Ser Thr Pro Pro Gln
1               5                   10                  15

Cys Arg Pro Gly Val
            20

<210> SEQ ID NO 659
<211> LENGTH: 13
<212> TYPE: PRT
<213> ORGANISM: Yellow Croaker

<400> SEQUENCE: 659

Asp Gly Arg Cys Cys Thr Pro His Arg Thr Thr Thr Leu
1               5                   10

<210> SEQ ID NO 660
<211> LENGTH: 12
<212> TYPE: PRT
<213> ORGANISM: Yellow Croaker

<400> SEQUENCE: 660

Gly Pro Asp Pro Ser Met Met Arg Glu Asn Cys Leu
1               5                   10

<210> SEQ ID NO 661
<211> LENGTH: 11
<212> TYPE: PRT
<213> ORGANISM: Yellow Croaker

<400> SEQUENCE: 661

Pro Ser Pro Asp Cys Pro Met Pro Arg Arg Val
1               5                   10

<210> SEQ ID NO 662
<211> LENGTH: 11
<212> TYPE: PRT
<213> ORGANISM: Yellow Croaker

<400> SEQUENCE: 662

Cys His His Asn Cys Pro Gly Glu Asn Asp Ile
1               5                   10

<210> SEQ ID NO 663
<211> LENGTH: 9
<212> TYPE: PRT
<213> ORGANISM: Yellow Croaker

<400> SEQUENCE: 663

Thr Asn Asp Asn Arg Asp Cys Arg Leu
1               5

<210> SEQ ID NO 664
<211> LENGTH: 7
<212> TYPE: PRT
<213> ORGANISM: Yellow Croaker

<400> SEQUENCE: 664

Met Lys Lys His Met Met Phe
1               5

<210> SEQ ID NO 665
<211> LENGTH: 8
<212> TYPE: PRT
<213> ORGANISM: Yellow Croaker
```

```
<400> SEQUENCE: 665

Pro Gly Lys Cys Cys Glu Glu Trp
1               5

<210> SEQ ID NO 666
<211> LENGTH: 9
<212> TYPE: PRT
<213> ORGANISM: Yellow Croaker

<400> SEQUENCE: 666

Ser Gly Cys Thr Thr Thr Lys Ser Tyr
1               5

<210> SEQ ID NO 667
<211> LENGTH: 8
<212> TYPE: PRT
<213> ORGANISM: Yellow Croaker

<400> SEQUENCE: 667

Lys Lys Met Met Gly Asp Met Ala
1               5

<210> SEQ ID NO 668
<211> LENGTH: 7
<212> TYPE: PRT
<213> ORGANISM: Yellow Croaker

<400> SEQUENCE: 668

Arg Lys Gly Lys Lys Cys Ile
1               5

<210> SEQ ID NO 669
<211> LENGTH: 7
<212> TYPE: PRT
<213> ORGANISM: Yellow Croaker

<400> SEQUENCE: 669

Arg Pro Cys Glu Ser Gln Leu
1               5

<210> SEQ ID NO 670
<211> LENGTH: 6
<212> TYPE: PRT
<213> ORGANISM: Yellow Croaker

<400> SEQUENCE: 670

Arg Glu Glu Glu Thr Tyr
1               5

<210> SEQ ID NO 671
<211> LENGTH: 8
<212> TYPE: PRT
<213> ORGANISM: Yellow Croaker

<400> SEQUENCE: 671

Asp Gly Cys Gly Cys Cys Arg Val
1               5

<210> SEQ ID NO 672
<211> LENGTH: 6
<212> TYPE: PRT
<213> ORGANISM: Yellow Croaker

<400> SEQUENCE: 672
```

Glu Lys Gln Thr Arg Leu
1               5

<210> SEQ ID NO 673
<211> LENGTH: 7
<212> TYPE: PRT
<213> ORGANISM: Yellow Croaker

<400> SEQUENCE: 673

Cys Asp Pro His Lys Gly Leu
1               5

<210> SEQ ID NO 674
<211> LENGTH: 7
<212> TYPE: PRT
<213> ORGANISM: Yellow Croaker

<400> SEQUENCE: 674

Lys Cys Pro Asp Gly Gln Val
1               5

<210> SEQ ID NO 675
<211> LENGTH: 6
<212> TYPE: PRT
<213> ORGANISM: Yellow Croaker

<400> SEQUENCE: 675

Ser Lys Pro Met Lys Phe
1               5

<210> SEQ ID NO 676
<211> LENGTH: 6
<212> TYPE: PRT
<213> ORGANISM: Yellow Croaker

<400> SEQUENCE: 676

Gln Ser Ser Cys Lys Tyr
1               5

<210> SEQ ID NO 677
<211> LENGTH: 6
<212> TYPE: PRT
<213> ORGANISM: Yellow Croaker

<400> SEQUENCE: 677

Glu Cys Asp Ser Pro Tyr
1               5

<210> SEQ ID NO 678
<211> LENGTH: 7
<212> TYPE: PRT
<213> ORGANISM: Yellow Croaker

<400> SEQUENCE: 678

Cys Ser Lys Thr Cys Gly Leu
1               5

<210> SEQ ID NO 679
<211> LENGTH: 6
<212> TYPE: PRT
<213> ORGANISM: Yellow Croaker

<400> SEQUENCE: 679

Cys Thr Glu Lys Asp Leu

```
1               5

<210> SEQ ID NO 680
<211> LENGTH: 6
<212> TYPE: PRT
<213> ORGANISM: Yellow Croaker

<400> SEQUENCE: 680

Gly Met Lys Lys Met Ile
1               5

<210> SEQ ID NO 681
<211> LENGTH: 6
<212> TYPE: PRT
<213> ORGANISM: Yellow Croaker

<400> SEQUENCE: 681

Lys Gln Met Gly Glu Leu
1               5

<210> SEQ ID NO 682
<211> LENGTH: 6
<212> TYPE: PRT
<213> ORGANISM: Yellow Croaker

<400> SEQUENCE: 682

Lys Ser Gly Glu Thr Phe
1               5

<210> SEQ ID NO 683
<211> LENGTH: 5
<212> TYPE: PRT
<213> ORGANISM: Yellow Croaker

<400> SEQUENCE: 683

Gln Thr Thr Glu Trp
1               5

<210> SEQ ID NO 684
<211> LENGTH: 5
<212> TYPE: PRT
<213> ORGANISM: Yellow Croaker

<400> SEQUENCE: 684

Arg Thr Pro Arg Leu
1               5

<210> SEQ ID NO 685
<211> LENGTH: 5
<212> TYPE: PRT
<213> ORGANISM: Yellow Croaker

<400> SEQUENCE: 685

Gln Cys Thr Cys Leu
1               5

<210> SEQ ID NO 686
<211> LENGTH: 4
<212> TYPE: PRT
<213> ORGANISM: Yellow Croaker

<400> SEQUENCE: 686

Asn Arg Arg Ile
1
```

```
<210> SEQ ID NO 687
<211> LENGTH: 5
<212> TYPE: PRT
<213> ORGANISM: Yellow Croaker

<400> SEQUENCE: 687

Cys Ser Met Asp Val
1               5

<210> SEQ ID NO 688
<211> LENGTH: 4
<212> TYPE: PRT
<213> ORGANISM: Yellow Croaker

<400> SEQUENCE: 688

Arg Pro Lys Phe
1

<210> SEQ ID NO 689
<211> LENGTH: 4
<212> TYPE: PRT
<213> ORGANISM: Yellow Croaker

<400> SEQUENCE: 689

Glu Ser Met Tyr
1

<210> SEQ ID NO 690
<211> LENGTH: 4
<212> TYPE: PRT
<213> ORGANISM: Yellow Croaker

<400> SEQUENCE: 690

Pro Met Glu Phe
1

<210> SEQ ID NO 691
<211> LENGTH: 4
<212> TYPE: PRT
<213> ORGANISM: Yellow Croaker

<400> SEQUENCE: 691

Arg Pro Thr Phe
1

<210> SEQ ID NO 692
<211> LENGTH: 4
<212> TYPE: PRT
<213> ORGANISM: Yellow Croaker

<400> SEQUENCE: 692

Glu Gln Ser Ile
1

<210> SEQ ID NO 693
<211> LENGTH: 4
<212> TYPE: PRT
<213> ORGANISM: Yellow Croaker

<400> SEQUENCE: 693

Ser Thr Arg Val
1

<210> SEQ ID NO 694
```

-continued

```
<211> LENGTH: 4
<212> TYPE: PRT
<213> ORGANISM: Yellow Croaker

<400> SEQUENCE: 694

Arg Asp Gly Ala
1

<210> SEQ ID NO 695
<211> LENGTH: 4
<212> TYPE: PRT
<213> ORGANISM: Yellow Croaker

<400> SEQUENCE: 695

Lys Ser Cys Ala
1

<210> SEQ ID NO 696
<211> LENGTH: 3
<212> TYPE: PRT
<213> ORGANISM: Yellow Croaker

<400> SEQUENCE: 696

Cys Asp Phe
1

<210> SEQ ID NO 697
<211> LENGTH: 4
<212> TYPE: PRT
<213> ORGANISM: Yellow Croaker

<400> SEQUENCE: 697

Met Gly Ser Ala
1

<210> SEQ ID NO 698
<211> LENGTH: 3
<212> TYPE: PRT
<213> ORGANISM: Yellow Croaker

<400> SEQUENCE: 698

Cys Met Val
1

<210> SEQ ID NO 699
<211> LENGTH: 4
<212> TYPE: PRT
<213> ORGANISM: Yellow Croaker

<400> SEQUENCE: 699

Gly Gly Thr Val
1

<210> SEQ ID NO 700
<211> LENGTH: 3
<212> TYPE: PRT
<213> ORGANISM: Yellow Croaker

<400> SEQUENCE: 700

Thr Cys Val
1

<210> SEQ ID NO 701
<211> LENGTH: 3
<212> TYPE: PRT
```

```
<213> ORGANISM: Yellow Croaker

<400> SEQUENCE: 701

Met Ser Ala
1

<210> SEQ ID NO 702
<211> LENGTH: 3
<212> TYPE: PRT
<213> ORGANISM: Yellow Croaker

<400> SEQUENCE: 702

Cys Thr Ala
1

<210> SEQ ID NO 703
<211> LENGTH: 2
<212> TYPE: PRT
<213> ORGANISM: Yellow Croaker

<400> SEQUENCE: 703

Arg Leu
1

<210> SEQ ID NO 704
<211> LENGTH: 3
<212> TYPE: PRT
<213> ORGANISM: Yellow Croaker

<400> SEQUENCE: 704

Gly Cys Val
1

<210> SEQ ID NO 705
<211> LENGTH: 3
<212> TYPE: PRT
<213> ORGANISM: Yellow Croaker

<400> SEQUENCE: 705

Cys Gly Val
1

<210> SEQ ID NO 706
<211> LENGTH: 2
<212> TYPE: PRT
<213> ORGANISM: Yellow Croaker

<400> SEQUENCE: 706

Ser Tyr
1

<210> SEQ ID NO 707
<211> LENGTH: 2
<212> TYPE: PRT
<213> ORGANISM: Yellow Croaker

<400> SEQUENCE: 707

Met Leu
1

<210> SEQ ID NO 708
<211> LENGTH: 2
<212> TYPE: PRT
<213> ORGANISM: Yellow Croaker
```

```
<400> SEQUENCE: 708

Pro Phe
1

<210> SEQ ID NO 709
<211> LENGTH: 3
<212> TYPE: PRT
<213> ORGANISM: Yellow Croaker

<400> SEQUENCE: 709

Asp Gly Ala
1

<210> SEQ ID NO 710
<211> LENGTH: 2
<212> TYPE: PRT
<213> ORGANISM: Yellow Croaker

<400> SEQUENCE: 710

Glu Ile
1

<210> SEQ ID NO 711
<211> LENGTH: 2
<212> TYPE: PRT
<213> ORGANISM: Yellow Croaker

<400> SEQUENCE: 711

Lys Val
1

<210> SEQ ID NO 712
<211> LENGTH: 2
<212> TYPE: PRT
<213> ORGANISM: Yellow Croaker

<400> SEQUENCE: 712

Cys Ile
1

<210> SEQ ID NO 713
<211> LENGTH: 2
<212> TYPE: PRT
<213> ORGANISM: Yellow Croaker

<400> SEQUENCE: 713

Cys Leu
1

<210> SEQ ID NO 714
<211> LENGTH: 2
<212> TYPE: PRT
<213> ORGANISM: Yellow Croaker

<400> SEQUENCE: 714

Pro Ile
1

<210> SEQ ID NO 715
<211> LENGTH: 2
<212> TYPE: PRT
<213> ORGANISM: Yellow Croaker

<400> SEQUENCE: 715
```

Pro Leu
1

<210> SEQ ID NO 716
<211> LENGTH: 2
<212> TYPE: PRT
<213> ORGANISM: Yellow Croaker

<400> SEQUENCE: 716

Met Ala
1

<210> SEQ ID NO 717
<211> LENGTH: 2
<212> TYPE: PRT
<213> ORGANISM: Yellow Croaker

<400> SEQUENCE: 717

Ser Leu
1

<210> SEQ ID NO 718
<211> LENGTH: 2
<212> TYPE: PRT
<213> ORGANISM: Yellow Croaker

<400> SEQUENCE: 718

Cys Ala
1

<210> SEQ ID NO 719
<211> LENGTH: 2
<212> TYPE: PRT
<213> ORGANISM: Yellow Croaker

<400> SEQUENCE: 719

Gly Ile
1

<210> SEQ ID NO 720
<211> LENGTH: 2
<212> TYPE: PRT
<213> ORGANISM: Yellow Croaker

<400> SEQUENCE: 720

Ser Ala
1

<210> SEQ ID NO 721
<211> LENGTH: 2
<212> TYPE: PRT
<213> ORGANISM: Yellow Croaker

<400> SEQUENCE: 721

Gly Val
1

<210> SEQ ID NO 722
<211> LENGTH: 2
<212> TYPE: PRT
<213> ORGANISM: Yellow Croaker

<400> SEQUENCE: 722

Gly Ala
1

<210> SEQ ID NO 723
<211> LENGTH: 12
<212> TYPE: PRT
<213> ORGANISM: Yellow Croaker

<400> SEQUENCE: 723

Met Met Glu Asp Asp Pro Gly Ser Gly Asp Glu Ile
1               5                   10

<210> SEQ ID NO 724
<211> LENGTH: 8
<212> TYPE: PRT
<213> ORGANISM: Yellow Croaker

<400> SEQUENCE: 724

Pro Glu Gly Pro Lys Cys Pro Phe
1               5

<210> SEQ ID NO 725
<211> LENGTH: 6
<212> TYPE: PRT
<213> ORGANISM: Yellow Croaker

<400> SEQUENCE: 725

Arg Cys Gln Cys His Leu
1               5

<210> SEQ ID NO 726
<211> LENGTH: 6
<212> TYPE: PRT
<213> ORGANISM: Yellow Croaker

<400> SEQUENCE: 726

Asn Met Pro Lys Ser Leu
1               5

<210> SEQ ID NO 727
<211> LENGTH: 6
<212> TYPE: PRT
<213> ORGANISM: Yellow Croaker

<400> SEQUENCE: 727

Pro Asp Asp Thr Thr Leu
1               5

<210> SEQ ID NO 728
<211> LENGTH: 6
<212> TYPE: PRT
<213> ORGANISM: Yellow Croaker

<400> SEQUENCE: 728

Gln Gly Met Ser His Val
1               5

<210> SEQ ID NO 729
<211> LENGTH: 5
<212> TYPE: PRT
<213> ORGANISM: Yellow Croaker

<400> SEQUENCE: 729

Lys Glu Asn Asp Phe
1               5

-continued

```
<210> SEQ ID NO 730
<211> LENGTH: 5
<212> TYPE: PRT
<213> ORGANISM: Yellow Croaker

<400> SEQUENCE: 730

Ser Asp His Lys Tyr
1               5

<210> SEQ ID NO 731
<211> LENGTH: 5
<212> TYPE: PRT
<213> ORGANISM: Yellow Croaker

<400> SEQUENCE: 731

His Glu Asn Glu Ile
1               5

<210> SEQ ID NO 732
<211> LENGTH: 5
<212> TYPE: PRT
<213> ORGANISM: Yellow Croaker

<400> SEQUENCE: 732

Gln Asn Asn Lys Ile
1               5

<210> SEQ ID NO 733
<211> LENGTH: 5
<212> TYPE: PRT
<213> ORGANISM: Yellow Croaker

<400> SEQUENCE: 733

Arg Gln Ser Gly Phe
1               5

<210> SEQ ID NO 734
<211> LENGTH: 5
<212> TYPE: PRT
<213> ORGANISM: Yellow Croaker

<400> SEQUENCE: 734

Ser Lys Asn Met Leu
1               5

<210> SEQ ID NO 735
<211> LENGTH: 5
<212> TYPE: PRT
<213> ORGANISM: Yellow Croaker

<400> SEQUENCE: 735

Gln Cys Ser Asp Leu
1               5

<210> SEQ ID NO 736
<211> LENGTH: 5
<212> TYPE: PRT
<213> ORGANISM: Yellow Croaker

<400> SEQUENCE: 736

Thr Lys Met Thr Ala
1               5

<210> SEQ ID NO 737
<211> LENGTH: 5
```

```
<212> TYPE: PRT
<213> ORGANISM: Yellow Croaker

<400> SEQUENCE: 737

Asn Ser Lys Lys Ala
1               5

<210> SEQ ID NO 738
<211> LENGTH: 5
<212> TYPE: PRT
<213> ORGANISM: Yellow Croaker

<400> SEQUENCE: 738

Asp Gly Asn Lys Ile
1               5

<210> SEQ ID NO 739
<211> LENGTH: 5
<212> TYPE: PRT
<213> ORGANISM: Yellow Croaker

<400> SEQUENCE: 739

Glu Asn Gly Thr Leu
1               5

<210> SEQ ID NO 740
<211> LENGTH: 5
<212> TYPE: PRT
<213> ORGANISM: Yellow Croaker

<400> SEQUENCE: 740

Gly Thr Gly Asp Phe
1               5

<210> SEQ ID NO 741
<211> LENGTH: 4
<212> TYPE: PRT
<213> ORGANISM: Yellow Croaker

<400> SEQUENCE: 741

Asn Asn Lys Ile
1

<210> SEQ ID NO 742
<211> LENGTH: 5
<212> TYPE: PRT
<213> ORGANISM: Yellow Croaker

<400> SEQUENCE: 742

Gly Ser Asn Pro Leu
1               5

<210> SEQ ID NO 743
<211> LENGTH: 5
<212> TYPE: PRT
<213> ORGANISM: Yellow Croaker

<400> SEQUENCE: 743

Cys Pro Pro Gly Leu
1               5

<210> SEQ ID NO 744
<211> LENGTH: 4
<212> TYPE: PRT
<213> ORGANISM: Yellow Croaker
```

<400> SEQUENCE: 744

Pro Lys Asp Ile
1

<210> SEQ ID NO 745
<211> LENGTH: 4
<212> TYPE: PRT
<213> ORGANISM: Yellow Croaker

<400> SEQUENCE: 745

Met Arg Ser Ala
1

<210> SEQ ID NO 746
<211> LENGTH: 4
<212> TYPE: PRT
<213> ORGANISM: Yellow Croaker

<400> SEQUENCE: 746

Asp Thr Asn Ile
1

<210> SEQ ID NO 747
<211> LENGTH: 4
<212> TYPE: PRT
<213> ORGANISM: Yellow Croaker

<400> SEQUENCE: 747

Asp Arg Ser Ala
1

<210> SEQ ID NO 748
<211> LENGTH: 4
<212> TYPE: PRT
<213> ORGANISM: Yellow Croaker

<400> SEQUENCE: 748

Asp Asn Asn Ala
1

<210> SEQ ID NO 749
<211> LENGTH: 3
<212> TYPE: PRT
<213> ORGANISM: Yellow Croaker

<400> SEQUENCE: 749

Arg Lys Lys
1

<210> SEQ ID NO 750
<211> LENGTH: 4
<212> TYPE: PRT
<213> ORGANISM: Yellow Croaker

<400> SEQUENCE: 750

Thr Glu Thr Ala
1

<210> SEQ ID NO 751
<211> LENGTH: 3
<212> TYPE: PRT
<213> ORGANISM: Yellow Croaker

<400> SEQUENCE: 751

Arg Glu Leu
1

<210> SEQ ID NO 752
<211> LENGTH: 4
<212> TYPE: PRT
<213> ORGANISM: Yellow Croaker

<400> SEQUENCE: 752

Pro Thr Ser Leu
1

<210> SEQ ID NO 753
<211> LENGTH: 3
<212> TYPE: PRT
<213> ORGANISM: Yellow Croaker

<400> SEQUENCE: 753

Gln Arg Leu
1

<210> SEQ ID NO 754
<211> LENGTH: 4
<212> TYPE: PRT
<213> ORGANISM: Yellow Croaker

<400> SEQUENCE: 754

Ser Asn Pro Val
1

<210> SEQ ID NO 755
<211> LENGTH: 4
<212> TYPE: PRT
<213> ORGANISM: Yellow Croaker

<400> SEQUENCE: 755

Pro Lys Gly Leu
1

<210> SEQ ID NO 756
<211> LENGTH: 3
<212> TYPE: PRT
<213> ORGANISM: Yellow Croaker

<400> SEQUENCE: 756

Lys Arg Val
1

<210> SEQ ID NO 757
<211> LENGTH: 3
<212> TYPE: PRT
<213> ORGANISM: Yellow Croaker

<400> SEQUENCE: 757

Met Glu Leu
1

<210> SEQ ID NO 758
<211> LENGTH: 3
<212> TYPE: PRT
<213> ORGANISM: Yellow Croaker

<400> SEQUENCE: 758

Lys Glu Ile

<210> SEQ ID NO 759
<211> LENGTH: 3
<212> TYPE: PRT
<213> ORGANISM: Yellow Croaker

<400> SEQUENCE: 759

Gln Glu Leu
1

<210> SEQ ID NO 760
<211> LENGTH: 4
<212> TYPE: PRT
<213> ORGANISM: Yellow Croaker

<400> SEQUENCE: 760

Pro Pro Gly Leu
1

<210> SEQ ID NO 761
<211> LENGTH: 3
<212> TYPE: PRT
<213> ORGANISM: Yellow Croaker

<400> SEQUENCE: 761

Arg Cys Val
1

<210> SEQ ID NO 762
<211> LENGTH: 3
<212> TYPE: PRT
<213> ORGANISM: Yellow Croaker

<400> SEQUENCE: 762

Asn Glu Ile
1

<210> SEQ ID NO 763
<211> LENGTH: 3
<212> TYPE: PRT
<213> ORGANISM: Yellow Croaker

<400> SEQUENCE: 763

Lys Asn Leu
1

<210> SEQ ID NO 764
<211> LENGTH: 3
<212> TYPE: PRT
<213> ORGANISM: Yellow Croaker

<400> SEQUENCE: 764

Asn Lys Ile
1

<210> SEQ ID NO 765
<211> LENGTH: 3
<212> TYPE: PRT
<213> ORGANISM: Yellow Croaker

<400> SEQUENCE: 765

Pro His Leu
1

<210> SEQ ID NO 766
<211> LENGTH: 3
<212> TYPE: PRT
<213> ORGANISM: Yellow Croaker

<400> SEQUENCE: 766

Thr Glu Ile
1

<210> SEQ ID NO 767
<211> LENGTH: 3
<212> TYPE: PRT
<213> ORGANISM: Yellow Croaker

<400> SEQUENCE: 767

Thr Lys Leu
1

<210> SEQ ID NO 768
<211> LENGTH: 3
<212> TYPE: PRT
<213> ORGANISM: Yellow Croaker

<400> SEQUENCE: 768

Thr Lys Ile
1

<210> SEQ ID NO 769
<211> LENGTH: 3
<212> TYPE: PRT
<213> ORGANISM: Yellow Croaker

<400> SEQUENCE: 769

Gly Asn Tyr
1

<210> SEQ ID NO 770
<211> LENGTH: 3
<212> TYPE: PRT
<213> ORGANISM: Yellow Croaker

<400> SEQUENCE: 770

Ser Glu Leu
1

<210> SEQ ID NO 771
<211> LENGTH: 3
<212> TYPE: PRT
<213> ORGANISM: Yellow Croaker

<400> SEQUENCE: 771

Lys Lys Ala
1

<210> SEQ ID NO 772
<211> LENGTH: 3
<212> TYPE: PRT
<213> ORGANISM: Yellow Croaker

<400> SEQUENCE: 772

Gln Pro Val
1

<210> SEQ ID NO 773

```
<211> LENGTH: 4
<212> TYPE: PRT
<213> ORGANISM: Yellow Croaker

<400> SEQUENCE: 773

Asp Gly Gly Ala
1

<210> SEQ ID NO 774
<211> LENGTH: 3
<212> TYPE: PRT
<213> ORGANISM: Yellow Croaker

<400> SEQUENCE: 774

Glu Gly Leu
1

<210> SEQ ID NO 775
<211> LENGTH: 3
<212> TYPE: PRT
<213> ORGANISM: Yellow Croaker

<400> SEQUENCE: 775

Lys Gly Leu
1

<210> SEQ ID NO 776
<211> LENGTH: 3
<212> TYPE: PRT
<213> ORGANISM: Yellow Croaker

<400> SEQUENCE: 776

Ser Pro Leu
1

<210> SEQ ID NO 777
<211> LENGTH: 2
<212> TYPE: PRT
<213> ORGANISM: Yellow Croaker

<400> SEQUENCE: 777

Met Tyr
1

<210> SEQ ID NO 778
<211> LENGTH: 2
<212> TYPE: PRT
<213> ORGANISM: Yellow Croaker

<400> SEQUENCE: 778

Cys Trp
1

<210> SEQ ID NO 779
<211> LENGTH: 3
<212> TYPE: PRT
<213> ORGANISM: Yellow Croaker

<400> SEQUENCE: 779

Thr Ser Val
1

<210> SEQ ID NO 780
<211> LENGTH: 3
<212> TYPE: PRT
```

-continued

```
<213> ORGANISM: Yellow Croaker

<400> SEQUENCE: 780

Lys Ser Ala
1

<210> SEQ ID NO 781
<211> LENGTH: 3
<212> TYPE: PRT
<213> ORGANISM: Yellow Croaker

<400> SEQUENCE: 781

Ser Ser Val
1

<210> SEQ ID NO 782
<211> LENGTH: 2
<212> TYPE: PRT
<213> ORGANISM: Yellow Croaker

<400> SEQUENCE: 782

Arg Ile
1

<210> SEQ ID NO 783
<211> LENGTH: 2
<212> TYPE: PRT
<213> ORGANISM: Yellow Croaker

<400> SEQUENCE: 783

Arg Ile
1

<210> SEQ ID NO 784
<211> LENGTH: 2
<212> TYPE: PRT
<213> ORGANISM: Yellow Croaker

<400> SEQUENCE: 784

Asp Phe
1

<210> SEQ ID NO 785
<211> LENGTH: 2
<212> TYPE: PRT
<213> ORGANISM: Yellow Croaker

<400> SEQUENCE: 785

Pro Tyr
1

<210> SEQ ID NO 786
<211> LENGTH: 3
<212> TYPE: PRT
<213> ORGANISM: Yellow Croaker

<400> SEQUENCE: 786

Gly Ser Leu
1

<210> SEQ ID NO 787
<211> LENGTH: 3
<212> TYPE: PRT
<213> ORGANISM: Yellow Croaker
```

<400> SEQUENCE: 787

Ser Gly Ile
1

<210> SEQ ID NO 788
<211> LENGTH: 2
<212> TYPE: PRT
<213> ORGANISM: Yellow Croaker

<400> SEQUENCE: 788

Arg Val
1

<210> SEQ ID NO 789
<211> LENGTH: 2
<212> TYPE: PRT
<213> ORGANISM: Yellow Croaker

<400> SEQUENCE: 789

His Leu
1

<210> SEQ ID NO 790
<211> LENGTH: 2
<212> TYPE: PRT
<213> ORGANISM: Yellow Croaker

<400> SEQUENCE: 790

Ser Tyr
1

<210> SEQ ID NO 791
<211> LENGTH: 2
<212> TYPE: PRT
<213> ORGANISM: Yellow Croaker

<400> SEQUENCE: 791

Thr Phe
1

<210> SEQ ID NO 792
<211> LENGTH: 2
<212> TYPE: PRT
<213> ORGANISM: Yellow Croaker

<400> SEQUENCE: 792

Pro Phe
1

<210> SEQ ID NO 793
<211> LENGTH: 2
<212> TYPE: PRT
<213> ORGANISM: Yellow Croaker

<400> SEQUENCE: 793

Lys Leu
1

<210> SEQ ID NO 794
<211> LENGTH: 2
<212> TYPE: PRT
<213> ORGANISM: Yellow Croaker

<400> SEQUENCE: 794

```
Gln Leu
1

<210> SEQ ID NO 795
<211> LENGTH: 2
<212> TYPE: PRT
<213> ORGANISM: Yellow Croaker

<400> SEQUENCE: 795

Ser Phe
1

<210> SEQ ID NO 796
<211> LENGTH: 2
<212> TYPE: PRT
<213> ORGANISM: Yellow Croaker

<400> SEQUENCE: 796

Asp Leu
1

<210> SEQ ID NO 797
<211> LENGTH: 2
<212> TYPE: PRT
<213> ORGANISM: Yellow Croaker

<400> SEQUENCE: 797

Glu Val
1

<210> SEQ ID NO 798
<211> LENGTH: 2
<212> TYPE: PRT
<213> ORGANISM: Yellow Croaker

<400> SEQUENCE: 798

Gln Val
1

<210> SEQ ID NO 799
<211> LENGTH: 2
<212> TYPE: PRT
<213> ORGANISM: Yellow Croaker

<400> SEQUENCE: 799

Cys Leu
1

<210> SEQ ID NO 800
<211> LENGTH: 2
<212> TYPE: PRT
<213> ORGANISM: Yellow Croaker

<400> SEQUENCE: 800

Thr Ile
1

<210> SEQ ID NO 801
<211> LENGTH: 2
<212> TYPE: PRT
<213> ORGANISM: Yellow Croaker

<400> SEQUENCE: 801

Asn Val
1
```

<210> SEQ ID NO 802
<211> LENGTH: 2
<212> TYPE: PRT
<213> ORGANISM: Yellow Croaker

<400> SEQUENCE: 802

His Ala
1

<210> SEQ ID NO 803
<211> LENGTH: 2
<212> TYPE: PRT
<213> ORGANISM: Yellow Croaker

<400> SEQUENCE: 803

Ser Leu
1

<210> SEQ ID NO 804
<211> LENGTH: 2
<212> TYPE: PRT
<213> ORGANISM: Yellow Croaker

<400> SEQUENCE: 804

Lys Ala
1

<210> SEQ ID NO 805
<211> LENGTH: 2
<212> TYPE: PRT
<213> ORGANISM: Yellow Croaker

<400> SEQUENCE: 805

Pro Val
1

<210> SEQ ID NO 806
<211> LENGTH: 2
<212> TYPE: PRT
<213> ORGANISM: Yellow Croaker

<400> SEQUENCE: 806

Thr Ala
1

<210> SEQ ID NO 807
<211> LENGTH: 2
<212> TYPE: PRT
<213> ORGANISM: Yellow Croaker

<400> SEQUENCE: 807

Gly Leu
1

<210> SEQ ID NO 808
<211> LENGTH: 2
<212> TYPE: PRT
<213> ORGANISM: Yellow Croaker

<400> SEQUENCE: 808

Gly Ile
1

```
<210> SEQ ID NO 809
<211> LENGTH: 2
<212> TYPE: PRT
<213> ORGANISM: Yellow Croaker

<400> SEQUENCE: 809

Pro Ala
1
```